US009452138B2

(12) United States Patent
Trollsas et al.

(10) Patent No.: US 9,452,138 B2
(45) Date of Patent: Sep. 27, 2016

(54) DELIVERY OF BIOLOGIC THERAPEUTICS

(71) Applicant: Abbott Cardiovascular Systems Inc., Santa Clara, CA (US)

(72) Inventors: Mikael Trollsas, San Jose, CA (US); John Stankus, Campbell, CA (US); James Su, San Bruno, CA (US); Syed Hossainy, hayward, CA (US); Joshua Takeshi Smith, Campbell, CA (US); Shadid Askar, Round Rock, TX (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 14/142,651

(22) Filed: Dec. 27, 2013

(65) Prior Publication Data
US 2014/0186446 A1    Jul. 3, 2014

Related U.S. Application Data

(60) Provisional application No. 61/747,176, filed on Dec. 28, 2012.

(51) Int. Cl.
| A61K 38/00 | (2006.01) |
| A61K 9/14 | (2006.01) |
| A61K 9/00 | (2006.01) |
| A61K 47/10 | (2006.01) |
| A61K 9/08 | (2006.01) |
| C07K 16/24 | (2006.01) |
| C07K 16/40 | (2006.01) |
| A61K 38/21 | (2006.01) |
| A61K 39/00 | (2006.01) |

(52) U.S. Cl.
CPC ............. *A61K 9/146* (2013.01); *A61K 9/0019* (2013.01); *A61K 9/08* (2013.01); *A61K 47/10* (2013.01); *C07K 16/241* (2013.01); *C07K 16/40* (2013.01); *A61K 38/215* (2013.01); *A61K 2039/505* (2013.01)

(58) Field of Classification Search
None
See application file for complete search history.

(56) References Cited

U.S. PATENT DOCUMENTS

| 4,332,917 | A | * | 6/1982 | Heslinga et al. | ............. | 521/134 |
| 5,971,953 | A | * | 10/1999 | Bachynsky | .................... | 604/90 |
| 7,732,190 | B2 | | 6/2010 | Michal et al. | | |
| 2001/0053548 | A1 | | 12/2001 | Rybak et al. | | |
| 2007/0244301 | A1 | * | 10/2007 | Siekmann et al. | ............ | 530/383 |
| 2009/0226519 | A1 | | 9/2009 | Claude et al. | | |
| 2010/0292146 | A1 | * | 11/2010 | Seibl et al. | .................... | 514/8.8 |
| 2012/0027775 | A1 | * | 2/2012 | Won et al. | ................. | 424/158.1 |
| 2012/0035344 | A1 | * | 2/2012 | Siekmann et al. | ............ | 530/303 |

FOREIGN PATENT DOCUMENTS

| WO | WO 2006/088336 |    | 8/2006 |
| WO | WO 2012/145439 | * | 10/2012 |

OTHER PUBLICATIONS

Creative PEGWorks (downloaded online on Nov. 22, 2014 from URL: < http://www.creativepegworks.com/>, available online since Nov. 9, 2011).*
Elbert et al, Protein delivery from materials formed by self-selective conjugate addition reactions (Journal of Controlled Release 76 (2001) 11-25).*
Hoff et al, Adalimumab therapy reduces hand bone loss in early rheumatoid arthritis: explorative analyses from the Premier study (Ann Rheum Dis. Jul. 2009;68(7):1171-6).*
Rau, Adalimumab (a fully human anti-tumour necrosis factor alpha monoclonal antibody) in the treatment of active rheumatoid arthritis: the initial results of five trials (Ann Rheum Dis 2002;61(Suppl II):ii70-ii73).*
International Search Report and Written Opinion for PCT/US 2013/078102, mailed Jun. 25, 2014, 10 pgs.

* cited by examiner

*Primary Examiner* — Marcela M Cordero Garcia
*Assistant Examiner* — Sergio Coffa
(74) *Attorney, Agent, or Firm* — Squire Patton Boggs (US) LLP

(57) ABSTRACT

Formulations and methods are disclosed which provide controlled, sustained release of a biologic therapeutic to a space within the body. More specifically, formulations comprising a plurality of hydrophilic polymer strands, and methods of forming and administering such formulations, are disclosed. In some embodiments, the formulations exhibit a burst release, an initial release, a triphasic release, and release over thirty to ninety days of the biologic therapeutic. In some embodiments, the formulations exhibit reversible precipitation of the biologic therapeutic into precipitates having a diameter of about 50 nm to about 10 μm.

25 Claims, 55 Drawing Sheets

Image of presence of formulated mAb hydrogel 4h after subcutaneous injection.

Image of 20uL fluorescently labeled mAb formulated hydrogel 4h after intra-articular injection.

Image of extracted fluorescently labeled mAb formulated hydrogel 4h post intra-articular injection.

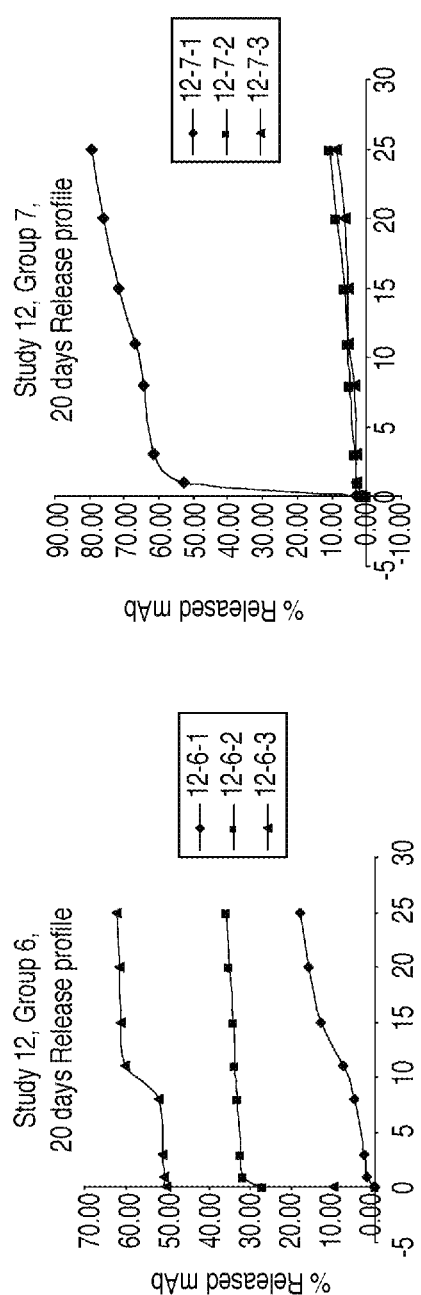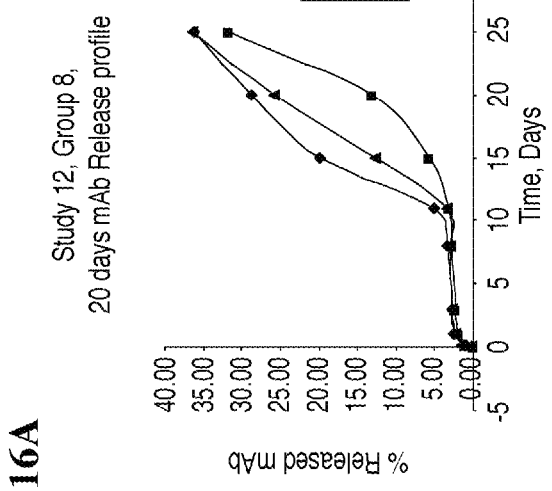
FIGURE 16A
FIGURE 16B
FIGURE 16C

DELIVERY OF BIOLOGIC THERAPEUTICS

1. BACKGROUND OF THE INVENTION

Biologic therapeutics are well known and widely prescribed due to their unmatched benefits and efficacy. However, such biologic therapeutics may be associated with undesired side effects at high systemic concentrations. Additionally, repeated painful and expensive administration of biologics may be required, decreasing certain benefits and appeal to patients and providers. It is therefore desirable to provide controlled, sustained release formulations for biologic therapeutic delivery to reduce systemic exposure and frequency of administration, as well as to improve biologic therapeutic safety and patient compliance.

Osteoarthritis is one example of a pathology with a significant unmet need for controlled release biologic therapeutics. Over 38 million people are currently affected by osteoarthritis in the United States alone. Osteoarthritis is a progressive ailment characterized by joint pain, stiffness and limited range of motion, and typically affects joints of the hands, spine, hip and knee. There currently are no FDA approved drugs for disease modification in osteoarthritis. Currently, osteoarthritis pain is managed by NSAIDs and opioids. Similarly, treatment of macular degeneration, which progressively impairs vision and leads to blindness, is hampered by the necessity of repeated injections into the eye. Controlled release formulations of biologic therapeutics providing low systemic exposure, low maximum local and systemic concentrations, less frequent dosing requirements, higher effective dosing and improved compliance, such as those disclosed herein, represent a significant breakthrough in treatment of osteoarthritis, macular degeneration, and other ailments.

2. SUMMARY OF THE INVENTION

The purposes and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims herein, as well as from the appended drawings.

To achieve these and other advantages and in accordance with the purpose of the disclosed subject matter, as embodied and broadly described, the disclosed subject matter includes formulations, kits and methods for controlled, sustained release of a biologic therapeutic to a space within a body. In accordance with the disclosed subject matter, a formulation comprising a biologic therapeutic and a plurality of hydrophilic polymer strands is provided, wherein each of said polymer strands comprises a functional group capable of inter-polymer polymerization, i.e. cross-linking Polymerization of the formulation of the disclosed subject matter provides a number of advantages and unique characteristics, including a "burst effect" of biologic therapeutic release within 24 hours of administration of the formulation to a space in the body; an initial cumulative release of biologic therapeutic within 7 days of administration of the formulation to a space in the body; a triphasic release profile; and a release duration of one to three months after administration to a space within the body for complete release of the biologic therapeutic.

According to another aspect of the disclosed subject matter, a formulation for providing reversible precipitation of biologic therapeutics from a space within the body is provided. The formulation includes a biologic therapeutic and a plurality of hydrophilic polymer strands, each of said polymer strands comprising a functional group capable of inter-polymer polymerization. Upon polymerization of the plurality of hydrophilic polymer strands, the cross-linked composition exhibits reversible precipitation of the biologic therapeutic, wherein the precipitant includes precipitates of about 50 nm to about 10 μm in diameter.

In another aspect of the disclosed subject matter, methods of administering a cross-linked composition including a reversibly precipitated biologic therapeutic are provided. The methods include combining a biologic therapeutic and a plurality of hydrophilic polymer strands to form a combination, mixing the combination with an activation buffer to induce inter-polymer polymerization of the hydrophilic polymer strands to form cross-linked composition which includes reversibly precipitated biologic therapeutic, and administering the cross-linked composition to a patient in need thereof. In further embodiments, methods of treating diseases including, without limitation, cancer, diseases of the eye, inflammation, autoimmune disease, wounds, fractures, infectious disease, or cardiovascular disease, are provided.

In still another aspect of the disclosed subject matter, formulations for producing a local concentration of a biologic therapeutic that is between about ten to about ten thousand times greater than the concentration of the biologic therapeutic in the systemic circulation for between about one to about ninety days are provided.

3. BRIEF DESCRIPTIONS OF THE DRAWINGS

FIG. 1A, FIG. 1B, and FIG. 1C depict a schematic illustration of one aspect of the disclosed subject matter, wherein a controlled, sustained release formulation of a biologic therapeutic is formed by cross-linking a plurality of hydrophilic polymer strands (1A and 1B) to form a cross-linked composition (1C) which can be administered to a space within the body.

FIG. 2 depicts a schematic illustration of premixed formulations according to one aspect of the disclosed subject matter.

FIG. 3A and FIG. 3B depict in vitro sustained release kinetics of the biologic therapeutic from cross-linked compositions comprising 4-arm, 8-arm and mixed 4-arm and 8-arm hydrophilic polymer strands at 10% (3A) and 15% (3B) concentrations.

Figure 6A:
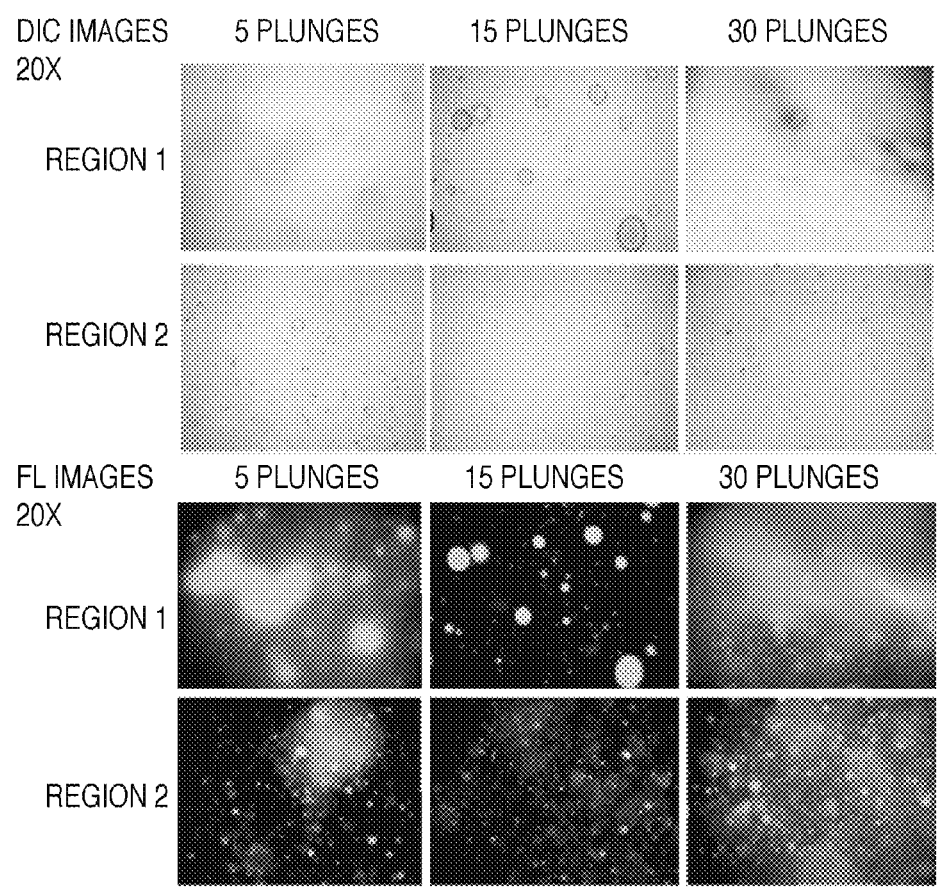
Figure 6B:
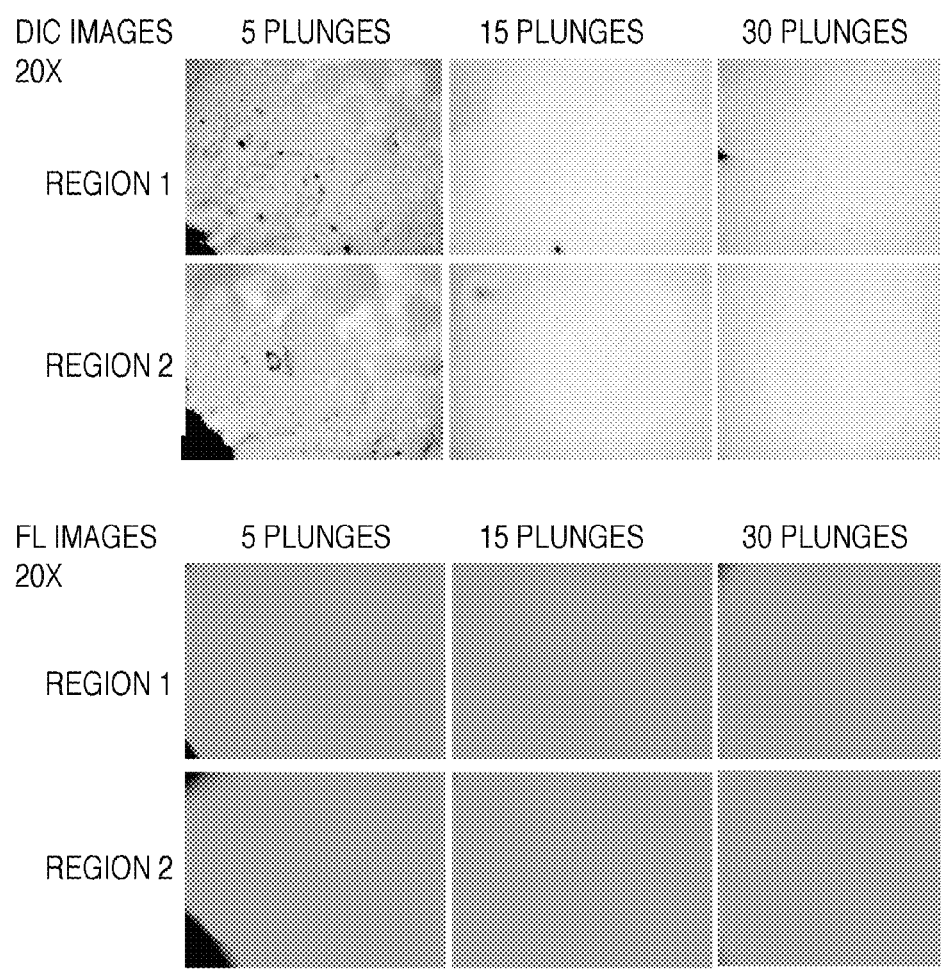
Figure 6C:
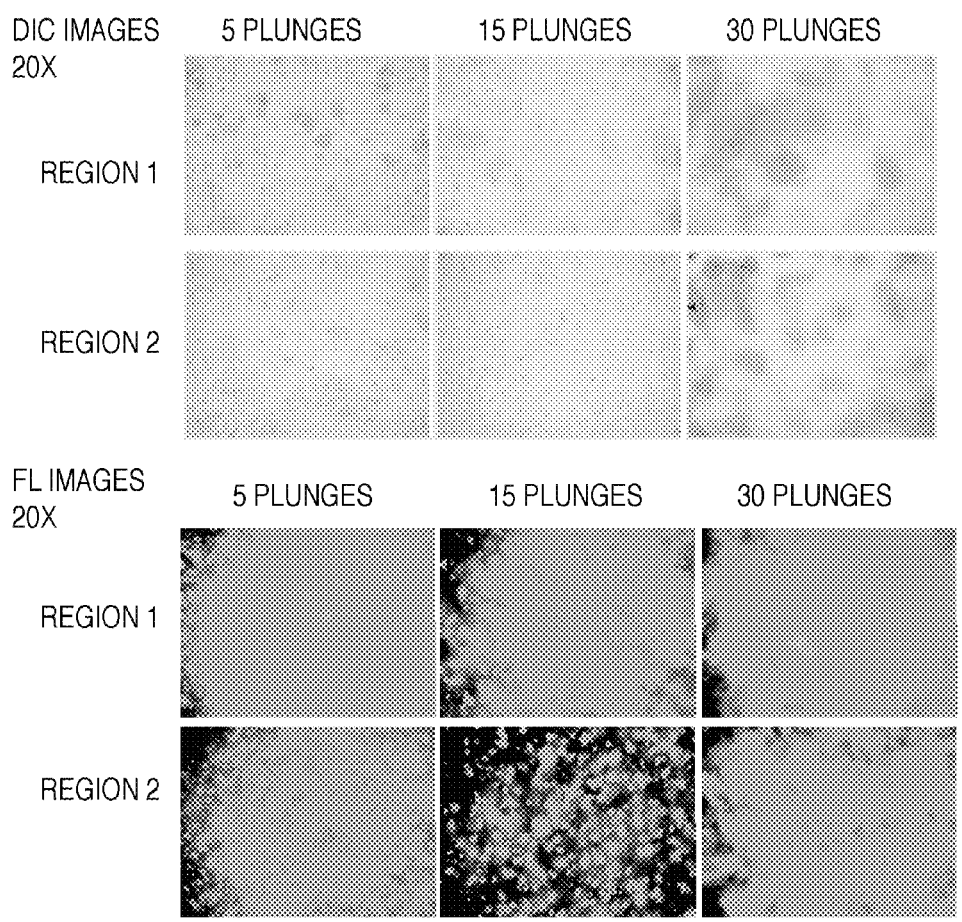
Figure 6D:
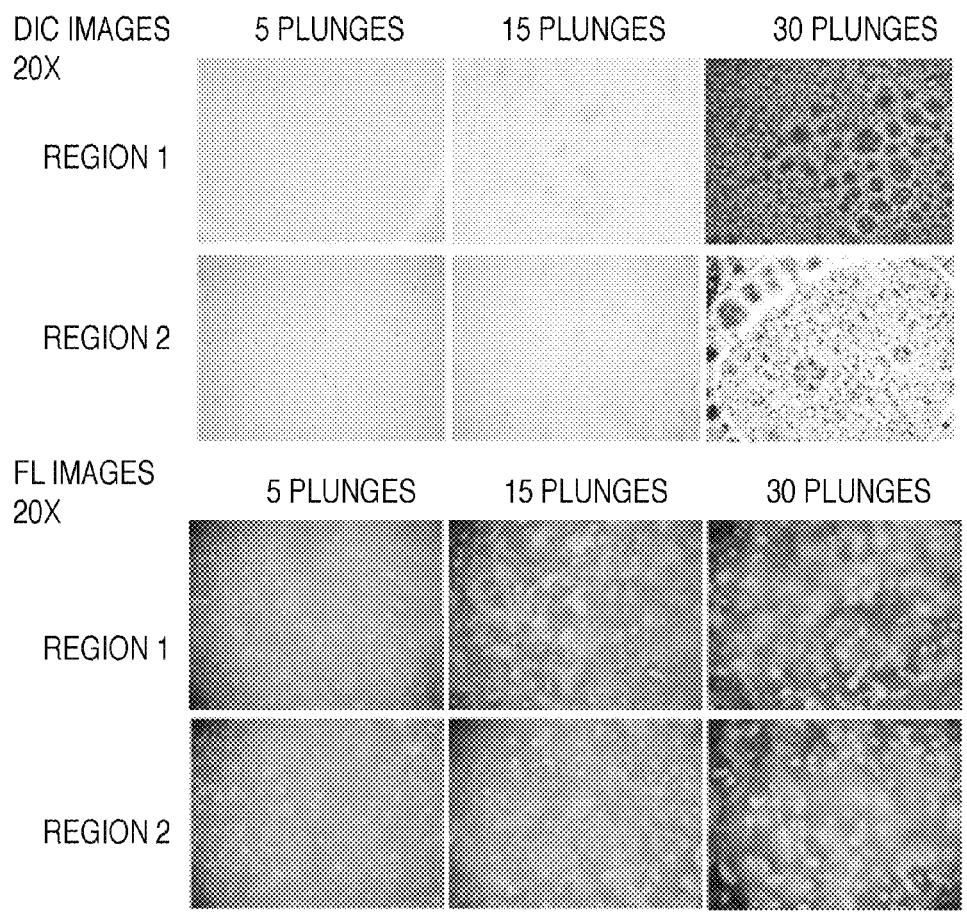

FIG. 6A depicts reversibly precipitated fluorescently-tagged monoclonal antibody precipitates after generation of a 10% 4-arm PEG solids cross-linked composition by 5, 15 and 30 syringe plunges. FIG. 6B depicts reversibly precipitated fluorescently-tagged monoclonal antibody precipitates after generation of a 10% 8-arm PEG solids cross-linked composition by 5, 15 and 30 syringe plunges. FIG. 6C depicts reversibly precipitated fluorescently-tagged monoclonal antibody precipitates after generation of a 20% 4-arm PEG solids cross-linked composition by 5, 15 and 30 syringe plunges. FIG. 6D depicts reversibly precipitated fluorescently-tagged monoclonal antibody precipitates after generation of a 20% 8-arm PEG solids cross-linked composition by 5, 15 and 30 syringe plunges.

Figure 7:
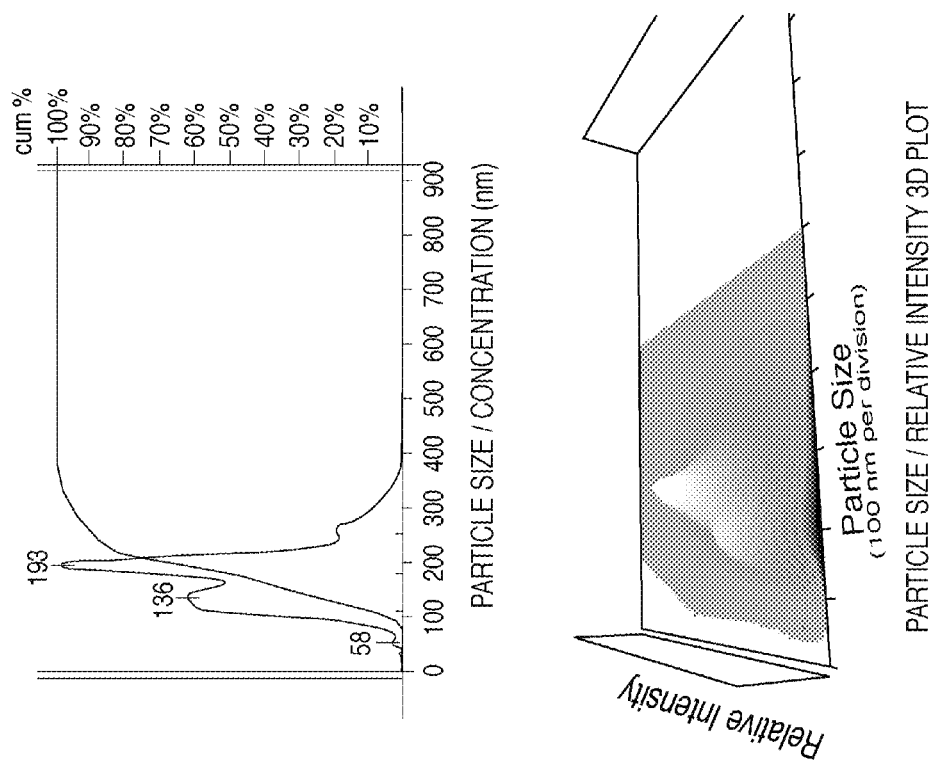

FIG. 7 is an illustration of the size distribution of biological precipitates that form in some formulations of the disclosed subject matter.

Figure 8A:
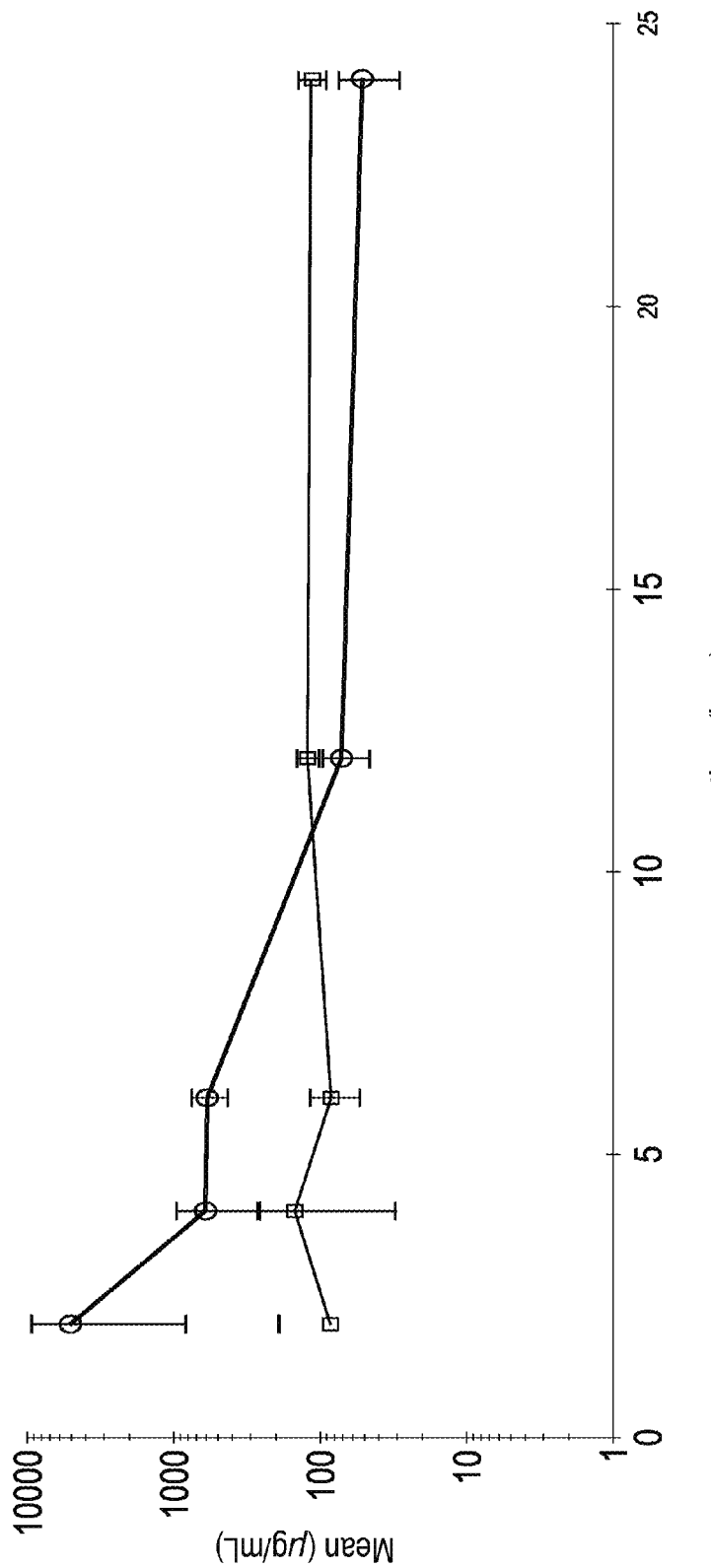
Figure 8B:
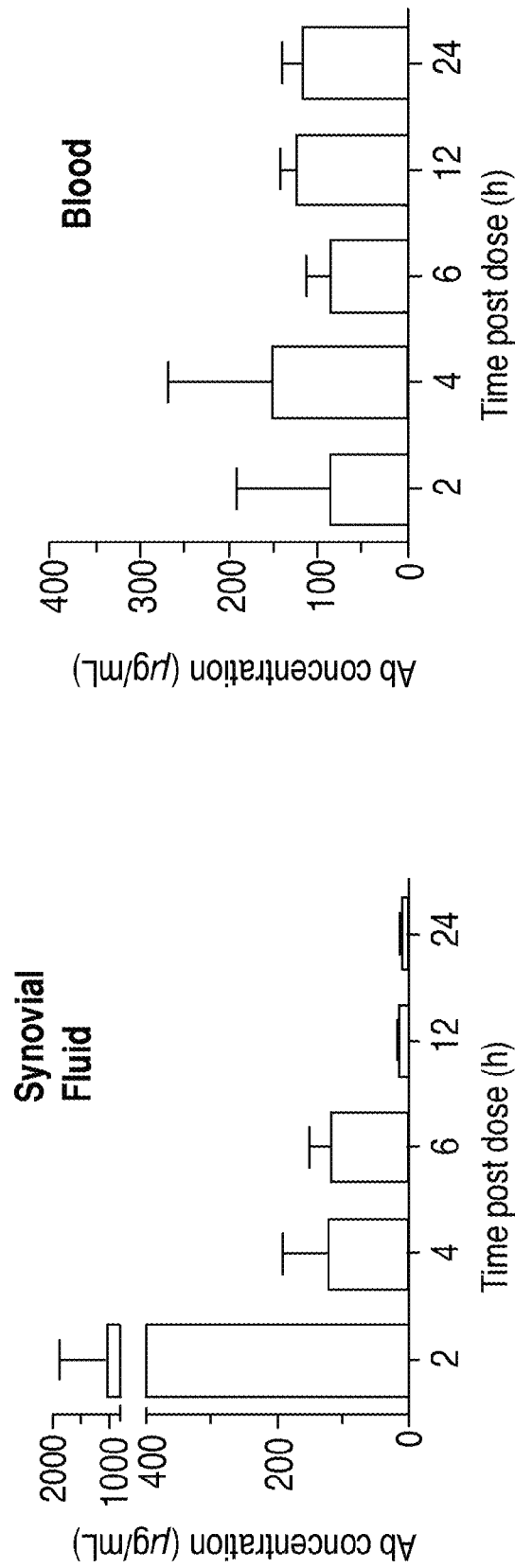

FIG. 8A depicts the serum and synovial fluid concentrations of unformulated monoclonal antibody at 2, 4, 6, 12 and 24 hours after administration to the intra-articular space of the hind limbs of healthy rats. FIG. 8B provides this information in the form of a bar graph.

Figures 9A, 9B:
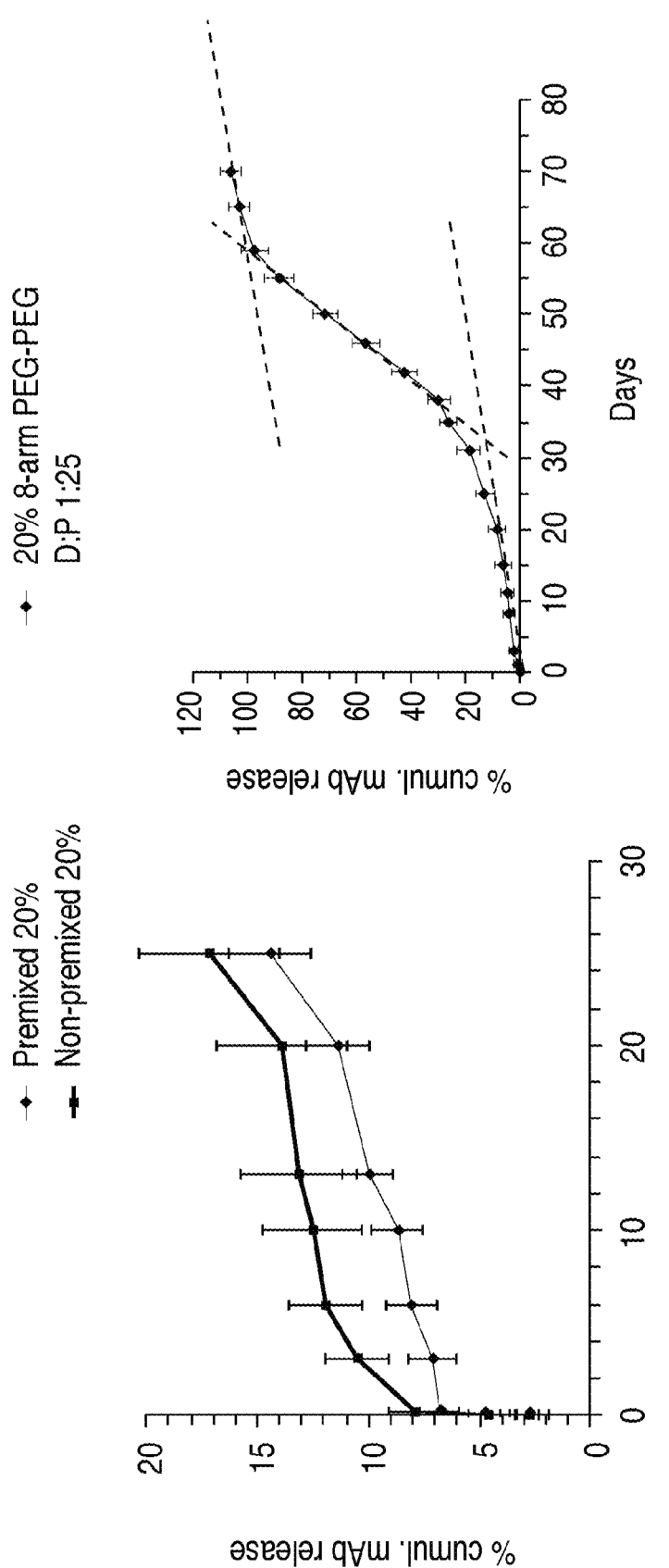

FIG. 9A depicts in vitro release kinetics of a monoclonal antibody from 8-arm PEG-SH/PEG-Acr cross-linked compositions. FIG. 9B illustrates an exemplary triphasic release profile according to one aspect of the disclosed subject matter.

Figure 10:
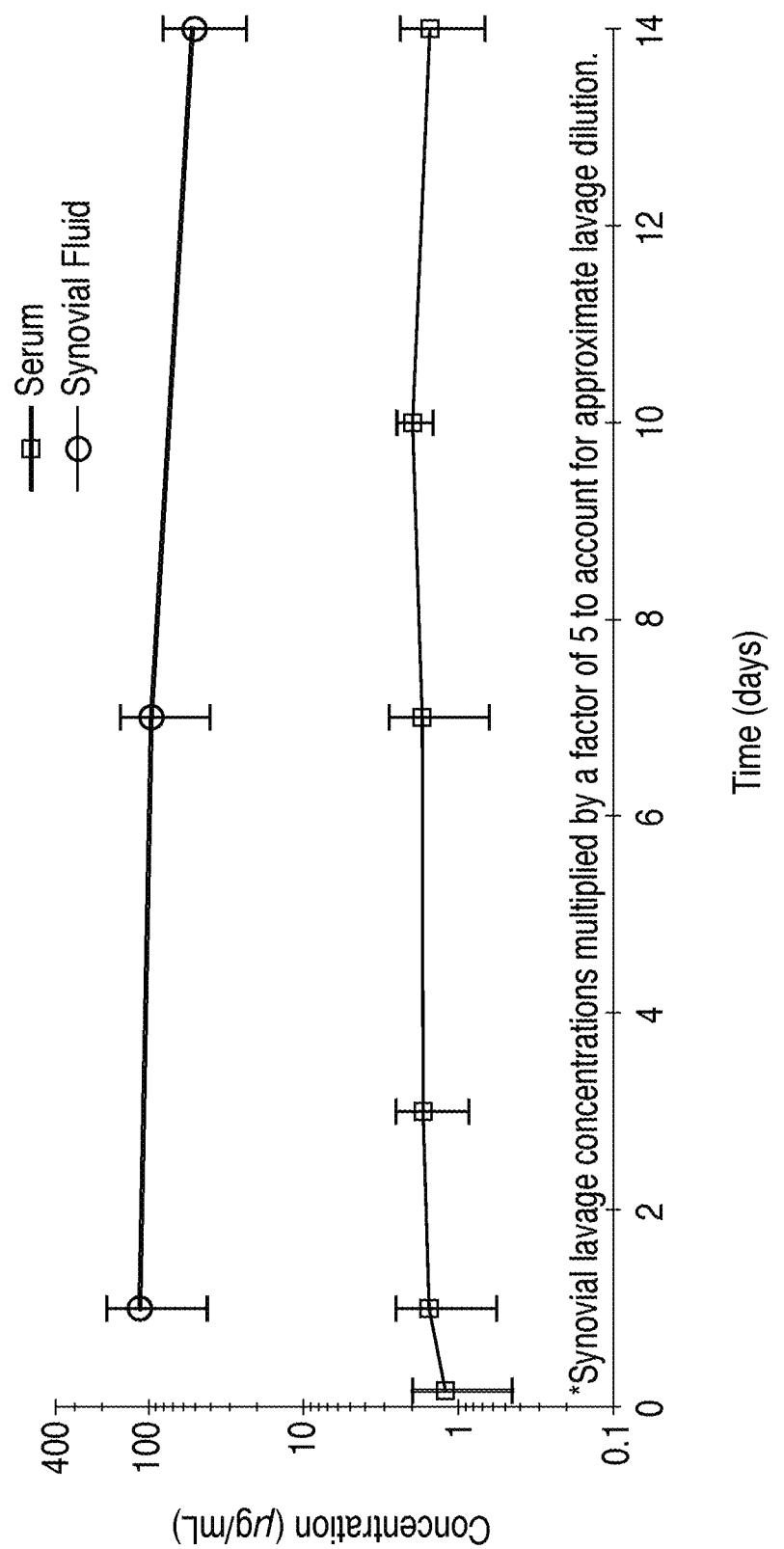

FIG. 10 depicts the serum and synovial fluid concentrations of monoclonal antibody delivered via cross-linked hydrogel compositions for 14 days following administration to the intra-articular space of the hind limbs of healthy rats.

Figure 11A:
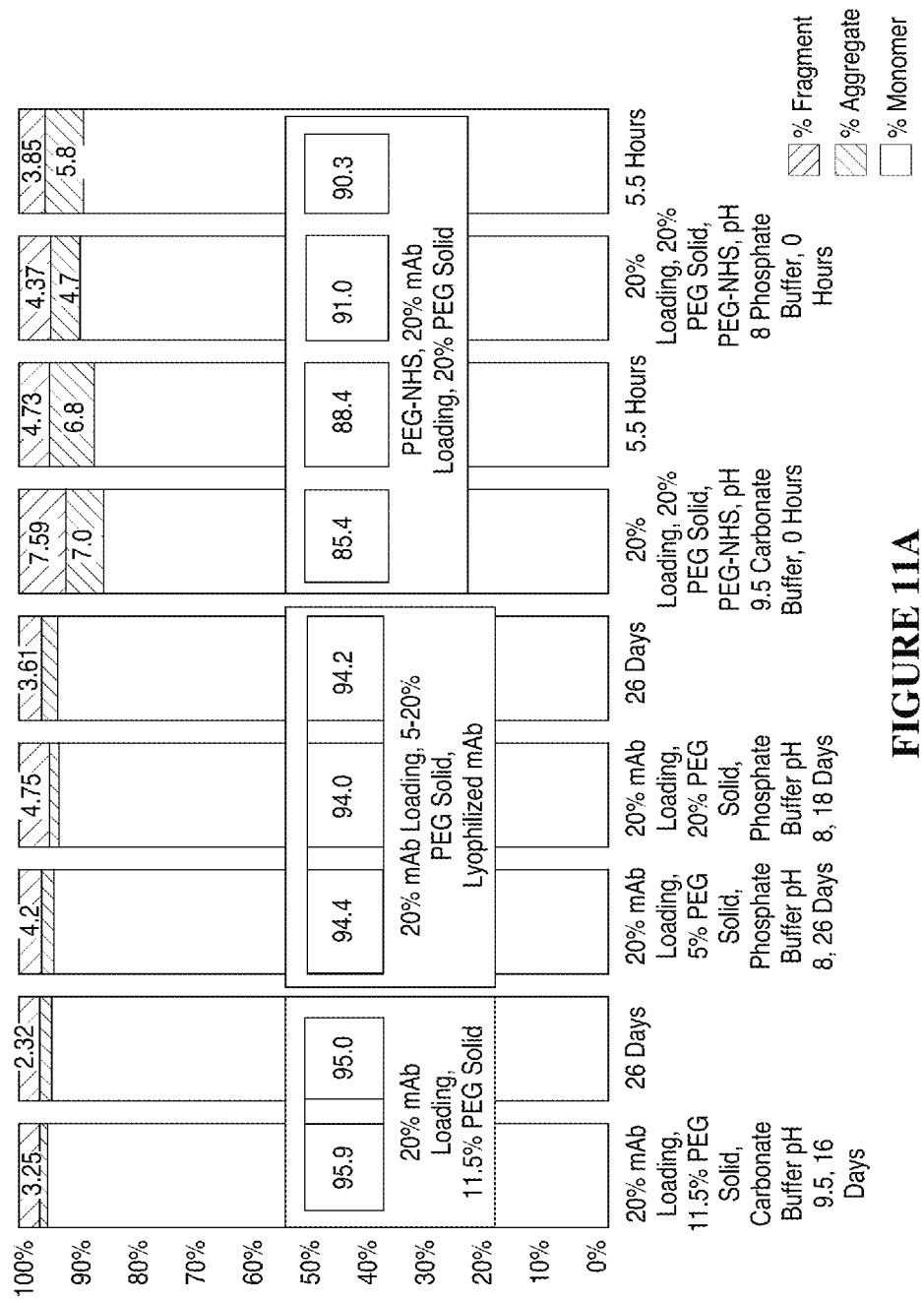
Figure 11B:
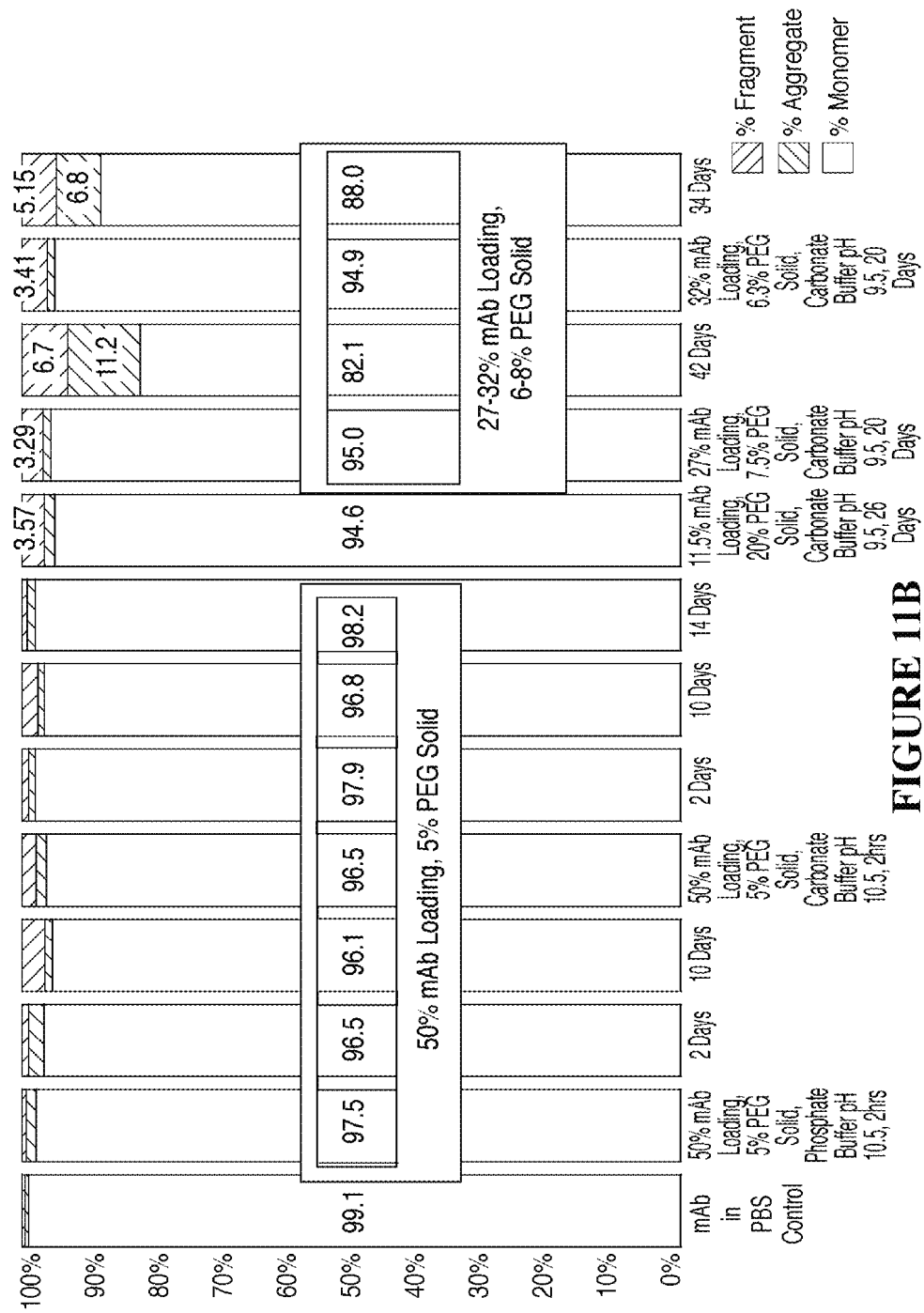

FIG. 11A and FIG. 11B depict the proportions of monomers, aggregates and fragments of monoclonal antibody released in vitro from various cross-linked compositions comprised of 4-arm hydrophilic polymer strands as indicated 18 and 26 days after formation as determined by size exclusion chromatography.

Figure 12:
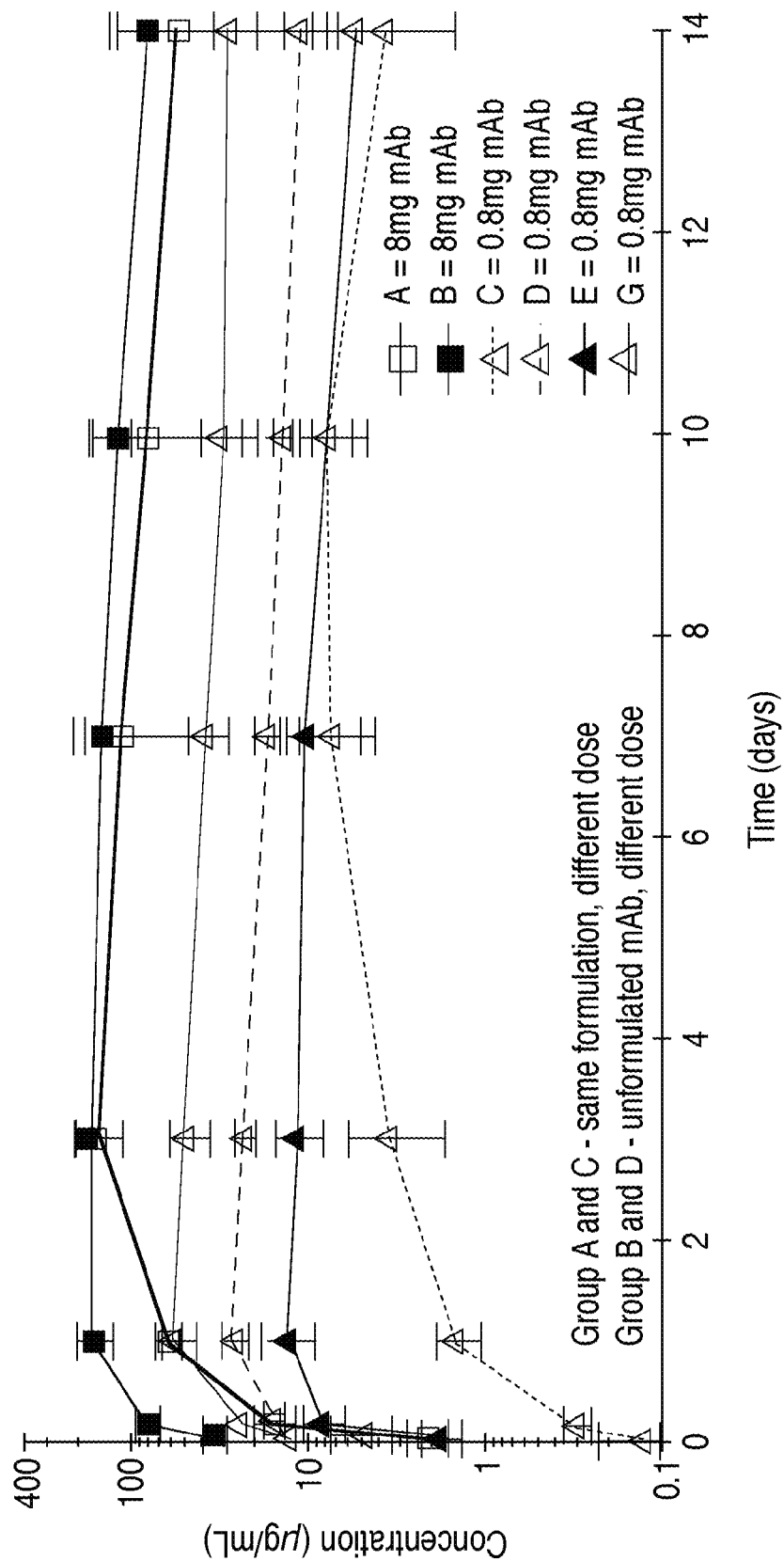

FIG. 12 illustrates plots of serum mAb concentration vs. time after administration of cross-linked compositions according to the disclosed subject matter.

Figure 13A:
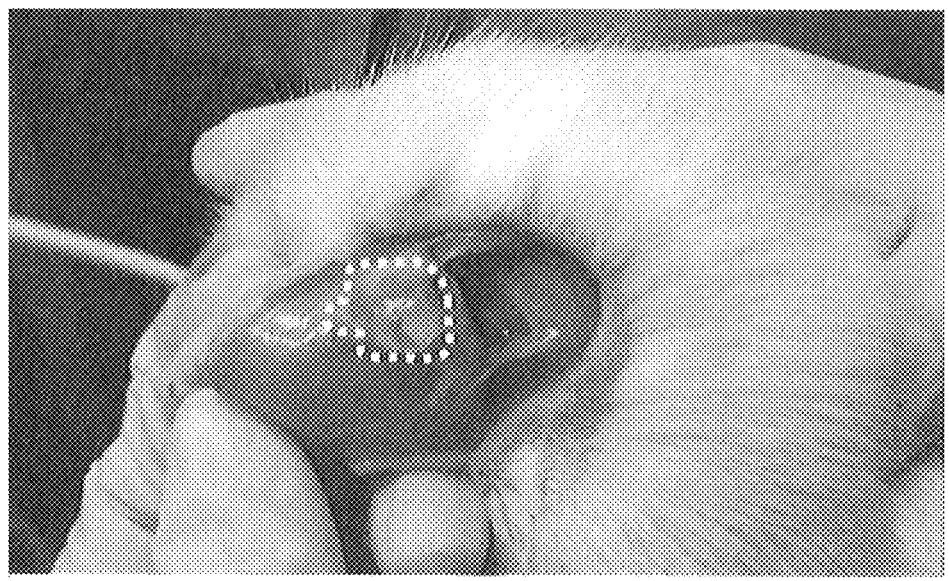
Figure 13B:
Figure 13C:
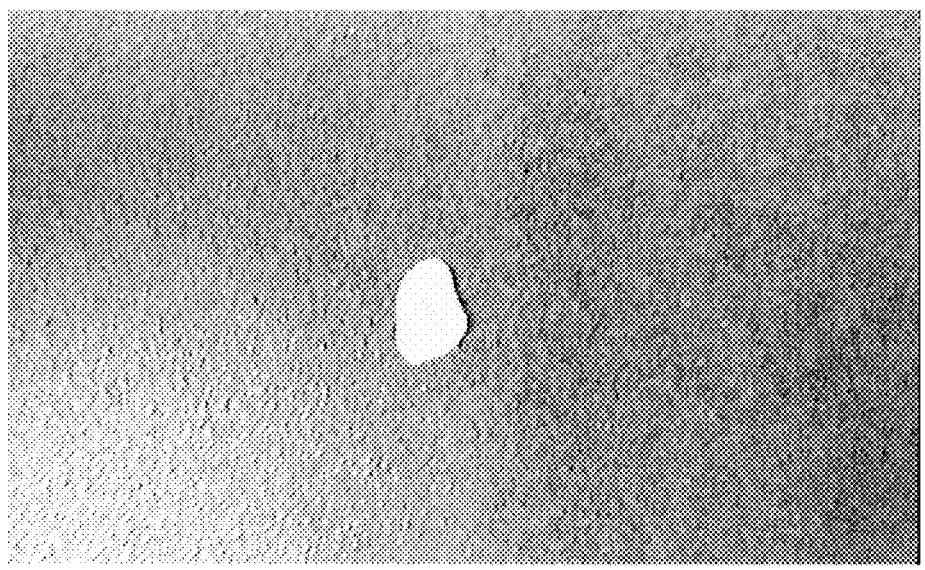

FIG. 13A is a photograph of a cross-linked composition in the intra-articular space of the rat 4 hours after injection. FIG. 13B is a photograph of a cross-linked composition in the intra-articular space of the rat 4 hours after injection. FIG. 13C is a photograph of a cross-linked composition comprising fluorescently tagged mAb after injection and excision from the intra-articular space of a rat hind limb.

Figure 14A:
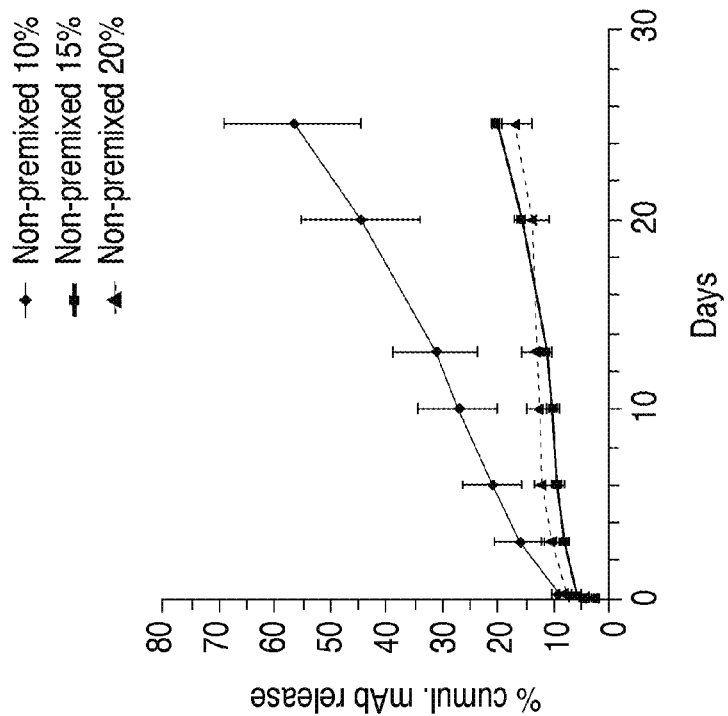
Figure 14B:
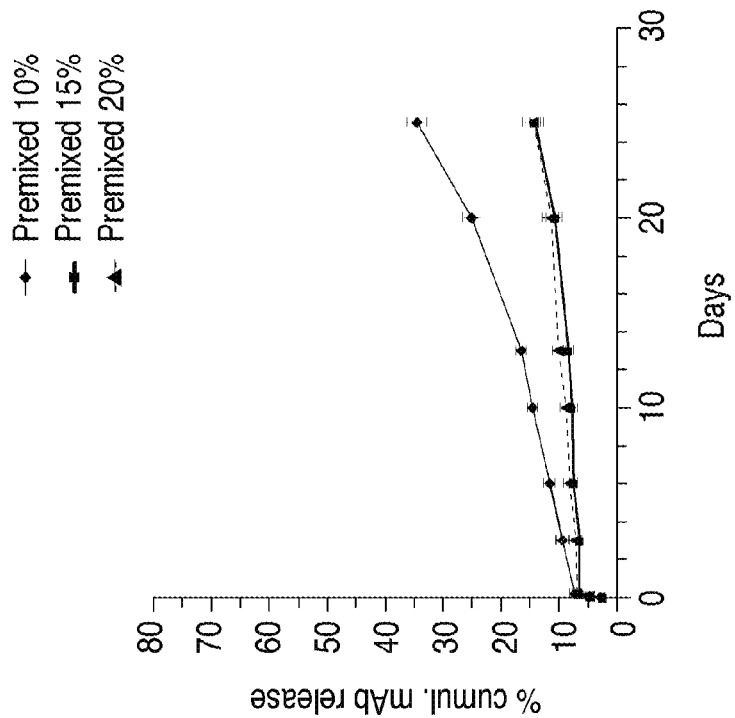
Figure 15A:
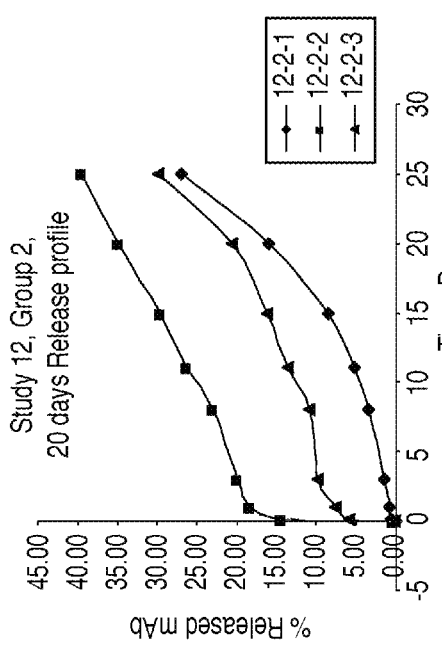
Figure 15B:
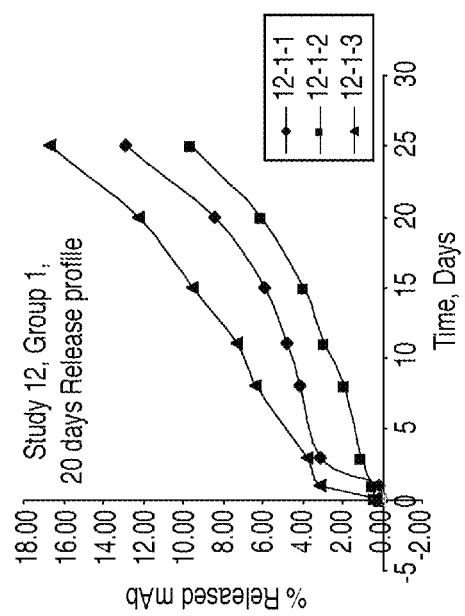
Figure 15C:
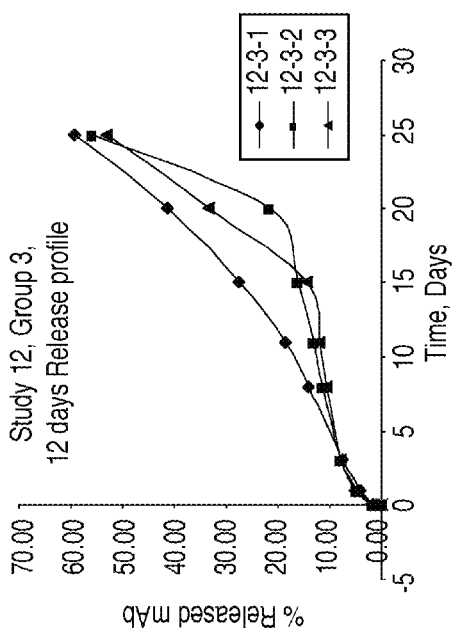
Figure 15E:
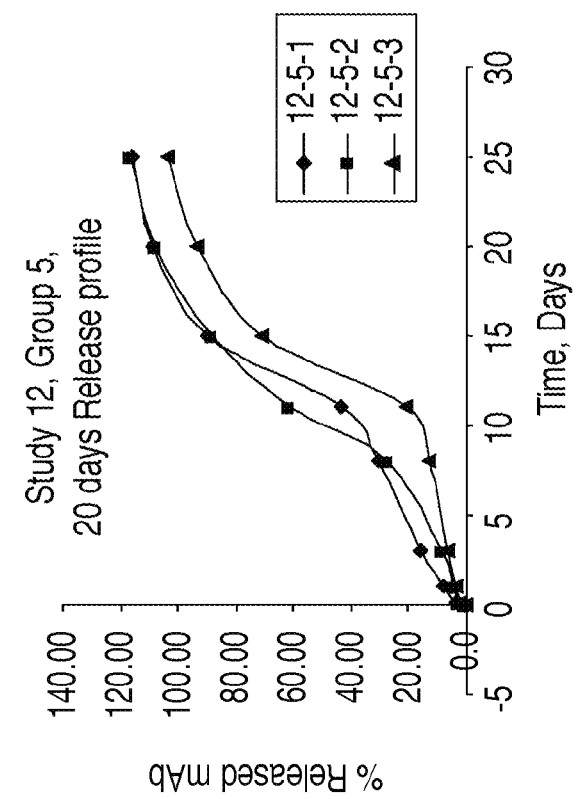
Figure 15D:
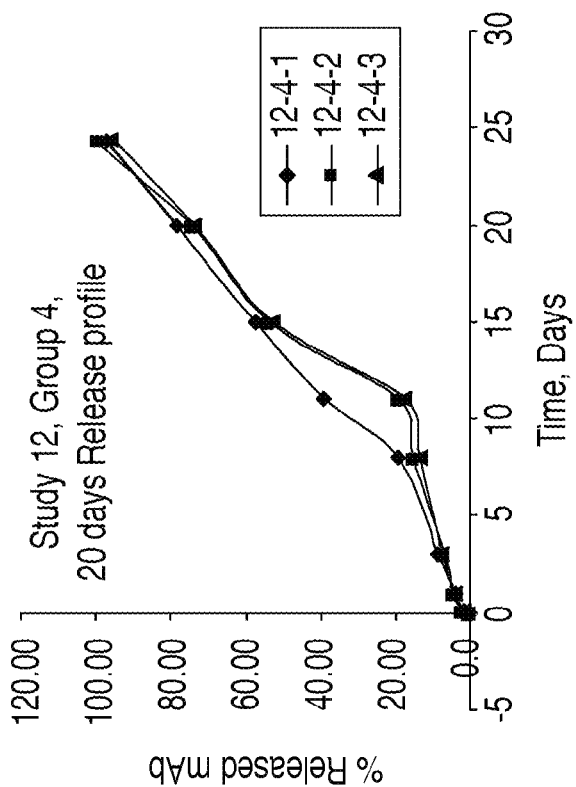
Figure 16E:
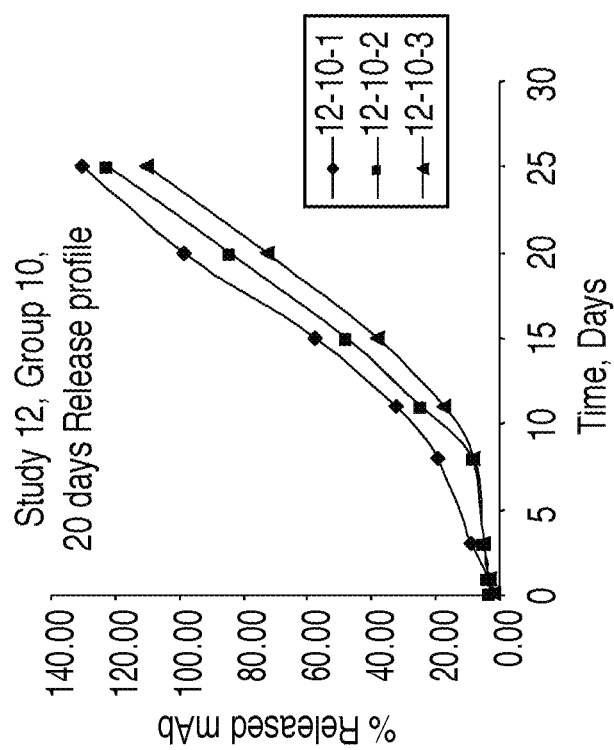
Figure 16D:
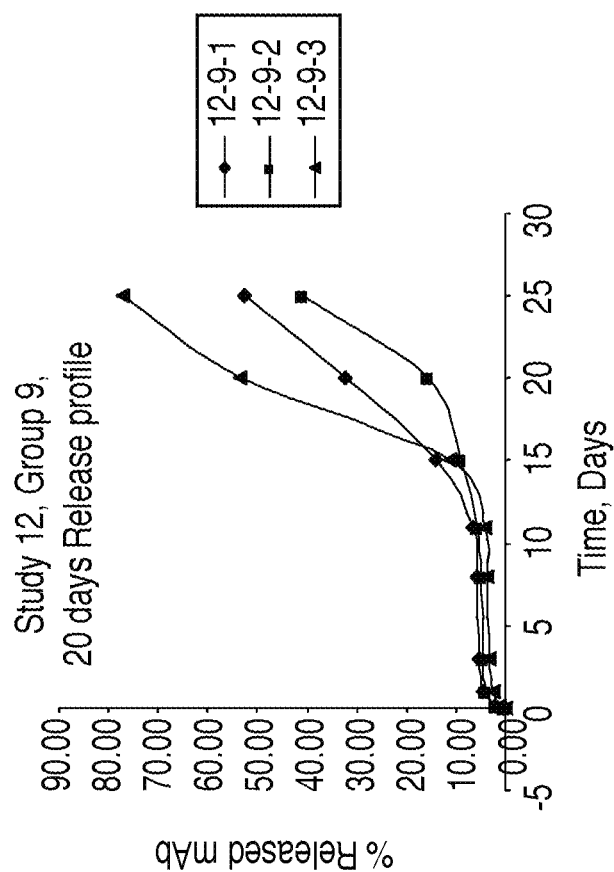

FIG. 14A and FIG. 14B are plots of average in vitro mAb release over time from various cross-linked premixed and non-premixed compositions, respectively.

FIG. 15A, FIG. 15B, FIG. 15C, FIG. 15D and FIG. 15E are plots of in vitro mAb release over time from individual cross-linked compositions which correspond to the average values plotted in FIG. 14A.

FIG. 16A, FIG. 16B, FIG. 16C, FIG. 16D and FIG. 16E are plots of in vitro mAb release over time from individual cross-linked compositions which correspond to the average values plotted in FIG. 12B.

Figure 17A:
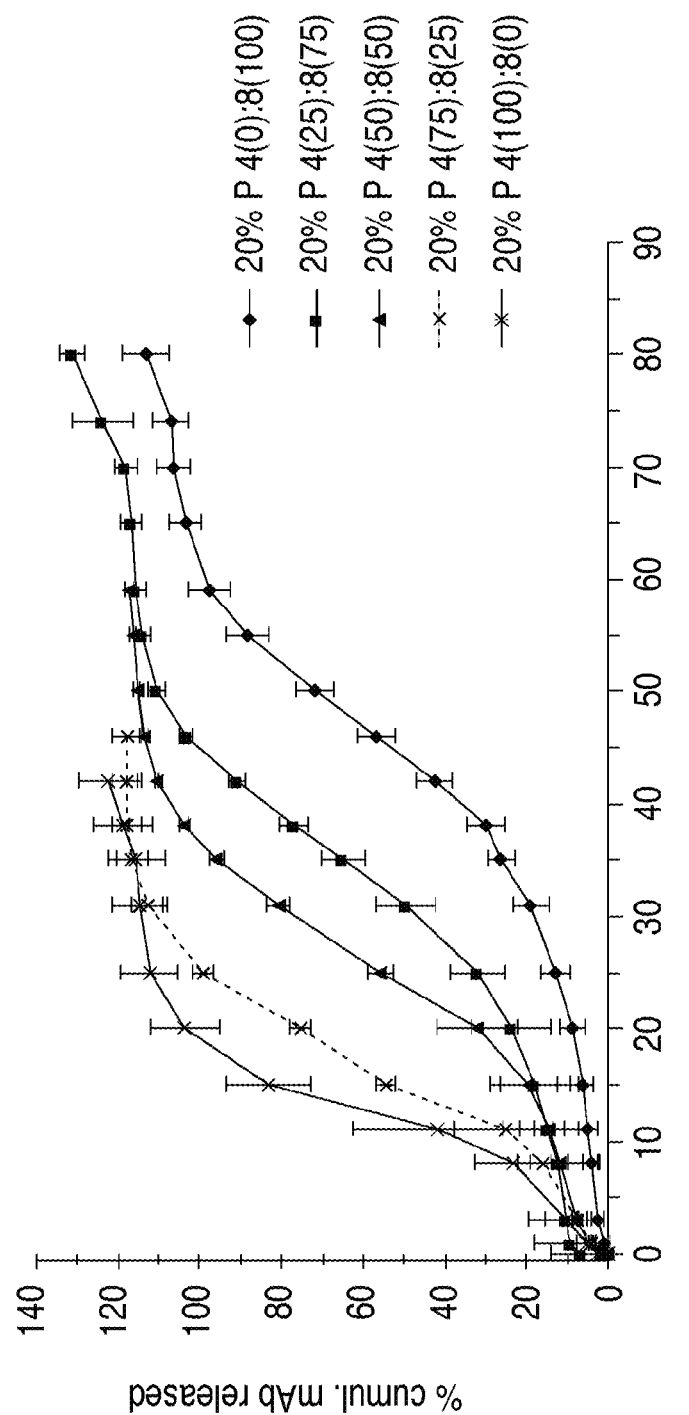
Figure 17B:
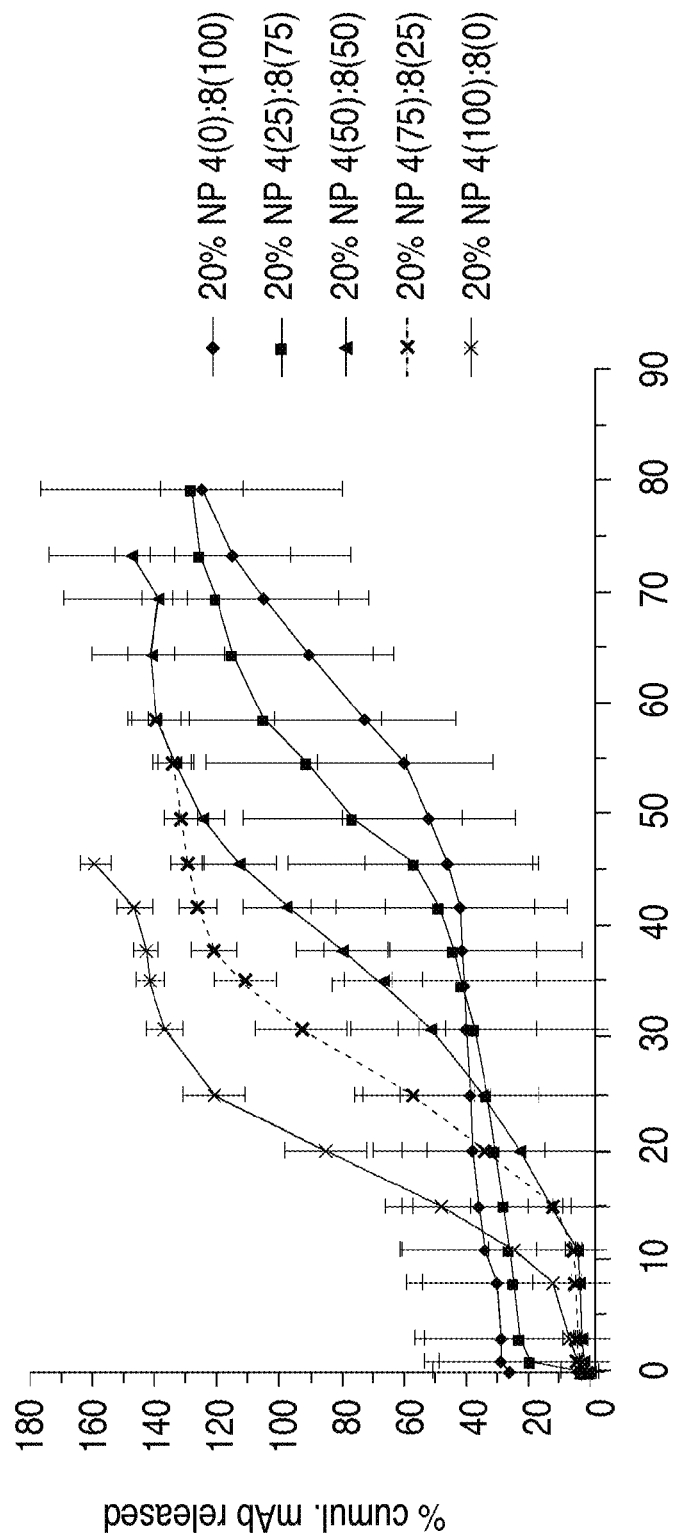
Figure 17C:
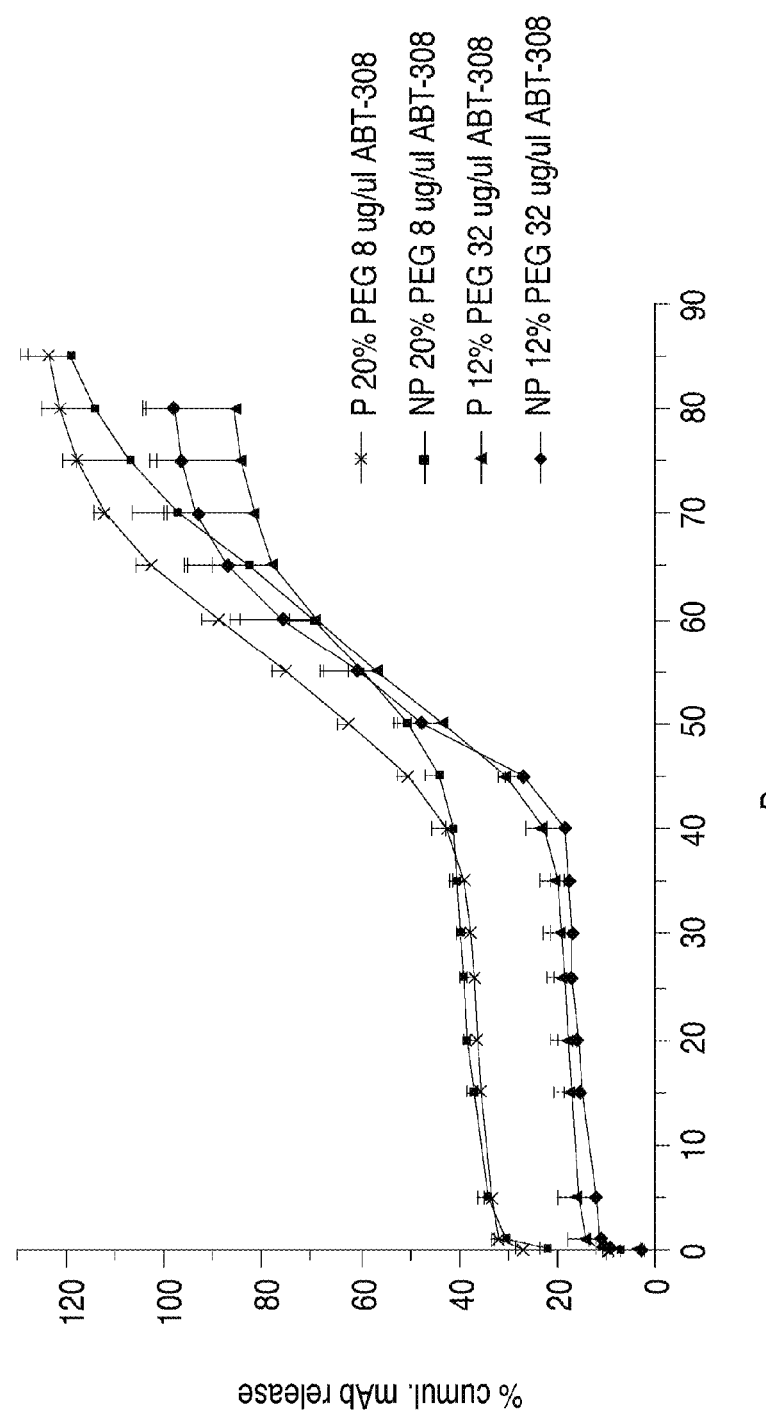

FIG. 17A, FIG. 17B, and FIG. 17C depict additional in vitro mAb release over time experiments from various cross-linked compositions according to the disclosed subject matter.

Figures 18A, 18B:
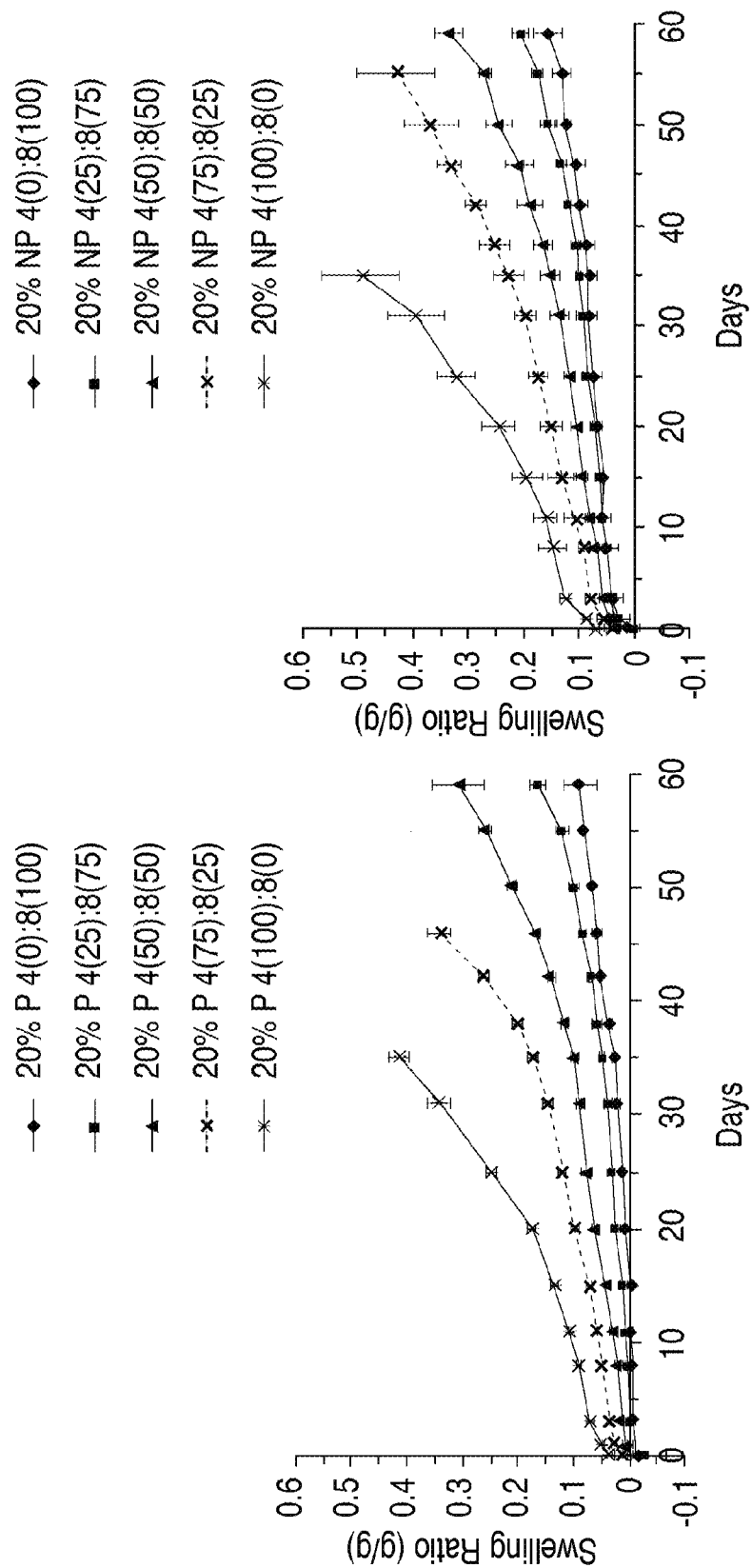

FIG. 18A and FIG. 18B depict plots of swelling ratios over time for various cross-linked compositions according to the disclosed subject matter.

Figure 19:
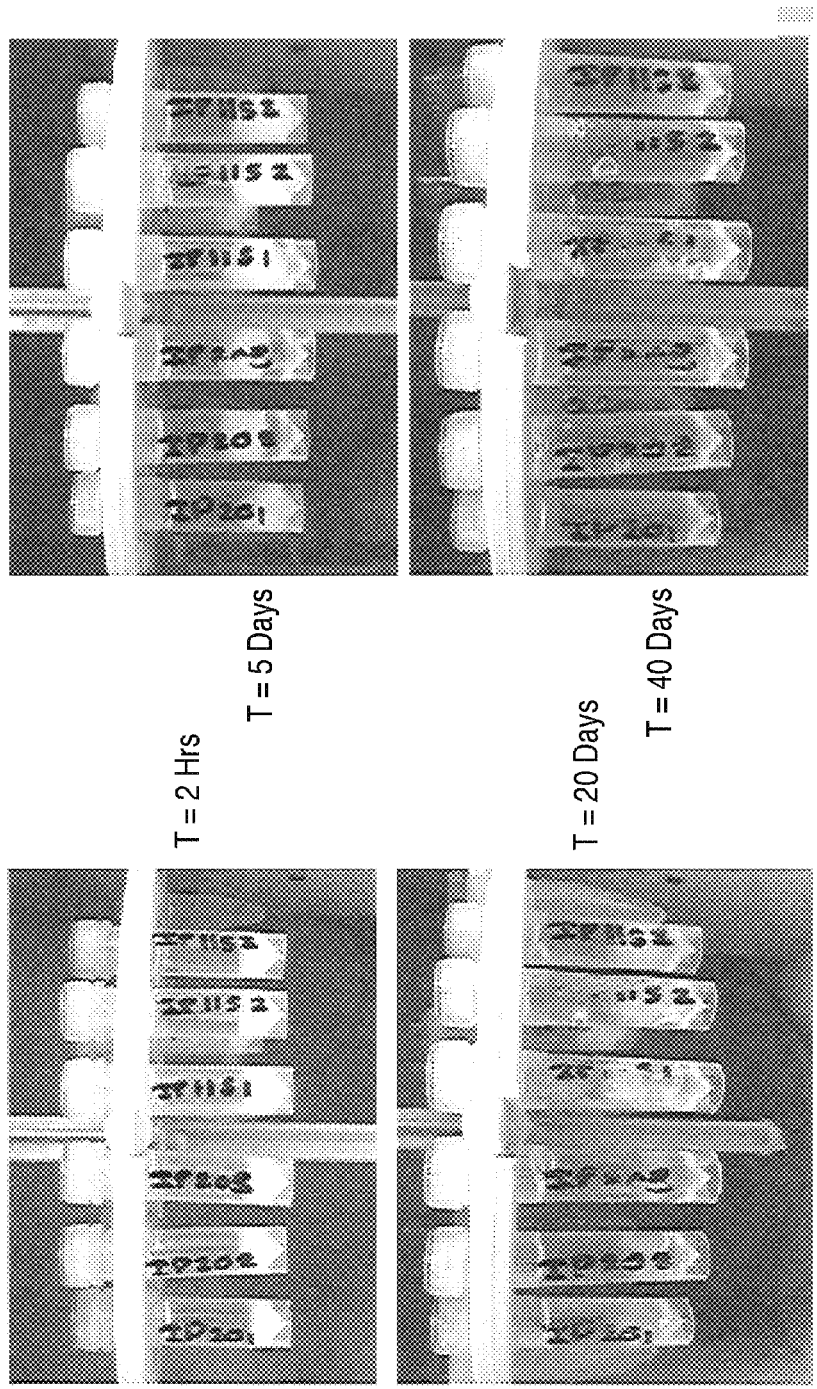

FIG. 19 is a digital photograph of visual swelling of various cross-linked compositions according to the disclosed subject matter over time.

Figure 20:
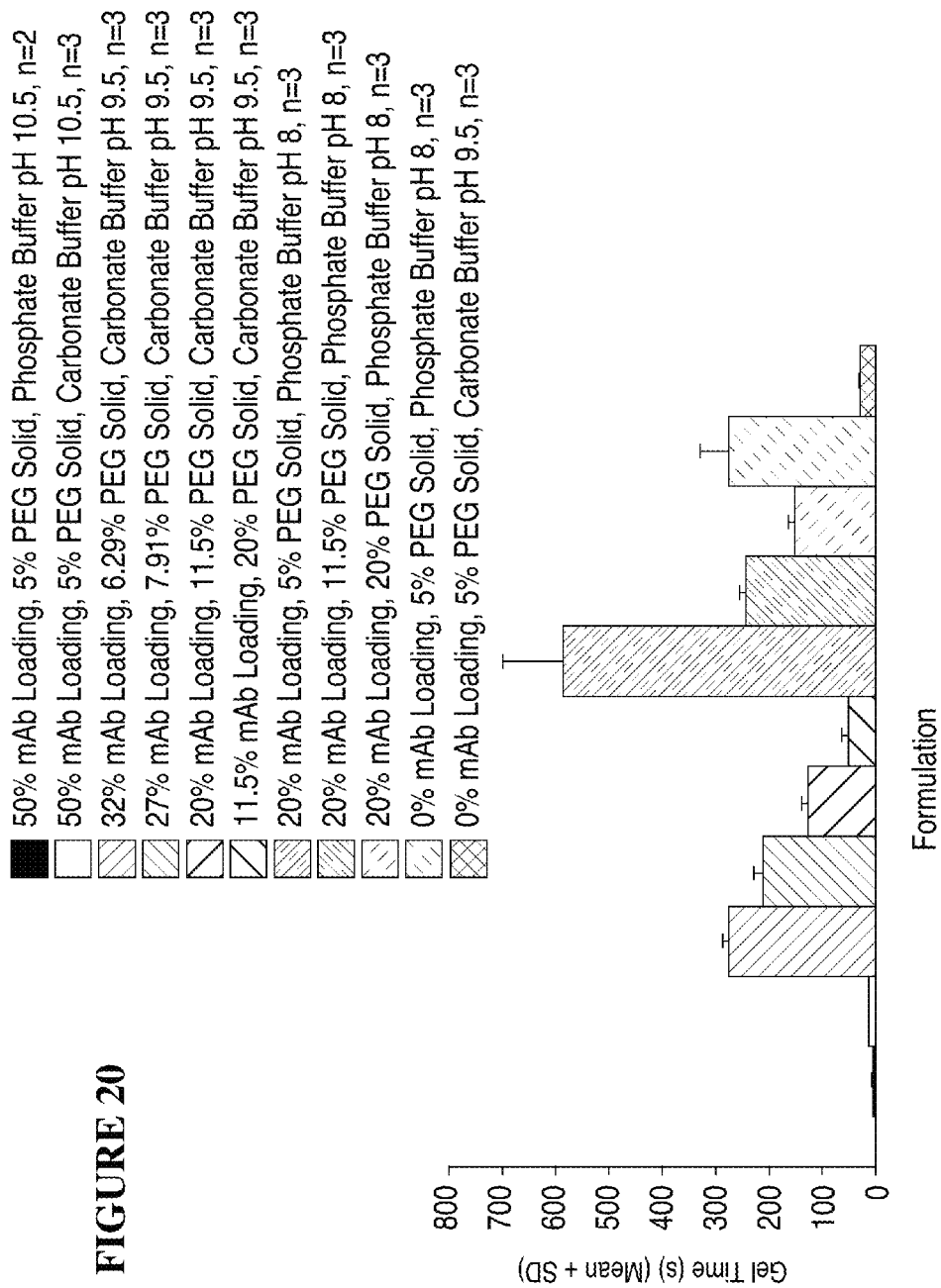

FIG. 20 is a graph of time to crosslinking of various cross-linked compositions according to the disclosed subject matter.

Figure 21:
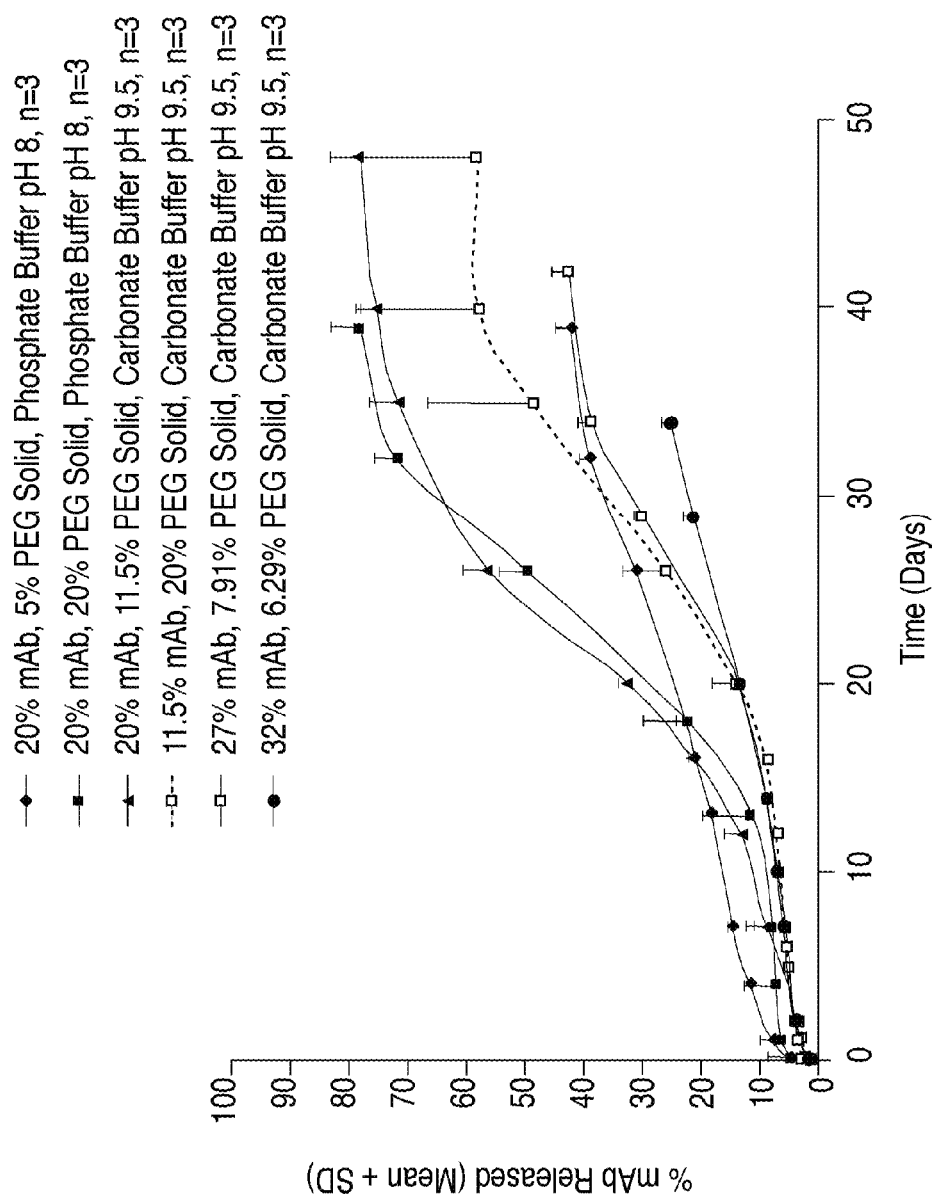

FIG. 21 is a plot of in vitro mAb release over time from various cross-linked compositions according to the disclosed subject matter.

Figure 22:
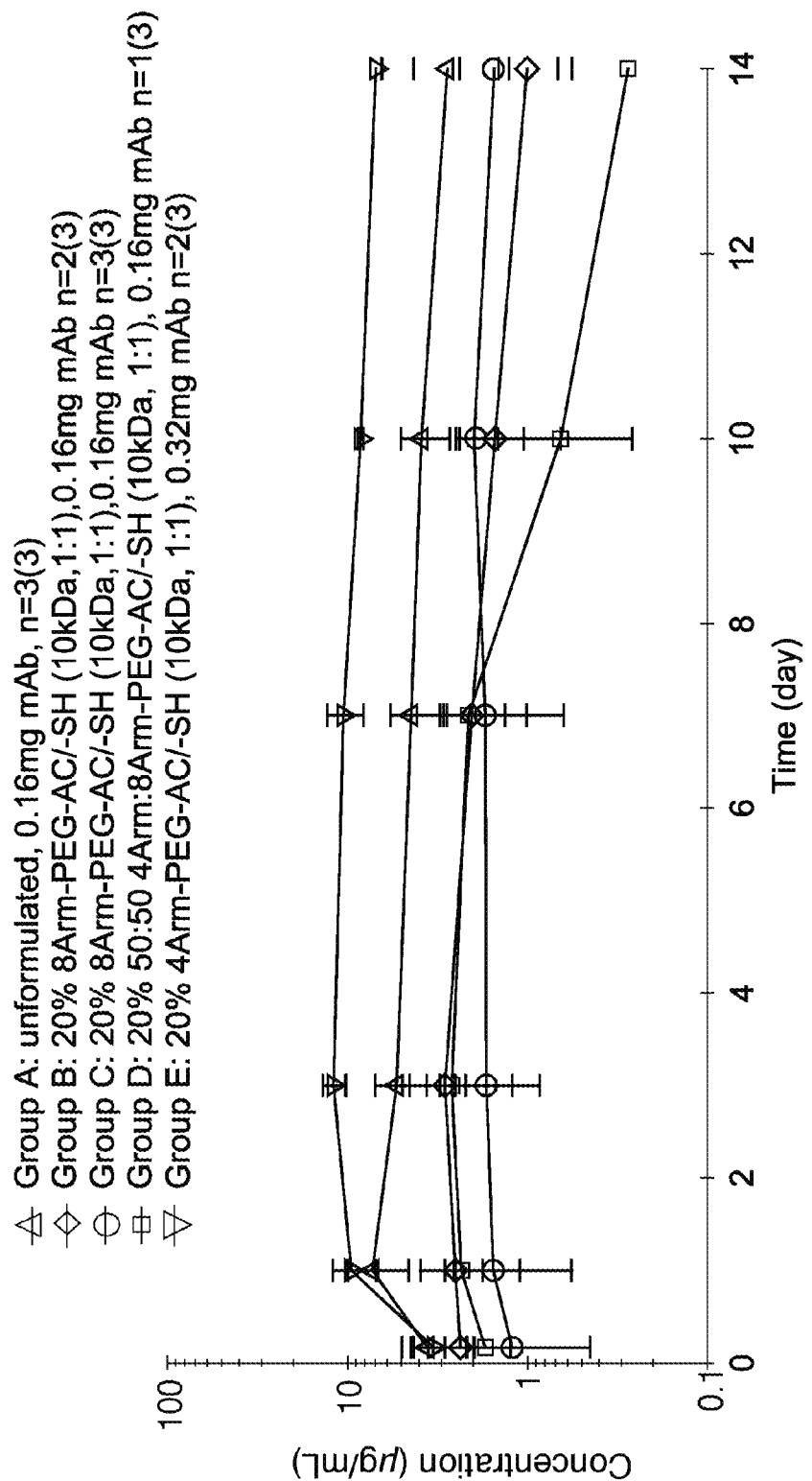
Figure 23A:
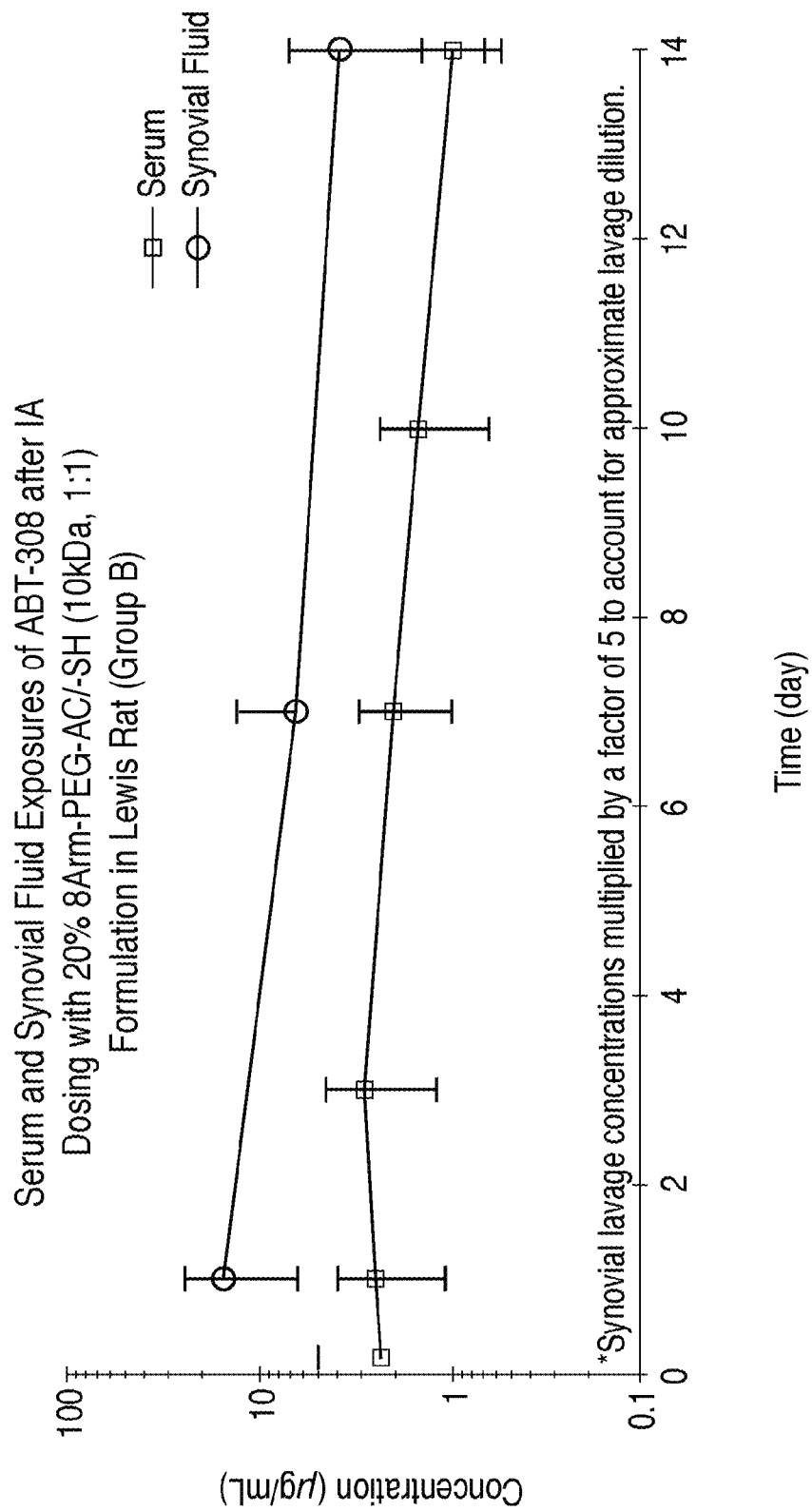
Figure 23B:
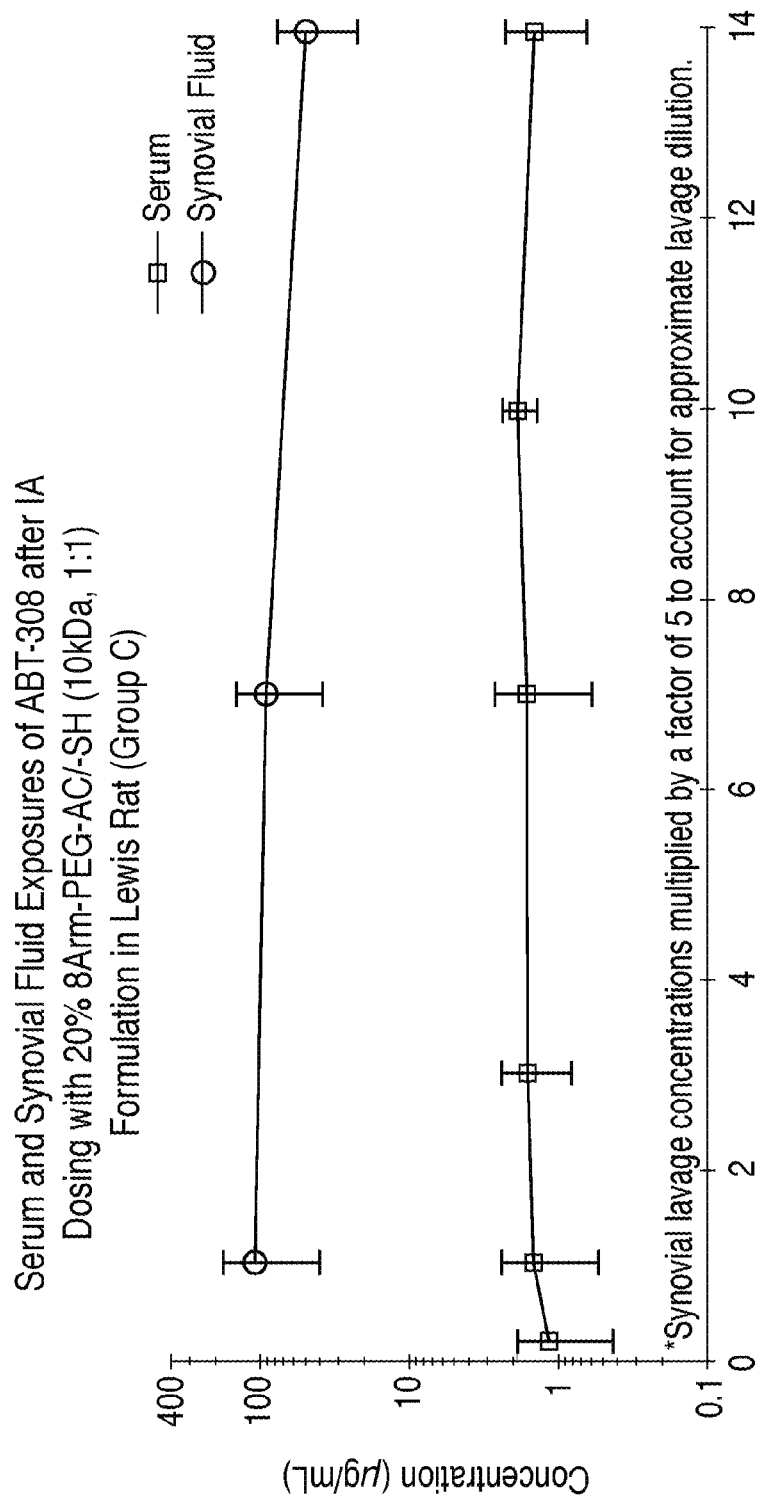
Figure 23C:
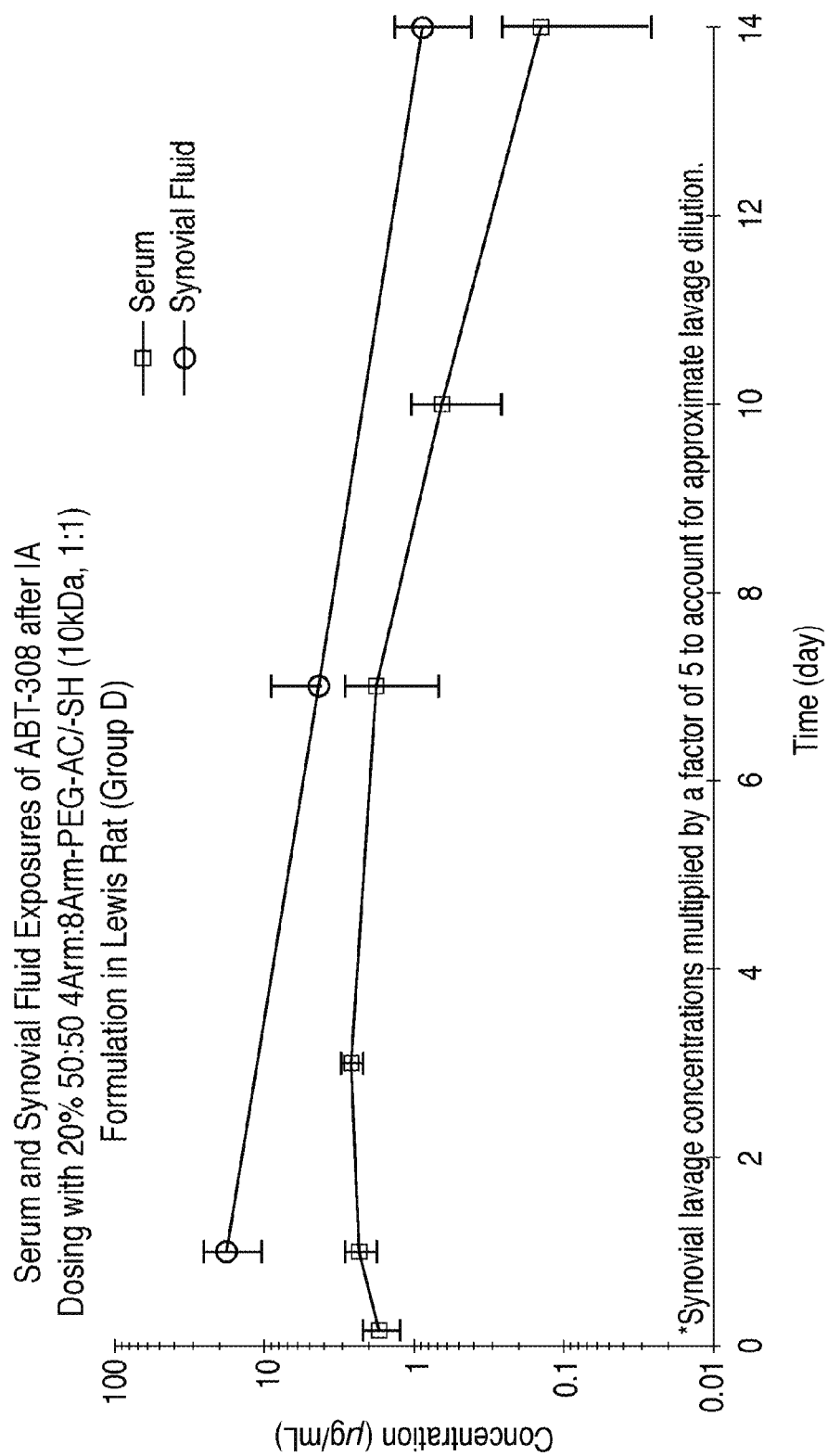
Figure 23D:
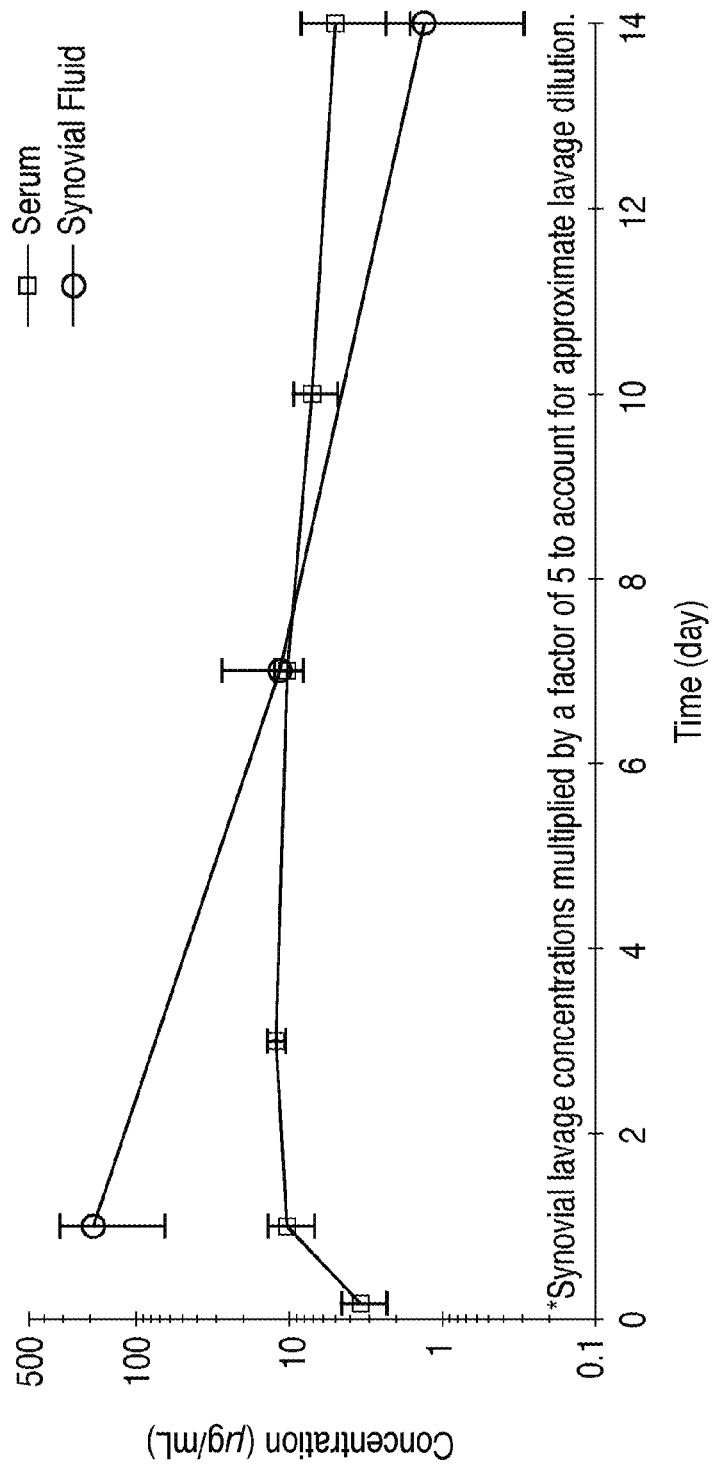
Figure 23E:
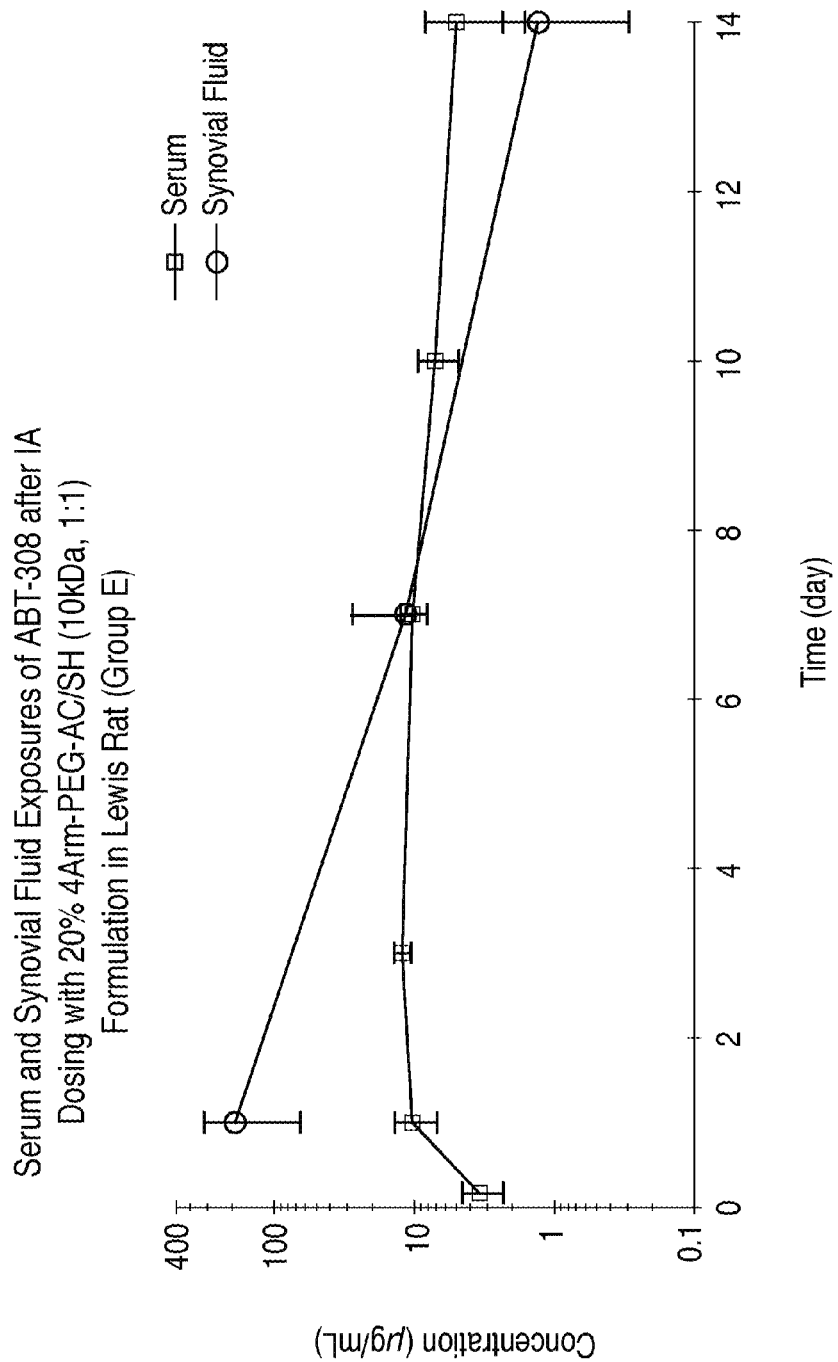
Figure 24A:
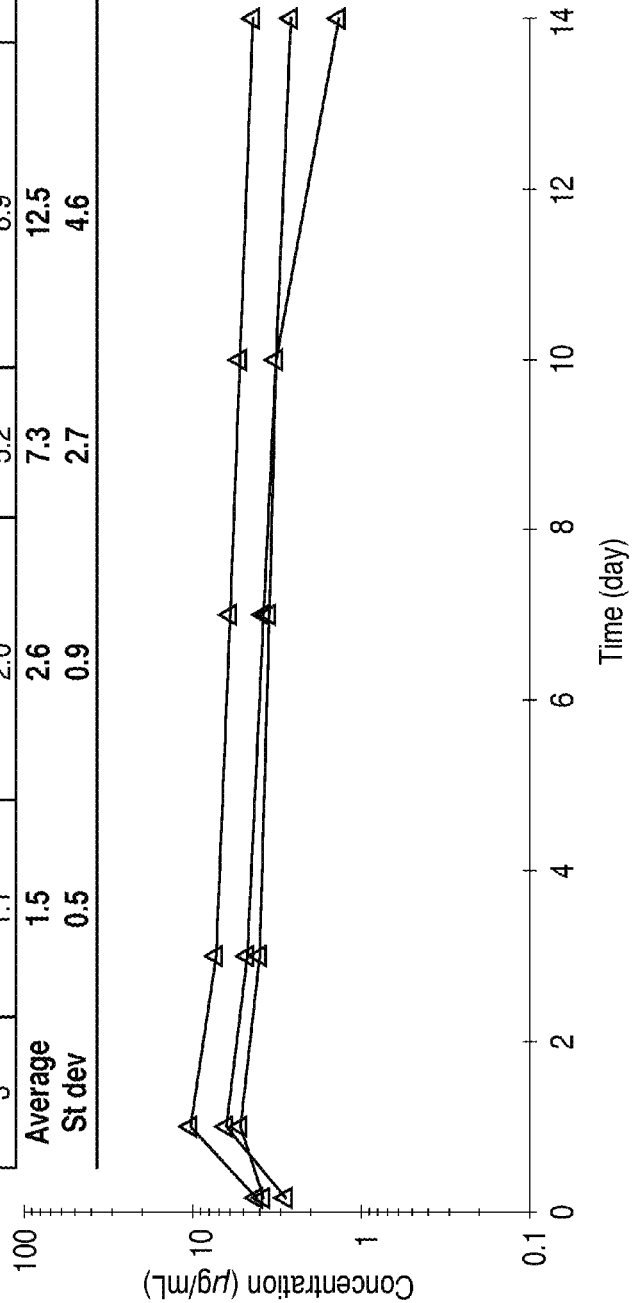
Figure 24B:
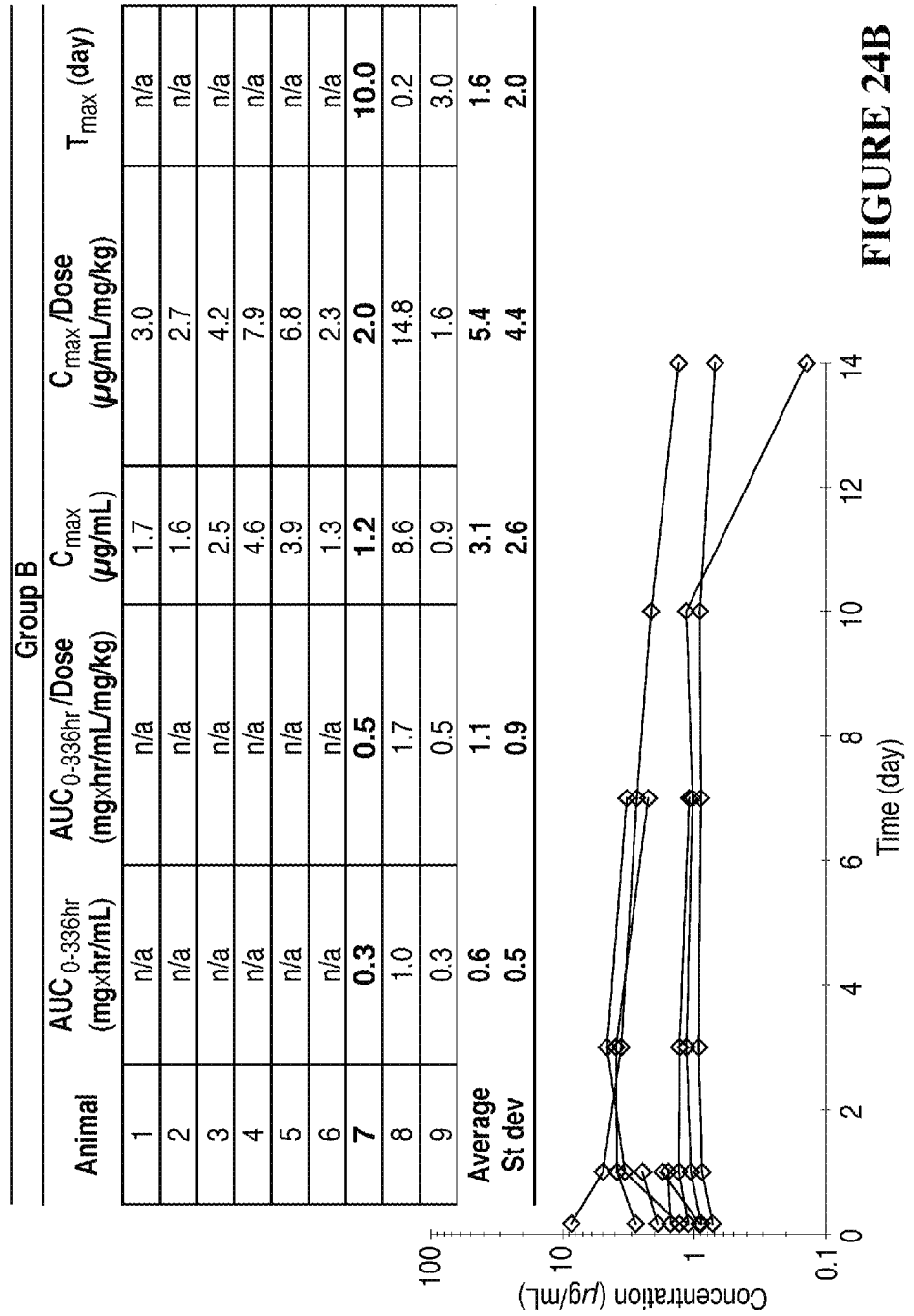
Figure 24C:
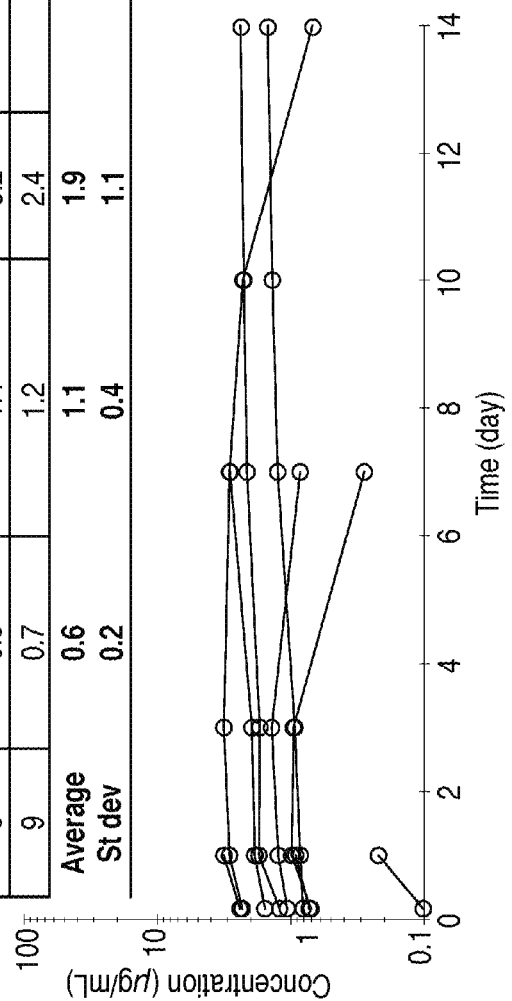
Figure 24D:
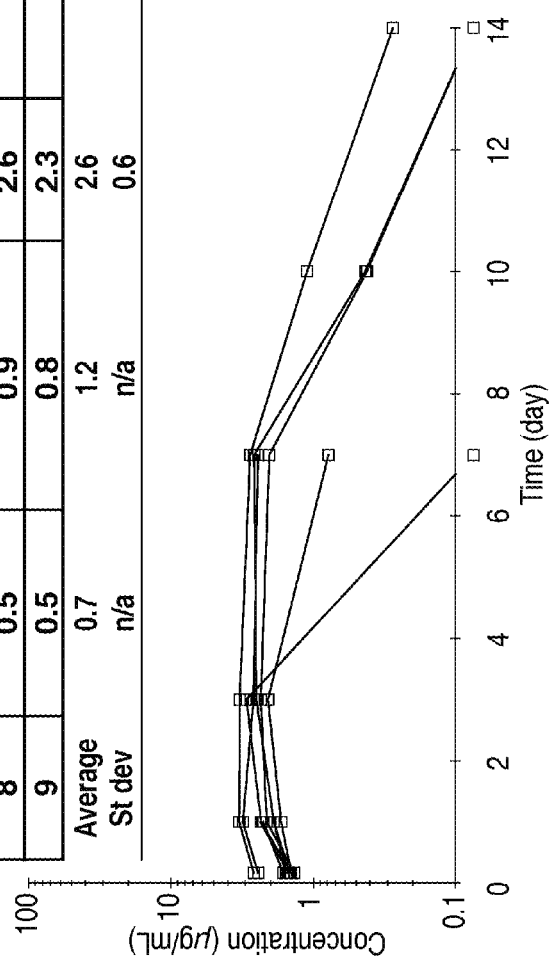
Figure 24E:
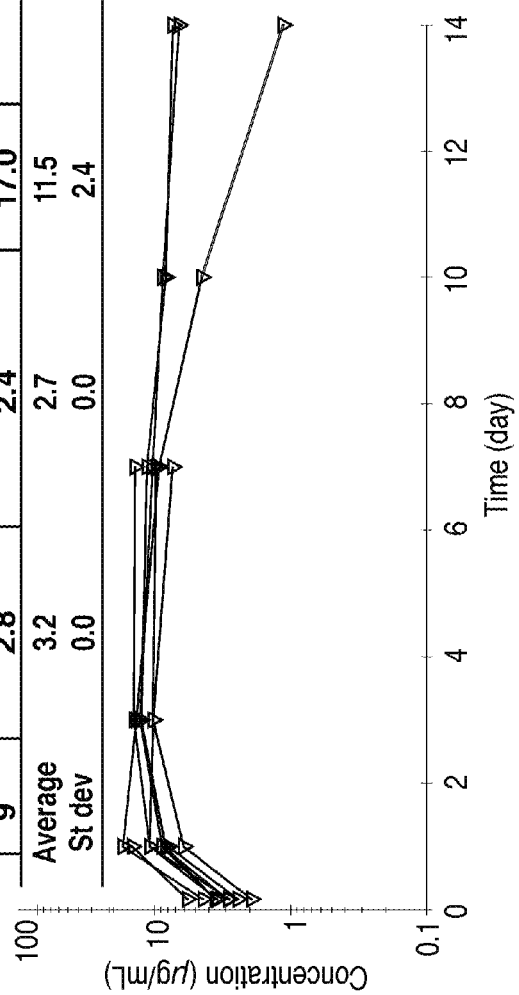

FIG. 22 is a plot of serum concentrations of mAb after administration of cross-linked compositions according to the disclosed subject matter or administration of unformulated antibody.

FIG. 23A, FIG. 23B, FIG. 23C, FIG. 23D and FIG. 23E are plots of average serum concentration over time for treatment groups B, C, D and E respectively as depicted in FIG. 22.

FIG. 24A, FIG. 24B, FIG. 24C, FIG. 24D and FIG. 24E are plots of serum concentration over time for individual animals for treatment groups A-E respectively as depicted in FIG. 22.

Figure 25:
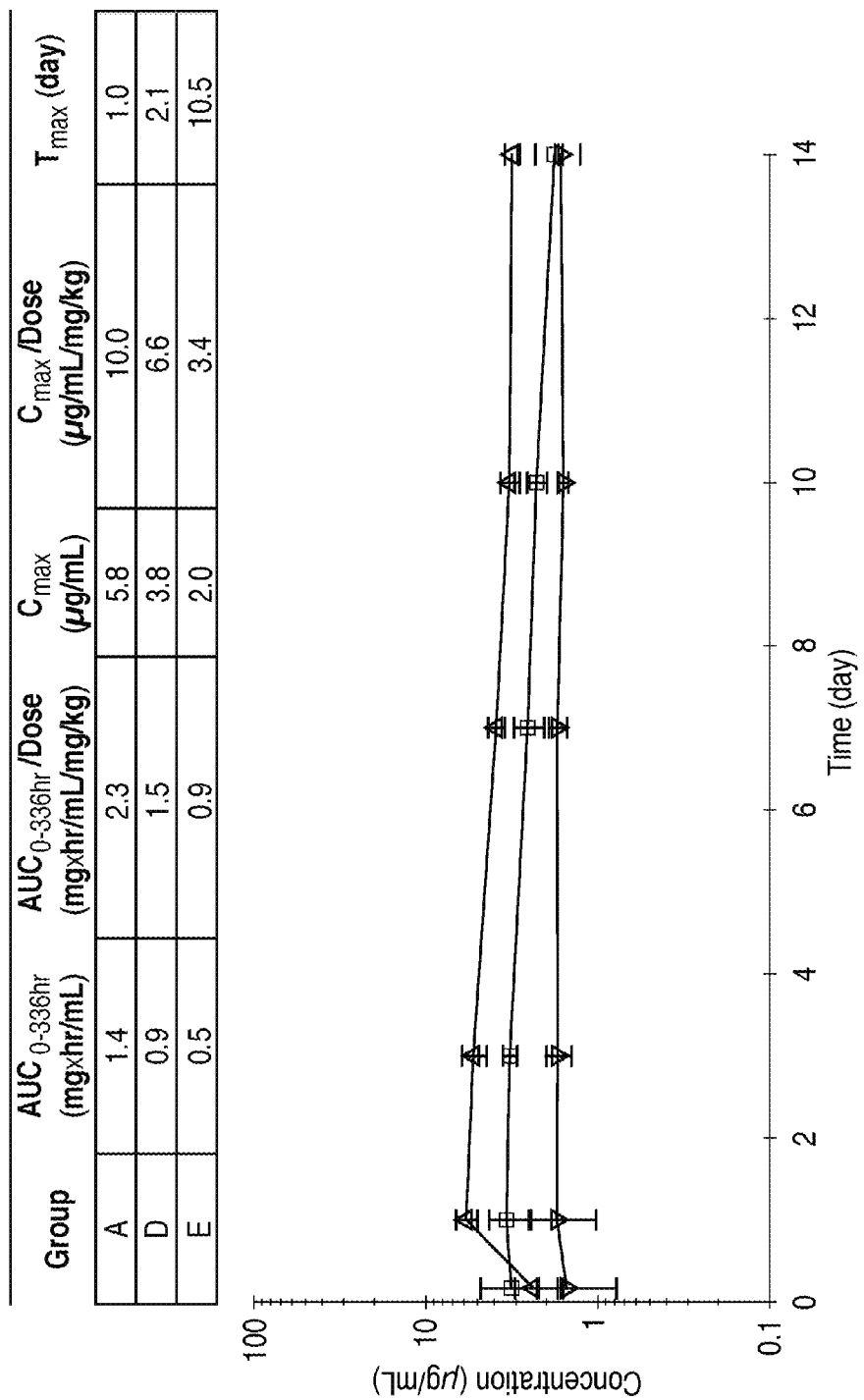

FIG. 25 is a plot of serum concentrations of mAb after administration of cross-linked compositions according to the disclosed subject matter or after administration of unformulated antibody.

Figure 26A:
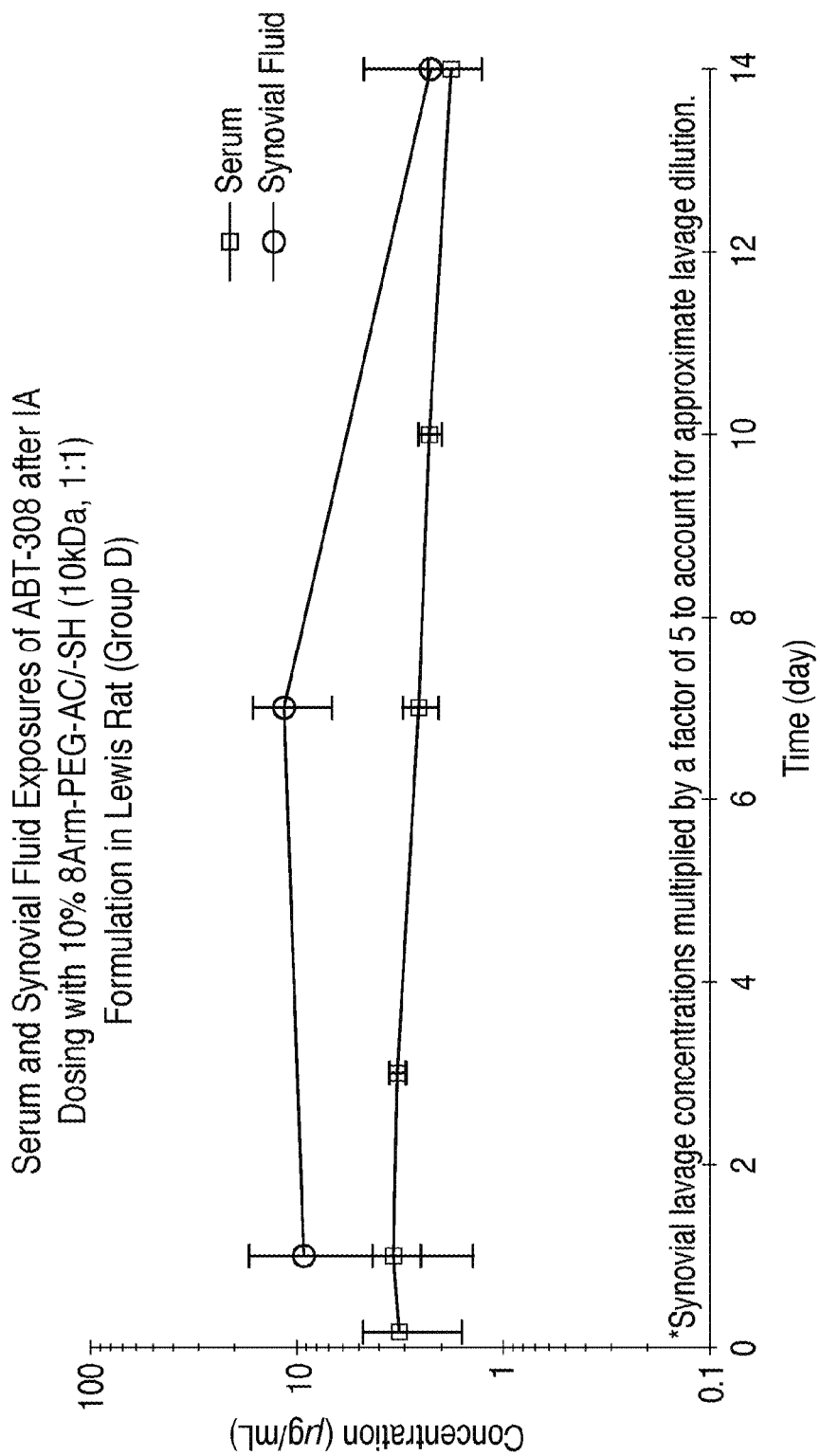
Figure 26B:
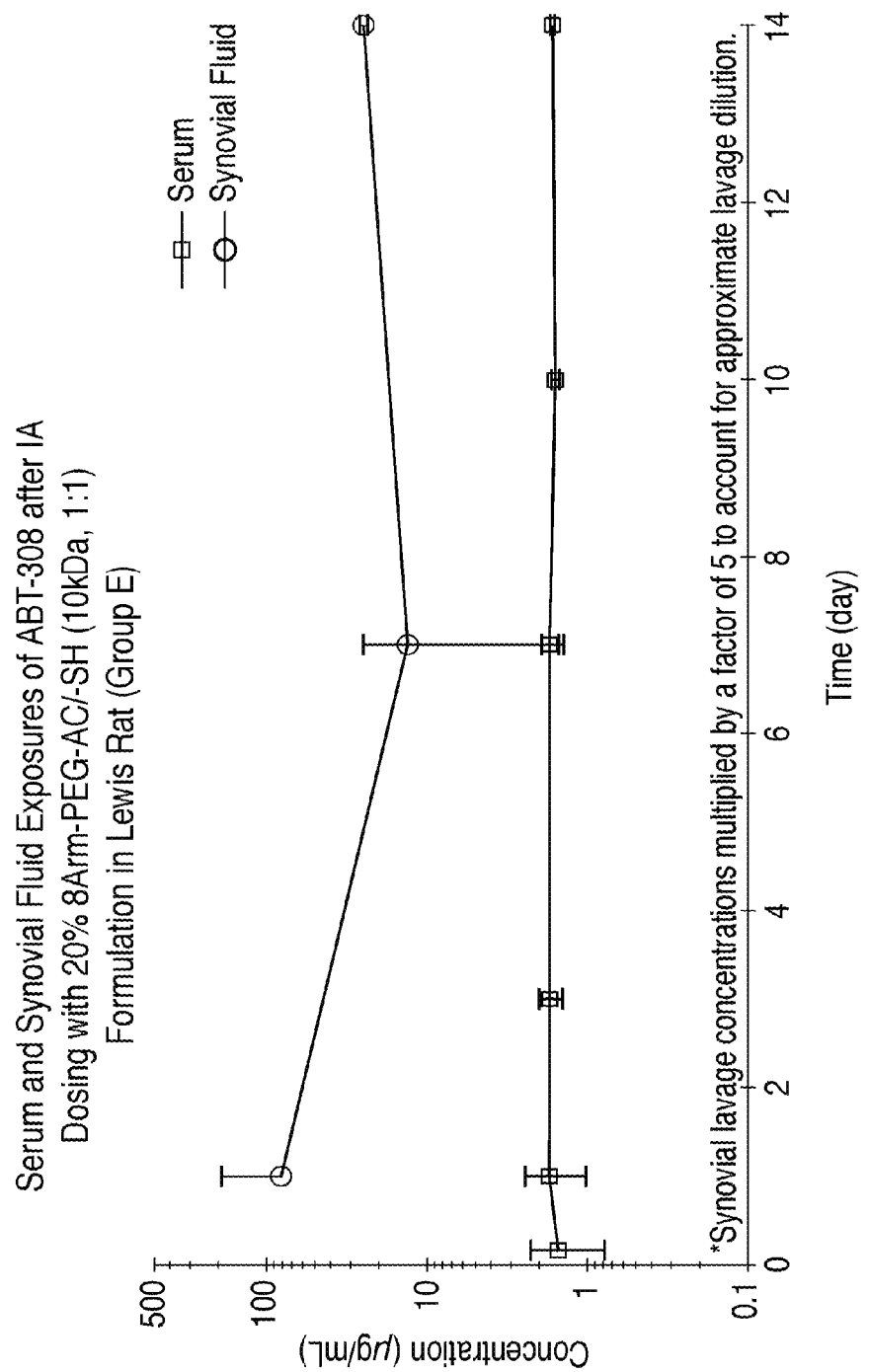

FIG. 26A and FIG. 26B are plots of serum concentration over time for treatment groups D and E, respectively, as depicted in FIG. 24.

Figure 27A:
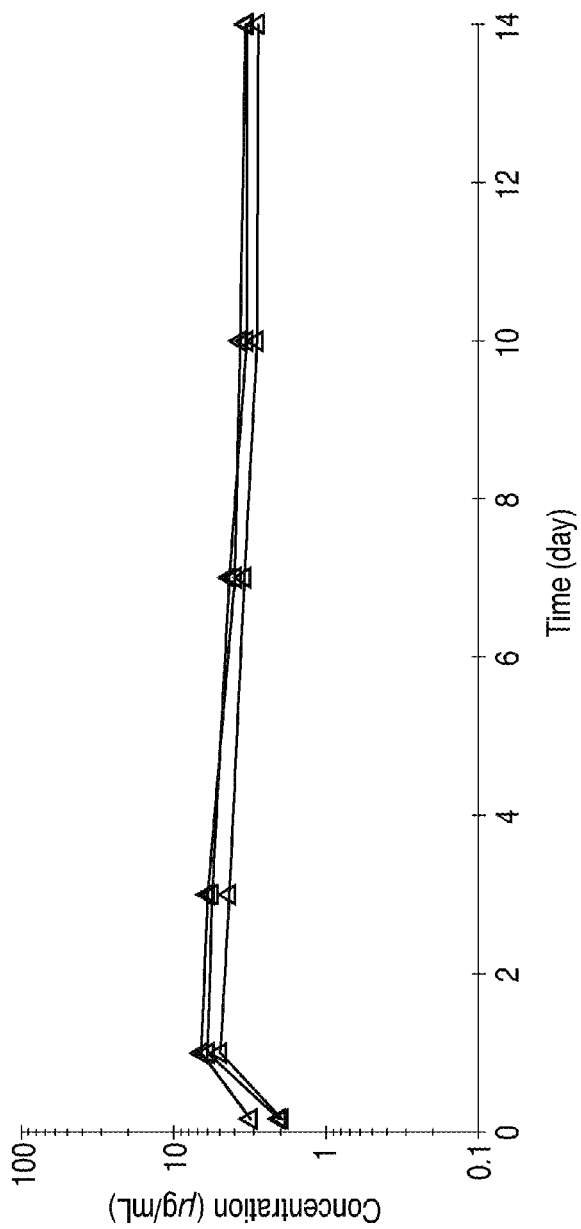
Figure 27B:
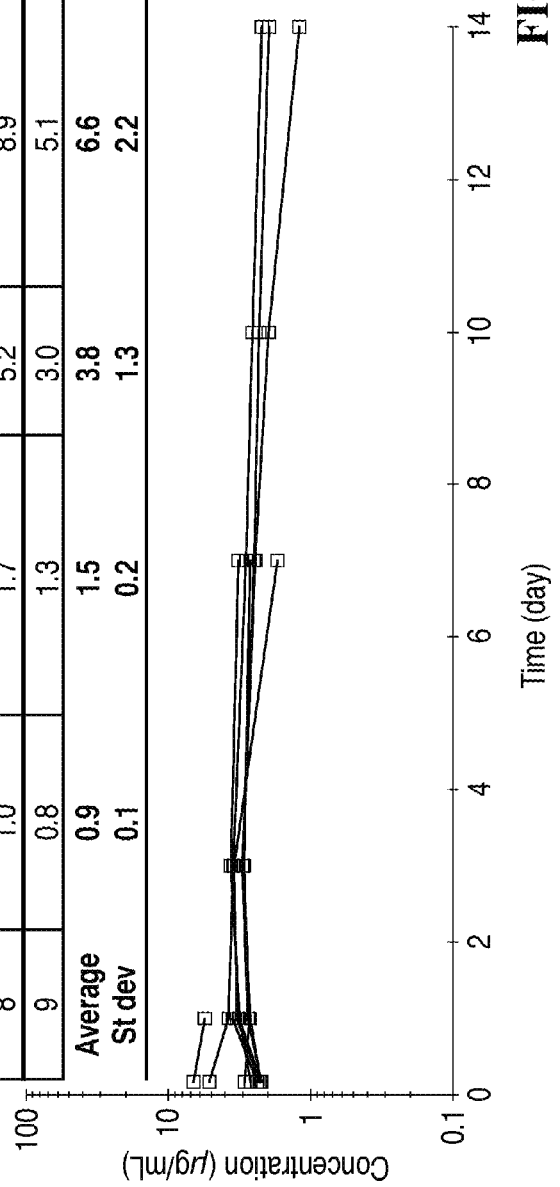
Figure 27C:
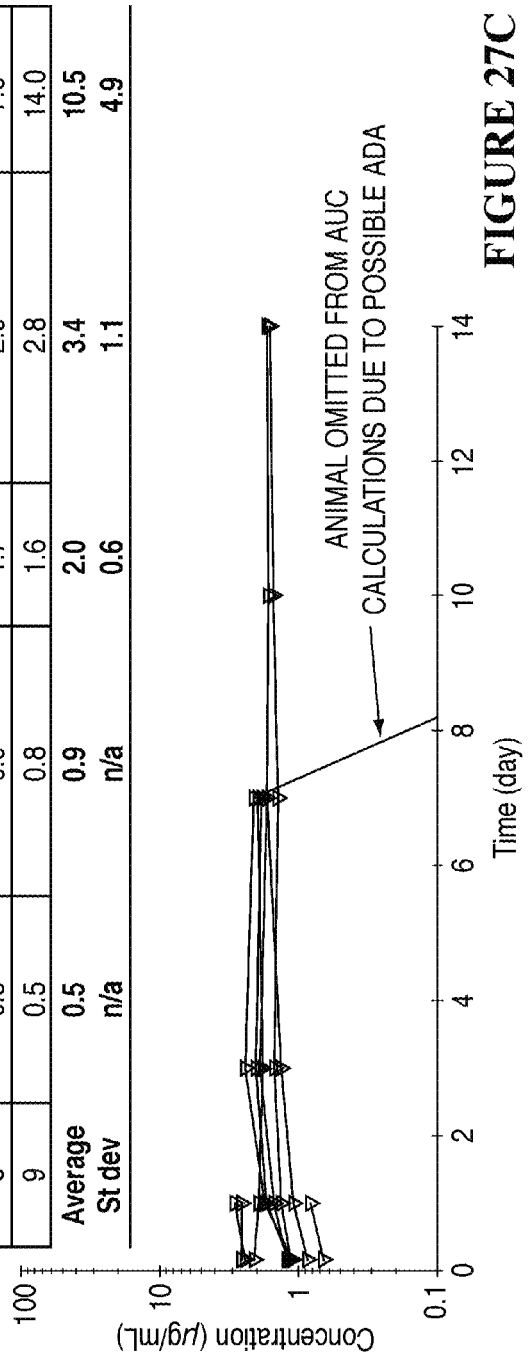

FIG. 27A, FIG. 27B, and FIG. 27C are plots of serum concentration over time for individual animals in treatment groups A, D and E respectively as depicted in FIG. 25.

Figure 28:
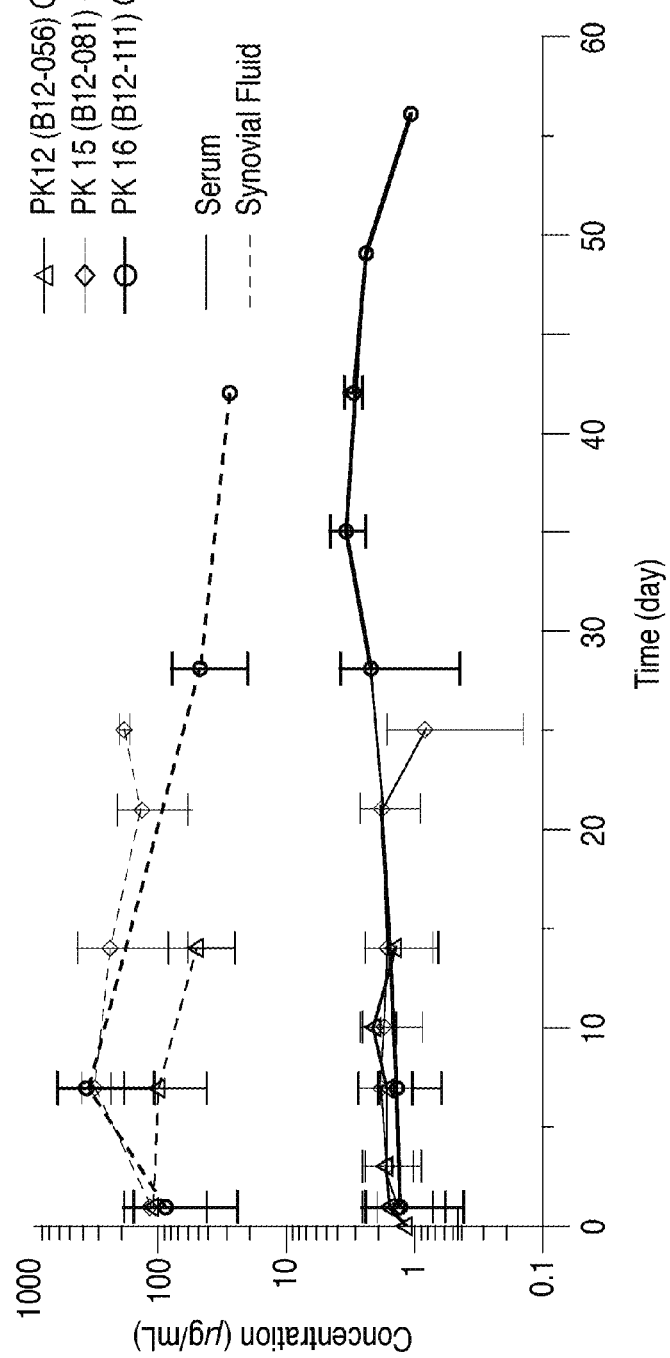

FIG. 28 is a plot of serum and synovial fluid exposures over time for selected treatment groups from separate experiments.

Figure 29:
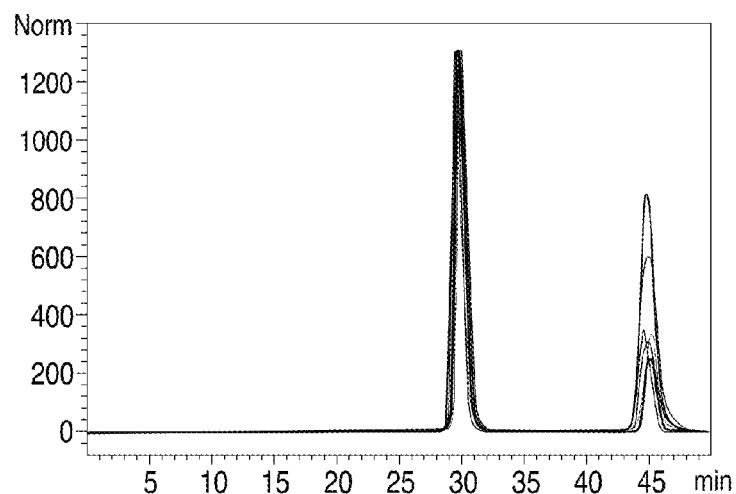

FIG. 29 is size exclusion chromatography data for mAb released in vitro from a cross-linked composition according to the disclosed subject matter.

Figure 30:
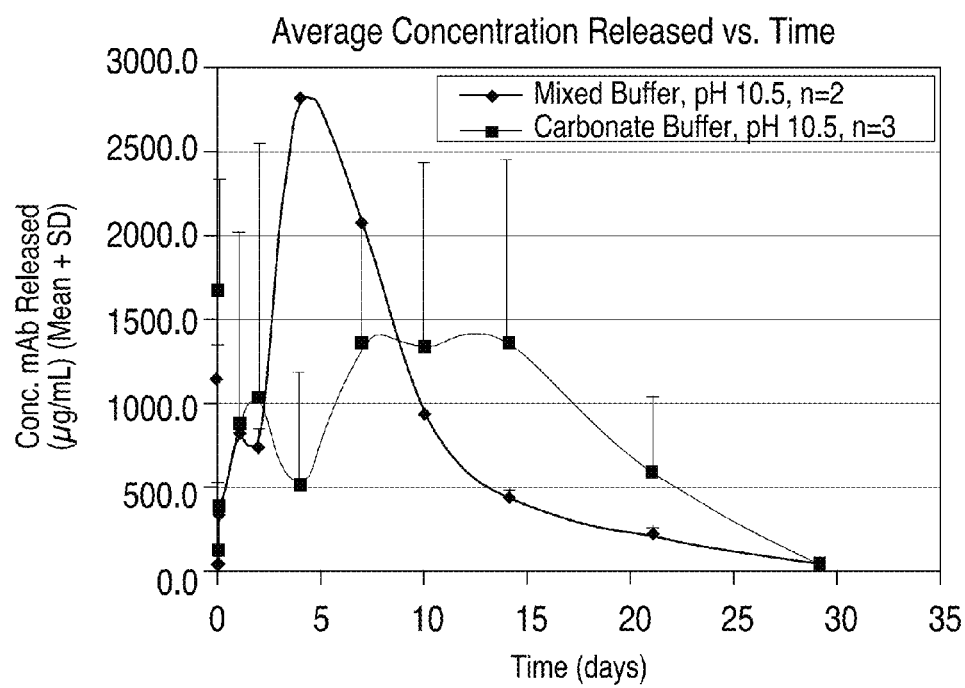
Figure 31:
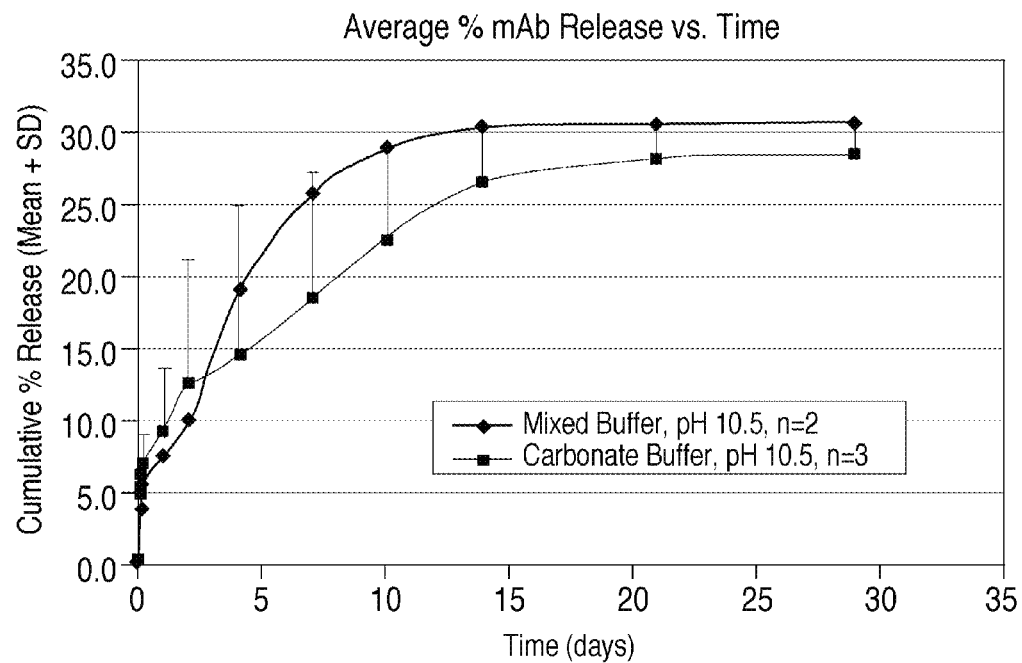

FIG. 30 is a plot of mAb release over time from a cross-linked composition according to the disclosed subject matter, FIG. 31 is a plot of mAb release from a cross-linked composition according to the disclosed subject matter normalized to initial concentration of mAb administered.

Figure 32:
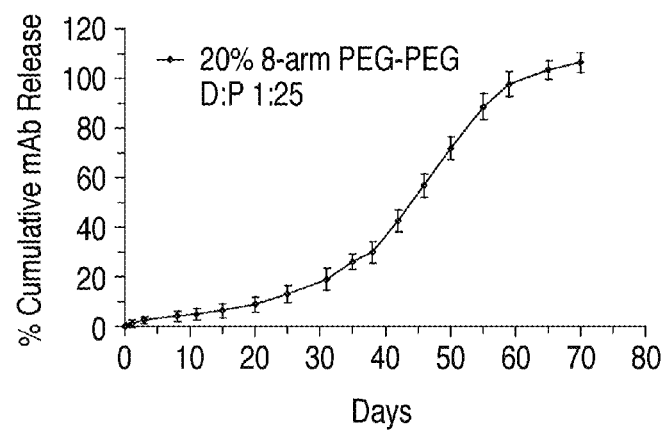

FIG. 32 is a plot of mAb release over time from a cross-linked composition according to the disclosed subject matter.

Figure 33:
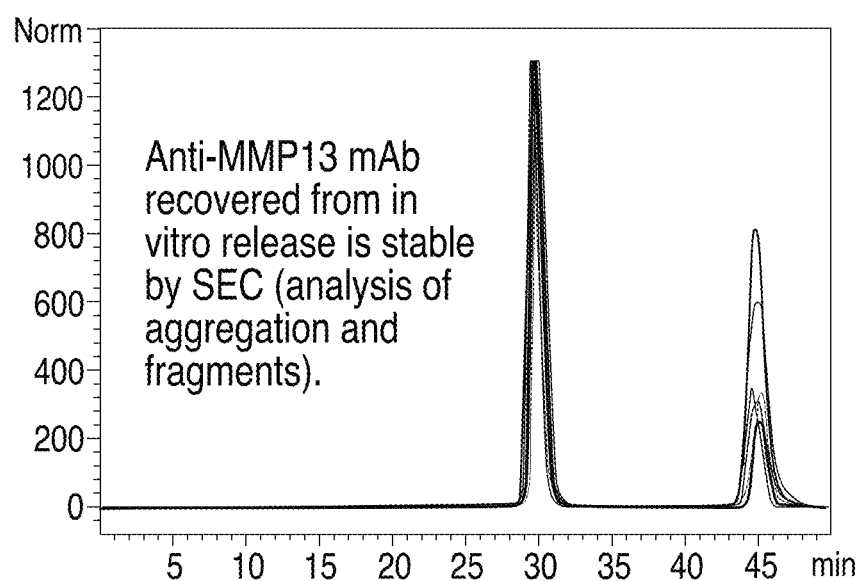

FIG. 33 is an illustration of size exclusion chromatography results on anti-MMP mAb released from a cross-linked composition according to the disclosed subject matter.

4. DETAILED DESCRIPTION OF THE INVENTION

Reference will now be made in detail to embodiments of the disclosed subject matter. Methods and kits will be described in connection with a detailed description of particular embodiments of the formulations of the disclosed subject matter.

Figure 1:
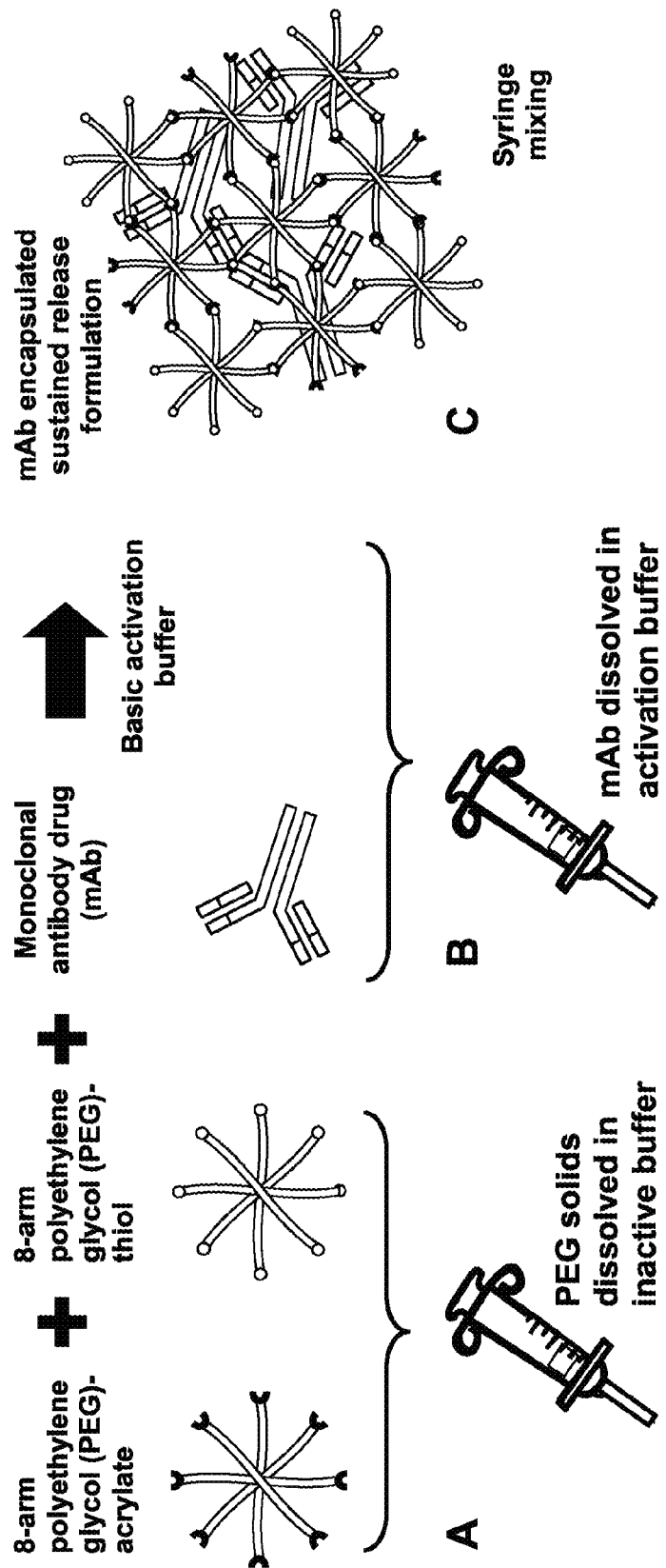

For the purposes of illustration and exemplification, and not limitation, an exemplary embodiment of a formulation and corresponding method of the disclosed subject matter is illustrated schematically in FIG. 1. As illustrated, the formulation embodied herein includes cross-linkable polymers (i.e., hydrophilic polymer strands capable of inter-polymer polymerization) as well as a biologic therapeutic. When cross-linked, the hydrophilic polymer strands form a three-dimensional network in which the biologic therapeutic is reversibly precipitated. The biologic therapeutic is effectively trapped in the cross-linked polymer network until the network swells and degrades, releasing the biologic therapeutic. Unexpectedly, it has been found that in formulations of the disclosed subject matter, where a biologic therapeutic is delivered in said cross-linked compositions, the biologic therapeutic renatures after release from the polymer network and the renatured biologic retains its therapeutic efficacy. It has further surprisingly been found that formulations of the disclosed subject matter can provide highly desirable release profiles of a biologic therapeutic, and can provide controlled triphasic release for thirty to ninety days.

According to one aspect of the disclosed subject matter, a formulation for providing controlled release of biologic therapeutics from a space within the body is provided. The formulation comprises a biologic therapeutic and a plurality of hydrophilic polymer strands capable of inter-polymer cross-linking. The formulations and associated kits can additionally comprise an activation buffer, a suspension buffer, and a delivery device. These are described in turn below.

I. Formulations

1. Biologic Therapeutics

According to the subject matter disclosed herein, a wide variety of biologic therapeutics can be used. For the purpose of illustration and not limitation, such biologic therapeutics include nucleic acids and proteins. Illustrative examples of suitable nucleic acids include siRNAs, antisense oligonucleotides, and DNA plasmids, while exemplary suitable proteins include growth factors, enzymes, cytokines, peptide hormones, cytokine traps and antibodies.

Suitable growth factors for use with the presently described subject matter include without limitation insulin-like growth factors (including IGF-1 and IGF-2), nerve growth factors, vascular endothelial growth factors (including VEGF A, VEGF B, VEGF C, VEGF D, PlGF and isoforms thereof), platelet-derived growth factors, granulocyte colony stimulating factor, brain-derived neurotrophic growth factor, transforming growth factors (including TGF-α and TGF-β), erythropoietin and angiopoietin. Suitable peptide hormones include without limitation insulin, glucagon, glucagon-like peptide 1, glucagon-like peptide 2, adrenocorticotropic hormone, human chorionic gonadotrophin, kisspeptin, luteinizing hormone, follicle stimulating hormone, leptin, cholecystokinin, ghrelin, antidiuretic hormone, oxytocin, angiotensin, and angiotensin II.

For purpose of illustration but not limitation, reference is primarily made hereinafter to antibodies. All antibodies, including, for example, mammalian, humanized, chimeric and fully human antibodies, are suitable for use in the disclosed formulations and corresponding methods and kits. Non-limiting examples of suitable antibodies include anti-tumor necrosis factor (TNF) antibodies, anti-interleukin-(IL-) 13 antibodies, anti-vascular endothelial growth factor (VEGF) antibodies, anti-matrix metalloproteinase 13 antibodies, and anti-IL-1 antibodies. Dual variable domain antibodies are also suitable for use with the disclosed subject matter. Suitable anti-TNF antibodies include, but are not limited to, adalimumab. Suitable anti-IL-13 antibodies include, but are not limited to, ABT-308. Particular antibodies suitable for use with the presently disclosed subject matter include, but are not limited to, trastuzumab (Herceptin™), bevacizumab (Avastin™), adalimumab (Humira™), ranibizumab (Lucentis™) aflibercept (Eylea™), etanercept (Enbrel™), rituximab (Rituxan™), pegfilgrastim (Neulasta™), interferon beta-1a (Avonex™), interfereon beta 1-a (Rebif™), and infliximab (Remicade™).

According to one aspect of the disclosed subject matter, it has surprisingly been found that peptide biologic therapeutics (such as antibodies and other proteins) undergo reversible precipitation in conjunction with their use in the formulations and corresponding kits and methods disclosed herein. While high concentrations of one hydrophilic polymer, polyethylene glycol (hereinafter, "PEG") have been demonstrated to cause precipitation of proteins, it is demonstrated herein that the peptide biologic therapeutics of the disclosed formulations unexpectedly retain their structure and function after re-solubilization. Said preservation of structure and function permits highly desirable extended release without tertiary and quaternary protein structure degradation. Where antibodies are employed as the biologic therapeutic of the disclosed subject matter, antigen binding of the biologic therapeutic is preserved, while release of the biologic therapeutic is sustained for a period of one to ninety days.

According to another aspect of the disclosed subject matter, it has been determined that in certain embodiments of the disclosed subject matter, the biologic therapeutic forms precipitates of about 100 nm to about 1 μm in diameter. Precipitates with a diameter in the range of 25 nm to about 10 μm are associated with desirable pharmacokinetic performance, as described below.

2. Hydrophilic Polymers

In accordance with another aspect of the disclosed subject matter, a plurality of hydrophilic polymer strands is provided, each of which is capable of inter-polymer strand polymerization, i.e., cross-linking with other hydrophilic polymer strands. In certain embodiments, the hydrophilic polymer strands include a functional group capable of cross-linking with functional groups provided on other hydrophilic polymer strands.

Hydrophilic polymers strands capable of inter-polymer polymerization include, without limitation, polyethylene glycol (PEG), hyaluronic acid, dextran, pectin, collagen, fibrinogen, alginate, PLLA-PEG-PLLA copolymers; PLDA-PEG-PLDA copolymers, PLGA-PEG-PLGA copolymers, PEG-PLLA copolymers, PEG-PLDA copolymers and PEG-PLGA copolymers. Suitable functional groups include, without limitation, thiol, vinyl, amino, aldehyde, vinylsulfone, succinimidyl, hydroxysuccinimidyl, nitrophenolate, and carbohydrazide moieties.

For purpose of illustration and not limitation, reference is made hereinafter to formulations and associated methods and kits comprising a plurality of PEG polymer strands. PEG is a synthetic polymer with a repeating structure of $(OCH_2CH_2)$ subunits. Additionally, PEG polymer strands suitable for use with the disclosed subject matter can include at least one functional group capable of inter-polymer strand polymerization. Accordingly, suitable PEG polymer strands of the disclosed subject matter include, without limitation, PEG-thiol, PEG-vinyl, PEG-amino, PEG-aldehyde, PEG-vinylsulfone, PEG-succinimidyl, PEG-hydroxysuccinimidyl, PEG-nitrophenolate, and PEG-carbohydrazide polymers. For the purpose of illustration only, the hydrophilic polymer strands can be polyethylene glycol molecules with a molecular weight between 2 and 30 kilodaltons.

Additionally, PEG polymer strands suitable for use with the disclosed formulations can include more than one functional group per polymer strand molecule prior to inter-polymer polymerization. Such PEG polymer strands are referred to herein as "multifunctional." PEG polymers suitable for use with the disclosed formulations include, without limitation, linear PEG, 2-arm PEG, 3-arm PEG, 4-arm PEG, 6-arm PEG, 8-arm PEG, and 16-arm PEG. Multifunctional PEG polymer strands are available in a variety of different structural configurations. Examples of structures that are suitable for the polymers of the disclosed formulations include, but are not limited to, linear, branched, star and comb configurations. In some embodiments of the disclosed subject matter, each arm of the hydrophilic polymer strands comprises a functional group such as depicted in FIG. 1. In some embodiments according to the disclosed subject matter, all of the functionalities provided on a multifunctional PEG polymer strand will consist of the same functional group.

According to some embodiments of the subject matter disclosed herein, the plurality of hydrophilic polymer strands comprises more than one type of PEG polymer. As disclosed herein, a type of PEG polymer refers to a plurality of PEG polymer strands having the same number of arms (e.g. 4-arm, 8-arm or 16-arm) and the same functional group (e.g. thiol or acrylate). In accordance with the disclosed subject matter, the plurality of hydrophilic polymer strands can comprise at least two types of PEG polymers, and the sum of the functionalities of the two types (i.e. the sum of m+n, where m represents the number of functionalities present on the first type of PEG polymer and n represents the number of functionalities present on the second type of PEG polymer) is between 2 and 32 (i.e. 2 or 3 or 4 or 5 or 6 or 7 or 8 or 9 or 10 or 11 or 12 or 13 or 14 or 15 or 16 or 17 or 18 or 19 or 20 or 21 or 22 or 23 or 24 or 25 or 26 or 27 or 28 or 29 or 30 or 31 or 32).

In some embodiments, the plurality of hydrophilic polymer stands comprises 2 types of PEG polymers. In some such embodiments, the first type of PEG polymer is PEG acrylate having 4 arms, and the second type of PEG polymer is PEG thiol having 4 arms. In further such embodiments, the first type of PEG polymer is PEG acrylate having 8 arms, and the second type of PEG polymer is PEG thiol having 8 arms. In still further embodiments, the first type of PEG polymer is PEG acrylate having 16 arms, and the second type of PEG polymer is PEG thiol having 16 arms. These types can be provided in a 1:1 ratio. However, in additional embodiments in accordance with the disclosed subject matter, the ratio of the first type of PEG polymer to the second type of PEG polymer will be between about 1:10 to about 10:1.

In further embodiments, the plurality of PEG polymer strands can comprise 4 types of PEG polymers. In some such embodiments, the first and second types of PEG polymer will have the same number of functionalities, and the third and fourth types of PEG polymers will also have the same number of functionalities, which can be different from the number of functionalities on the first and second types of PEG polymers. In further embodiments in which the number of functionalities on the first and second types of PEG polymers differs from the number of functionalities on the third and fourth types of PEG polymers, the ratio of the first and second types of PEG polymers relative to the third and fourth types of PEG polymers can be adjusted. For purpose of illustration and not limitation, the ratio of the first and second types of polymer to the third and fourth types of polymer can be 50:50, 25:75, or 75:25. As described below, by adjusting the ratio of the types of polymer strands present, it is possible to modify the controlled release characteristics of the formulation.

According to one aspect of the disclosed subject matter, it is unexpectedly shown that certain functionalities on the hydrophilic polymer strands are associated with improved preservation of structure and function of the biologic therapeutic upon resolubilization after reversible precipitation. Functionalities can be selected on the basis of solvent-exposed residues of the biologic therapeutic, as well as any post-translational modifications to the biologic therapeutic. For purpose of illustration and not limitation, reference is made herein to thiol functionalities and acrylate functionalities, which are associated with desirable controlled release properties as well as minimal interactions with select biologic therapeutics as described below.

In some embodiments of the disclosed subject matter, the weight ratio of the biologic therapeutic to the hydrophilic polymer is between about 1:1 to 1:125. In certain preferred embodiments, the weight ratio of the biologic therapeutic to the hydrophilic polymer is between 1:3.75 and 1:25. As described below, it has unexpectedly been demonstrated that this weight ratio can be adjusted according to the desired controlled release profile.

3. Suspension Buffer

In some embodiments of the disclosed subject matter, the biologic therapeutic and the plurality of hydrophilic polymer strands can be provided in a suspension buffer solution. Such suspension buffer solutions can have a pH of about 3.5 to about 6, and can comprise, without limitation, histidine, citrate and/or phosphate. Additional candidate buffers include succinate, acetate, tris and carbonate. In some exemplary embodiments, the suspension buffer can comprise 15 mM histidine at pH 5.2 or 0.05 molar citrate-phosphate buffer at pH 3.5. Buffer molarities between 0.05M and 3M are suitable for use with various embodiments of the disclosed subject matter. The suspension buffer will suspend and preserve the polymers and biologic therapeutic until inter-polymer polymerization. Alternatively, in some embodiments, either the hydrophilic polymer strands, the biologic therapeutic, or both the hydrophilic polymer stands and the biologic therapeutic can be provided in lyophilized form.

4. Suspension Buffer Additives

In certain embodiments according to the disclosed subject matter, the suspension buffer is provided which can include one or more additives. By way of illustration and not limitation, such additives can include salts, sugars, polyols, amino acids, preservatives, and/or additional compounds. Salts for use with the suspension buffer include, without limitation, sodium chloride, calcium chloride, and magnesium chloride. Sugars for use with the suspension buffer include, without limitation, sucrose, trehalose, mannose, and dextrose. Polyols for use with the suspension buffer include, without limitation, sorbitol, mannitol, and glycerol. Candidate amino acids for use with the suspension buffer include histidine, arginine, glycine, methionine, proline, lysine, glutamic acid, alanine, and arginine mixtures. Albumin and recombinant albumin can also be used with suspension buffers in certain embodiments. Suitable preservatives for use in suspension buffers of the disclosed subject matter include, without limitation, m-cresol, benzyl alcohol, and phenol. Polysorbates such as Tween 80 and Tween 20 can also be used, as can surfactants such as SDS, Brij 35, and triton x-10. Polysaccharides such as dextran, chelators such as EDTA, poloxamers such as Pluronics F-68 and F-127, polyvinylpyrrolidone, alkyl saccharides, and cellulosics can also be used in the suspension buffers of the disclosed subject matter. Additionally, low molecular weight PEG, i.e. PEG with a molecular weight less than 4000, can also be used as a suspension buffer additive.

5. Activation Buffers

In some embodiments of the disclosed subject matter, an activation buffer is also provided. As referred to herein, an activation buffer is a solution that catalyzes inter-polymer polymerization of the plurality of hydrophilic polymer strands. For purpose of illustration and not limitation, the activation buffer can be a carbonate buffer or a phosphate buffer. In some embodiments, the activation buffer has a pH between 7 and 10.5.

According to one aspect of the disclosed subject matter, inter-polymer polymerization or cross-linking of the hydrophilic polymer strands will occur between a functional group provided on one hydrophilic polymer strand and a functional group provided on another hydrophilic polymer strand. In some embodiments where two or more types of hydrophilic polymer strands with distinct functionalities are provided, and where one functionality is electrophilic and another is nucleophilic, cross-linking can occur via Michael's addition reactions, which are well known to those of skill in the art. For example, mixing polymer strands functionalized with thiol and polymers functionalized with acrylate in basic activation solution will result in deprotonation of the nucleophilic thiol group and subsequent donation of an electron to the electrophilic acrylate moiety to result in formation of inter-polymer thioether ester bonds. Additional suitable PEG cross-linking reactions are disclosed in U.S. Pat. No. 7,732,190 and U.S. Patent Application Publication No. 2009/0226519, which are incorporated by reference herein in their entirety.

According to another aspect of the disclosed subject matter, and as described below, the activation buffer can be selected to optimize controlled release characteristics of the formulation and to optimize preservation of function of the biologic therapeutic upon re-solubilization. It has surprisingly been demonstrated that the pH of the activation buffer can be selected to minimize cross-linking of the solvent-exposed residues of the biologic therapeutic and functionalities present on the hydrophilic polymer strands. In particular, by selecting a buffer with a pH slightly higher than the isoelectric point (hereinafter "pI") of the biologic therapeutic, structure and function of the biologic therapeutic are preserved during mixing of the hydrophilic polymer strands and biologic therapeutic with the activation buffer to catalyze inter-polymer polymerization.

In some embodiments, a subset of PEG polymer strands functionalized with nucleophilic functional groups will form covalent bonds with another subset of PEG polymer strands functionalized with electrophilic functional groups by Michael type reactions, which are well known to those of ordinary skill in the art. Suitable nucleophilic functional groups include, without limitation, thiol, amino, hydroxy, and $CO-NH-NH_2$ groups. Suitable electrophilic functional groups include, without limitation, acrylate, vinylsulfone, and N-hydroxysuccinimide groups. The basic activation buffer can catalyze inter-polymer polymerization by deprotonation of the nucleophilic functional groups to accelerate Michael type addition reactions.

In some embodiments of the disclosed subject matter, the percent weight to volume ratio of PEG polymer strands to activation buffer solution is between 5% and 30% of the volume of the activation buffer solution. As described below, it has unexpectedly been demonstrated that this weight to volume ratio can be adjusted according to the desired controlled release profile.

II. Cross-Linked Compositions

According to another aspect of the disclosed subject matter, the biologic therapeutic and hydrophilic polymer strands are combined and the hydrophilic polymer strands are cross-linked to form a cross-linked composition with the desirable release characteristics discussed above. According to one aspect of the disclosed subject matter, the formulations are mixed in the presence of activation buffer to catalyze inter-polymer polymerization (i.e. cross-linking) of the hydrophilic polymer strands, thereby forming the cross-linked composition that contains the biologic therapeutic in its interstitial spaces.

Figure 2:
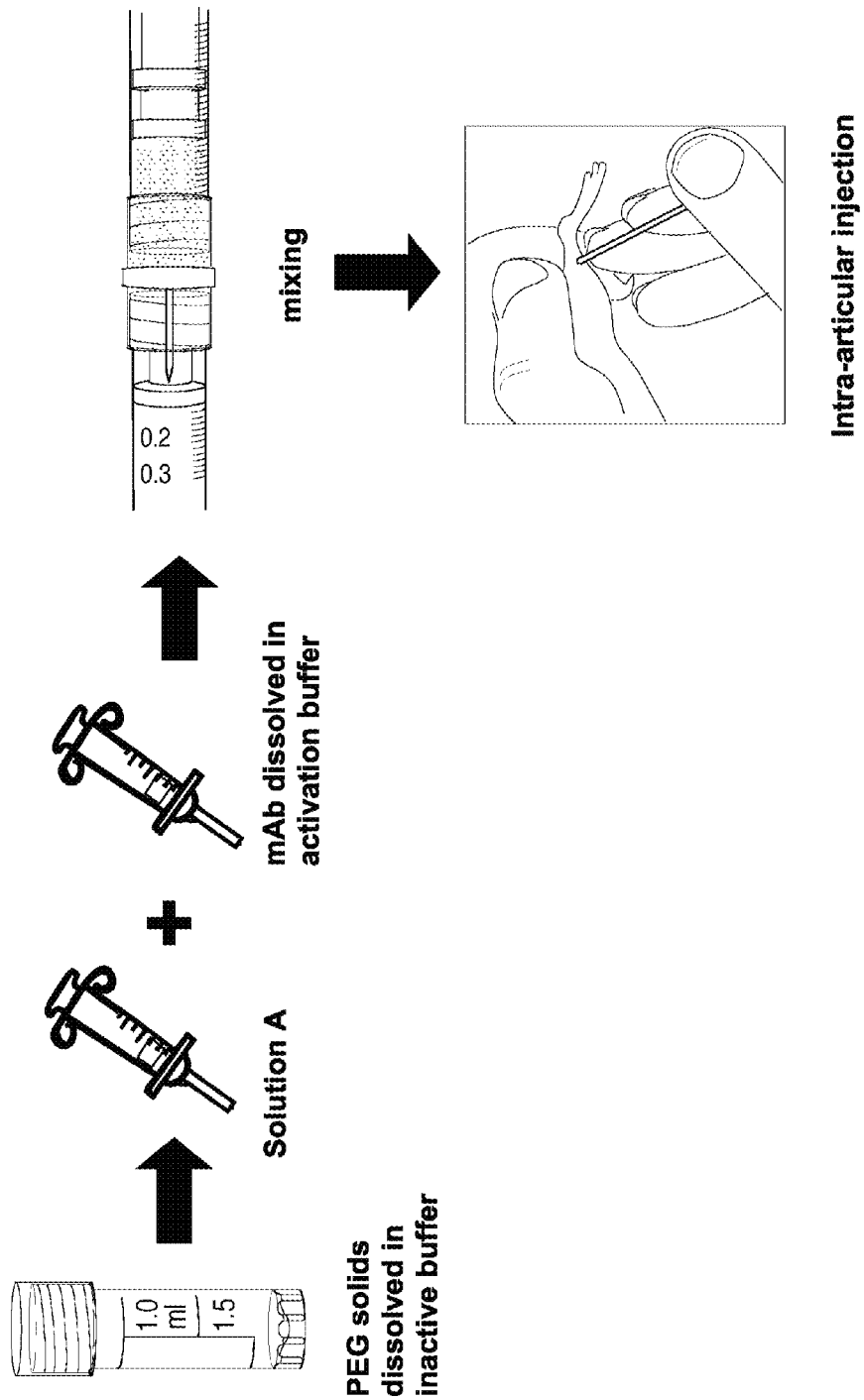

According to one non-limiting aspect of the disclosed subject matter, three elementary steps are performed for delivery of the cross-linked compositions of the disclosed subject matter. The biologic therapeutic is combined with the hydrophilic polymer strands, the hydrophilic polymer strands are cross-linked (e.g. by mixing with activation buffer), and the cross-linked composition is delivered to a space within the body. In some embodiments, it is possible to provide the biologic therapeutic and hydrophilic polymer strands in solution. Alternatively, these can be provided in lyophilized form for resuspension prior to delivery to a space within the body. In some embodiments, the biologic therapeutic and hydrophilic polymer strands can be mixed with activation buffer to cross-link the hydrophilic polymer strands shortly prior to administration to a space within the body. Alternatively, mixing can be performed in advance of delivery, and the resulting cross-linked composition comprising biologic therapeutic can be ground and lyophilized for resuspension prior to delivery. Cross-linked compositions of this latter embodiment can be referred to as "premixed." A non-limiting schematic illustration of premixed formulations is provided in FIG. 2.

In some embodiments of the disclosed subject matter, a formulation comprising a biologic therapeutic and hydrophilic polymer strands is provided in solution. The formulation solution is mixed with basic activation buffer to catalyze inter-polymer polymerization. In some embodiments, a subset of PEG polymer strands functionalized with nucleophilic functional groups will form covalent bonds with another subset of PEG polymer strands functionalized with electrophilic functional groups by Michael type reactions, which are well known to those of ordinary skill in the art. Suitable nucleophilic functional groups include, without limitation, thiol, amino, hydroxy, and $CO-NH-NH_2$ groups. Suitable electrophilic functional groups include, without limitation, acrylate, vinylsulfone, and N-hydroxysuccinimide groups. The basic activation buffer can catalyze polymer strand cross-linking by deprotonation of the nucleophilic functional groups to accelerate Michael type addition reactions.

According to some embodiments of the disclosed subject matter, polymer strand cross-linking is initiated ex vivo and proceeds to completion in vivo, i.e. in the space within the body to which the formulation is delivered. Following initiation of inter-polymer polymerization (cross-linking), the mixture is administered to a space within the body, where the cross-linking reaction completes to form a cross-linked composition. In additional embodiments, lightly cross-linked PEG that is still syringe-extrudable can be formed and subsequently mixed with biologic therapeutic. Subsequently, further cross-linking can be achieved by mixing with a second activation buffer. Mixing in this manner will permit minimal contact time between the biologic therapeutic and the functional groups on the PEG polymer strands and the basic activation buffer to permit greater loading of biologic therapeutic and further enhanced preservation of activity of the biologic therapeutic.

According to some aspects of the disclosed subject matter, the formulation in solution is mixed with the activation buffer by syringe mixing. In this regard, it has surprisingly been demonstrated that, in certain non-limiting embodiments, a particular degree of syringe mixing is associated with desirable precipitate size and release profile. For example, and as illustrated in FIG. 6, in some embodiments, syringe mixing using generally consistent plunger strokes for between about 3 seconds to about 10 seconds (e.g. about 5 to 15 μlunger strokes) will result in desired precipitate size and uniformity, while mixing for longer durations, e.g., by 30 μlunger strokes or more, is associated with large, sticky precipitates and loss of biologic therapeutic. Various suitable syringes can be used for mixing, including 1 ml Becton Dickinson syringes connected with female-to-female Luer fittings. Similar results are obtained by methods of mixing which provide approximately equivalent total shear force and duration of exposure to shear force to the formulation. Biologic therapeutic precipitates with a diameter in the range of 50 nm to 10 μm are associated in some embodiments with the desirable re-solubilization and release profiles described above. In some embodiments, biologic therapeutic precipitate size up to 250 μm is provided. In some embodiments, mixing is performed by vortexing or repeated inversion of the mixture of formulation and activation buffer.

According to another aspect of the disclosed subject matter, upon inter-polymer polymerization of the plurality the hydrophilic polymer strands in the presence of the biologic therapeutic, a cross-linked composition will form. According to the disclosed subject matter, the plurality of hydrophilic polymer strands can be selected to optimize the characteristics of the cross-linked composition after cross-linking. Cross-linking density of the cross-linked composition, for example, will be influenced by the molecular weight of the polymer strands, the duration of the gelation reaction (i.e. the "Gelation Time"), the number of PEG arms, the functional groups present on the PEG polymer strands, and the concentration of PEG solids in solution before inter-polymer cross-linking. The pH of the suspension buffer, suspension buffer additives, and the activation buffer used to catalyze the inter-polymer cross-linking will also influence gelation time, cross-linking density and resultant precipitant size of the biologic therapeutic. Generally, cross-linking density will increase with lower molecular weight polymers, a greater proportion of PEG arms per hydrophilic polymer strand, a higher concentration of PEG solids in solution, and a higher pH of the activation buffer. The cross-linking density of the cross-linked composition will be a determinant of its release profile with regard to a biological therapeutic.

By way of example, and as illustrated in FIG. 3A and FIG. 3B, varying the ratio of 4-arm PEG to 8-arm PEG and altering the weight to volume ratio of PEG solids of the formulation will alter the controlled release profile of the cross-linked compositions. As shown, each cross-linked composition provides desirable controlled release and duration, but such release can be optimized according to the biologic therapeutic, the indication, the situs of delivery and other considerations. Additionally, as discussed in Example 13 and as illustrated in FIG. 5, by adjusting the weight percentage of hydrophilic polymer and the weight ratio of the biologic therapeutic to the hydrophilic polymer, the size of the precipitates of the biologic therapeutic will be adjusted, with concomitant effect on the release profile of the cross-linked formulation.

It has surprisingly found that by cross-linking PEG polymer strands into a cross-linked composition network during or subsequent to protein precipitation in the presence of PEG, the protein is protected from covalent interaction with the functional groups of the PEG polymer strands, and its biologic activity is maintained after re-solubilization. Furthermore, by providing an activation buffer for cross-linking catalysis, relatively rapid cross-linking is achieved between the PEG polymer strands, thereby minimizing the opportunity for reactive solvent-exposed residues of the protein, including, for example, amine groups, to react with the cross-linking functionalities of the PEG polymers, including, for example, acrylate groups. Additionally, the cross-linking functionalities of the PEG polymer strands can be selected to minimize covalent modification of solvent-exposed residues of the protein. For example, where a protein is characterized by a high proportion of cysteine residues that do not participate in disulfide bonding, PEG polymer strands with a cross-linking functionality such as an amine group can be preferred to PEG polymer strands with cross-linking functionalities such as a thiol group to minimize the formation of disulfide bonds between the biologic therapeutic and the PEG polymer strands.

After cross-linking of the hydrophilic polymer strands, the resultant cross-linked compositions will absorb water. As the cross-linked compositions absorb water, they will swell as their volume increases. As the volume of the cross-linked composition increases, the precipitated biologic therapeutic will re-solubilize and diffuse out of the polymer matrix. Additionally, water will hydrolyze the thioether ester bonds between the component polymers of the cross-linked composition, resulting in further release of the biologic therapeutic. Further, the biologic therapeutic can reduce equilibrium water uptake and thereby further prevent the cross-linked composition from significant swelling. The formed cross-linked composition can have an interpenetrating or a semi-interpenetrating network structure.

In addition to the release profile of the cross-linked composition, additional parameters of the composition can be optimized for suitability of delivery to a space within the body, such as an intra-articular space. For example, viscoelasticity and elastic modulus of the cross-linked composition can be considered to maximize patient comfort. The eventual maximum volume of the cross-linked composition, which will depend on its swelling ratio in vivo, will limit the total amount of the formulation which can be delivered to a space within the body. Additionally, because the formed polymer composition is composed of hydrophilic polymer strands, it is resorbable in vivo, permitting repeated administration of a cross-linked composition to the same space within a body.

FIG. 4A illustrates the relationship between swelling of the cross-linked composition and biologic therapeutic release. It is apparent from the parallel plots that swelling and release of the biologic therapeutic occur in parallel. Additionally, FIG. 4B provides times to visible dissolution of various cross-linked compositions in vitro. As discussed, multiple variables can be adjusted to achieve desired a desired dissolution rate of the cross-linked composition.

2. Size and Homogeneity of Biologic Therapeutic Precipitates

According to the subject matter disclosed herein, formulation of a biologic therapeutic with a hydrophilic polymer produces precipitates of the biologic therapeutic within the cross-linked hydrophilic polymer matrix. These precipitates surprisingly retain their structure and function after diffusing from the polymer matrix and resolubilizing. Based on the particular formulations employed, the force and duration of mixing, the biologic therapeutic selected, the pH of the suspension and activation buffers, and other variables, the size of the precipitates will vary. For example, and as illustrated in FIG. 5, increasing proportions of PEG solids and concentrations of biologic therapeutic are associated with larger precipitant size. At 25% PEG solids and above, sedimentation of biologic therapeutic is also observed.

Moreover, as shown in FIG. 6A-D, the extent of mixing will also influence the size of the biologic therapeutic precipitates that result. As illustrated, mixing by 5 to 15 μlunger strokes is associated with smaller precipitates, while mixing with 30 μlunger strokes is associated with larger, stickier precipitates. While precipitate sizes between 50 nm and 10 μm are preferred in some embodiments, precipitate sizes up to 250 μm can be formed. Precipitate size preference will depend primarily on the biologic therapeutic, including its indication, its potency and its pharmacokinetics. Larger precipitates will generally be associated with peaks and troughs in local, and, to a lesser extent, systemic concentration, relative to smaller and more uniform precipitates.

As further illustrated in FIG. 6A-D, homogeneity of precipitates is also influenced by the extent of mixing, as well as the composition of the hydrophilic polymer strands. 8-arm PEG, as shown in FIG. 6B (10% PEG solids) and FIG. 6D (20% PEG solids), which forms a denser network of cross-linked hydrophilic strands than 4-arm PEG, is generally associated with a greater degree of homogeneity of precipitate size and distribution than 4-arm PEG, as shown in FIG. 6A (10% PEG solids) and FIG. 6C (20%) PEG solids.

For purpose of illustration, FIG. 7 provides precipitate size that can be achieved with the formulations and according to the protocol described in Example 4 below. Precipitate size was determined using Nanoparticle Tracking Analysis Version 2.2 Build 0366 from Nanosight. Precipitates of biologic therapeutic with a diameter of about 50 nm to about 400 nm are provided. As illustrated, the size of the precipitates exhibits a generally Gaussian distribution. In further embodiments, precipitates of biologic therapeutic with a diameter of about 50 nm to about 10 μm are provided. In still further embodiments, precipitates of biologic therapeutic with a diameter of about 10 μm m to about 250 μm are provided III. Use of Cross-Linked Compositions 1. Controlled Release The cross-linked compositions of the disclosed subject matter are suitable for delivery to a wide variety of spaces within the body, including sinus cavities of the head and organs, the medulla of long bones, the intra-thoracic and intra-peritoneal spaces, the lumen of blood vessels, exocrine ducts, intra-ocular (e.g., intra-vitreal) spaces, and intra-articular spaces. For purpose of illustration and not limitation, reference is made hereinafter to delivery of cross-linked compositions according to the subject matter disclosed herein to an intra-articular space or intra-ocular space in the body. Turnover of synovial fluid from the intra-articular spaces to the plasma is relatively rapid. As a result, delivery of soluble biologic therapeutics to the intra-articular spaces is not effective for maximizing intra-articular concentration and minimizing systemic concentration, particularly for therapeutic agents with relatively long half-lives. This phenomenon is illustrated in FIG. 8A and FIG. 8B. As shown, unformulated (i.e. non-polymer matrix encapsulated) monoclonal antibody is injected into the intra-articular space at $t_0$, and intra-articular and systemic concentrations are monitored. Within 12 hours, the local (intra-articular) concentration of antibody has decreased by two orders of magnitude, to approximately the same concentration as found in the plasma, while systemic exposure is not controlled. Intra-vitreal fluid turnover is also quite high, and moreover the eye is separated from the systemic circulation by the blood-ocular barrier, which inhibits systemic delivery of drugs to the eye.

In contrast, and in accordance with one aspect of the disclosed subject matter, the formulations disclosed herein exhibit release profiles that are highly advantageous in local delivery of biologic therapeutics. For purpose of illustration and not limitation, such release profiles can be characterized by a "burst" or relatively instant release of a proportion of the total biologic therapeutic delivered by administration of a cross-linked composition to a space within the body within 24 hours. Such a "burst effect" is illustrated in FIG. 9A, which illustrates that short-term release of the biologic therapeutic is controlled. This diminished burst effect reduces systemic exposure. The release profiles of specific embodiments can further be characterized by an initial release of a maximum proportion of the total biologic therapeutic administered within the first seven days of administration. In further embodiments, the release profiles can be characterized by an extended duration of release of the biologic therapeutic from the cross-linked composition matrix to a space within the body.

In additional embodiments of the disclosed subject matter, the release profile is triphasic, with a first rate of release for a first period of between about 0 to 30 days, a second rate of release for a second period of about 0 to 30 days, and a third rate of release for a third period of about 0 to 30 days. In some preferred embodiments, at least one phase of a triphasic release profile will exhibit approximately linear or zero-order release kinetics, i.e. the rate of release of the biologic therapeutic will be approximately the same for the duration of the phase. A triphasic release profile according to an aspect of the disclosed subject matter is illustrated in FIG. 9B. As shown, the triphasic release profile provides steady and prolonged release of the biologic therapeutic for a duration of thirty to ninety days. As discussed below, such release profiles result in higher local concentration and reduced systemic concentration of a biologic therapeutic relative to administration of an unformulated biologic therapeutic. A non-limiting list of exemplary formulations which provide a release profile as described is provided in Table 1, which provides the specifications for various components of cross-linked components as disclosed herein. In some non-limiting embodiments, pharmacokinetic results according to Table 2 are achieved.

As disclosed herein, a "burst effect" refers to the proportion of biologic therapeutic released from the cross-linked composition to the space within the body within the first 24 hours after administration of the cross-linked composition. For the purpose of illustration and not limitation, the burst effect can represent a release of about 0.1 percent of the total biologic therapeutic delivered to about 30 percent of the total biologic therapeutic delivered. In some embodiments, the burst effect is between about one percent and about ten percent of the total biologic therapeutic delivered. In further embodiments, the burst effect is between about ten percent and about twenty percent. In still further embodiments, the burst effect is between twenty percent and thirty percent. As disclosed herein, the term "initial cumulative release" refers to the proportion of biologic therapeutic released from the cross-linked composition to the space within the body within the first seven days after administration, inclusive of the proportion released over the first 24 hours. In some embodiments, the initial release can represent less than ten percent of the total biologic therapeutic delivered. In additional embodiments, the initial release constitutes ten to twenty percent of the total biologic therapeutic delivered. In some embodiments, the initial release is between twenty and thirty percent. In still further embodiments, the initial release is between about thirty and forty percent. As disclosed herein, and a "triphasic release profile" refers to a release profile of the biologic therapeutic, i.e., a plot of the proportion of biologic therapeutic released from the cross-linked composition over time, with three identifiable rates of release of definite duration. FIG. 9B provides an exemplary, non-limiting illustration of a triphasic release profile in accordance with the subject matter disclosed herein.

The controlled release provided by formulations of the disclosed subject matter results in markedly improved pharmacokinetic endpoints for delivery of the biologic therapeutic. Total and maximum systemic exposure are reduced, while local concentration is maximized, over the entire duration of release, thereby both maximizing efficacy of the treatment and minimizing undesirable side effects. These improved pharmacokinetics are illustrated in FIG. 10. As shown, after delivery of a formulation comprising ABT-308 according to the disclosed subject matter, systemic concentration of the biologic therapeutic (a monoclonal antibody) is minimized, while intra-articular concentration is maintained, for 14 days. Furthermore, as shown in Table 3, the average ratio of concentration of the biologic therapeutic in the synovial fluid to the concentration of the biologic therapeutic is greater than 100. These pharmacokinetic endpoints represent a very significant improvement over unformulated antibody as illustrated in FIG. 8A.

2. Ratio of Systemic Concentration to Local Concentration of Biologic Therapeutic It is an objective of the subject matter disclosed herein to provide a ratio of the systemic concentration of the biologic therapeutic to local concentration of the biologic therapeutic in the intra-articular space that is less than 1 for between about 1 day to about 90 days after delivery of the cross-linked composition to the intra-articular space. In certain preferred embodiments of the disclosed subject matter, the ratio of the systemic concentration of the biologic therapeutic to local concentration of the biologic therapeutic will be lower than 0.1. As referred to herein, a "local concentration" of a biologic therapeutic is the concentration of the biologic within the space in the body to which it is delivered, while a "systemic concentration" of a biologic therapeutic is the equilibrated serum concentration of the biologic in the organism to which it is delivered.

The ratio of local concentration of the biologic therapeutic to the systemic concentration of the biologic therapeutic will be influenced by many factors. Depending on the space within the body to which formulations of the disclosed subject matter are administered, the ratio will depend on the degree of vascularization, the surrounding density of venules or capillaries, the rate of lymphatic clearance, and/or the rate of fluid turnover of said space within the body. Additional factors will also influence this ratio, including the relative size of the subject to which the formulation is delivered, the relative level of activity of the subject, and the volume of the space to which the formulation is delivered. The ratio will additionally be influenced by the half-life of the biologic therapeutic.

For the purpose of illustration and not limitation, suitable spaces within the body for delivery of formulations in accordance with the disclosed subject matter include an intravitreal space, an intra-articular space, an intra-peritoneal space, an intra-arterial space, an intra-osseal space, a sinus cavity, or an exocrine duct. For the purpose of illustration and not limitation, reference is made herein to a ratio of local concentration of biologic therapeutic to systemic concentration of biologic therapeutic after delivery of a formulation according to the disclosed subject matter to an intra-articular space.

With reference to embodiments in which the composition is delivered to an intra-articular space, a ratio of systemic concentration to local concentration of the biologic therapeutic less than one is achieved by the relatively slow, controlled elution of the biologic from the cross-linked composition as described. After elution from the cross-linked composition, the biologic is temporarily retained in the intra-articular space where it can bind to or otherwise interact with target antigens, receptors, or ligands, or otherwise achieve a desired local therapeutic effect. In some preferred embodiments, a significant proportion of the biologic therapeutic is eliminated or inactivated prior to entering systemic circulation. Elimination can occur by immune-mediated clearance, renal filtration, enzymatic breakdown, or any other means.

According to the subject matter disclosed herein, the ratio of the systemic concentration of the biologic therapeutic to local concentration of the biologic therapeutic that results after delivery of the formulation to an intra-articular space is between about 1 and 0. In some preferred embodiments, the ratio is less than 0.1. In some preferred embodiments, the ratio is between about 0.1 and about 0.001. In other preferred embodiments, this ratio is between about 0.2 and about 0.002. In additional preferred embodiments, this ratio is between about 0.5 and about 0.005. As shown in Table 3, Table 4A and Table 4B, ratios of approximately 0.2 to approximately 0.01 are achieved by intra-articular delivery of certain cross-linked compositions formulations according to the disclosed subject matter. Significantly, this ratio is approximately 25 to 500 times lower than the ratio that results from administration of unformulated biologic, which is between about 5 and about 7. Similar results are shown in Table 5 and Table 6. With reference to FIG. 10, the concentration of biologic therapeutic in the synovial fluid is approximately two orders of magnitude greater than the concentration of biologic therapeutic in the serum for the duration of monitoring, as described in Example 7 below. As discussed in Example 8 below, this ratio of local to serum concentration is maintained after delivery of formulations according to the disclosed subject matter for between 30 and 90 days.

In some embodiments according to the disclosed subject matter, a ratio of systemic concentration of the biologic therapeutic to local concentration of the biologic therapeutic less than one is provided for a duration of about 1 to about 90 days after delivery of the cross-linked composition to a space within the body. In some preferred embodiments, a less than one is provided for about 1 to about 7 days after delivery. In additional embodiments, a ratio less than one is provided for about 1 to about 14 days after delivery. In additional preferred embodiments in accordance with the disclosed subject matter, a ratio less than 1 is provided for about 14 to about 30 days after delivery. In still further embodiments, a ratio less than 1 is provided for between about 30 to about 60 days. In further embodiments, a ratio of systemic concentration of the biologic therapeutic to local concentration of the biologic therapeutic less than one is provided for between about 60 days and about 90 days after delivery of the cross-linked compositions in accordance with the disclosed subject matter to a space within the body. In additional preferred embodiments, the ratio is less than 0.1.

3. Methods of Treatment

As a result of the desirable controlled release properties and resulting ratio of systemic concentration to local concentration of biologic therapeutic less than one described above, polymerized (cross-linked) compositions of the disclosed subject matter are particularly beneficial in the treatment of disease. A wide variety of diseases are suitably treated by methods comprising delivery of the cross-linked compositions disclosed herein. including without limitation cancer, diseases of the eye, inflammation, autoimmune disease, wounds, fractures, infectious disease, or cardiovascular disease, are provided. The methods include combining a biologic therapeutic and a plurality of hydrophilic polymer strands to form a combination, mixing the combination with an activation buffer to induce inter-polymer polymerization of the hydrophilic polymer strands to form a cross-linked composition which includes reversibly precipitated biologic therapeutic, and administering the cross-linked composition to a patient in need thereof, and thereby treating the disease.

In some embodiments in accordance with the disclosed subject matter, methods are provided to treat a localized cancer, such as a tumor. Such methods will include the steps of mixing a formulation and cross-linking that formulation to form a cross-linked composition as disclosed, and delivering the cross-linked composition, e.g., to a tumor, to a blood vessel supplying a tumor, or to a space within the body proximate to a tumor. In further embodiments, the biologic therapeutic will be an anti-angiogenesis drug, such as an anti-VEGF antibody.

In some embodiments, methods of treating diseases of the eye, such as macular degeneration, are provided. Such methods will include the steps of mixing a formulation and cross-linking that formulation to form a cross-linked composition as disclosed, and delivering the cross-linked composition, e.g., to the intra-vitreal space of the eye. In further embodiments, the biologic therapeutic will be an anti-angiogenesis drug, such as an anti-VEGF antibody. In additional non-limiting embodiments, methods of treating inflammation are provided. Such methods will include the steps of mixing a formulation and cross-linking that formulation to form a cross-linked composition as disclosed, and delivering the cross-linked composition, e.g., to a site of inflammation or a space within the body proximate to a site of inflammation. In further embodiments, the biologic therapeutic will be an anti-inflammatory compound, such as an antibody which binds and neutralizes inflammatory cytokines. In some embodiments, the drug will be an anti-TNF antibody, an anti-IL-13 antibody, or an anti-IL-1 antibody.

In some embodiments, methods of treating diseases an autoimmune disease, such as rheumatoid arthritis, are provided. Such methods will include the steps of mixing a formulation and cross-linking that formulation to form a cross-linked composition as disclosed, and delivering the cross-linked composition, e.g., to the intra-articular spaces of affected joints. In further embodiments, the biologic therapeutic will be an antibody which neutralizes anti-inflammatory cytokines, such as an anti-TNF antibody.

In some embodiments, methods of treating joint diseases, such as osteoarthritis, are provided. Such methods will include the steps of mixing a formulation and cross-linking that formulation to form a cross-linked composition as disclosed, and delivering the cross-linked composition, e.g., to the intra-articular spaces of affected joints. In further embodiments, the biologic therapeutic will be an antibody which neutralizes anti-inflammatory cytokines, such as an anti-TNF antibody, an antibody which neutralizes proteases that break down cartilage in affected joints, such as an anti-Matrix Metalloproteinase 13 antibody.

In some embodiments, methods of treating wounds are provided. Such methods will include the steps of mixing a formulation and cross-linking that formulation to form a cross-linked composition as disclosed, and delivering the cross-linked composition, e.g., to a wound or space in the body proximate to a wound. In further embodiments, the biologic therapeutic will be a protein which promotes wound healing, inhibits scarring, or prevents infection.

In some embodiments, methods of treating bone fracture are provided. Such methods will include the steps of mixing a formulation and cross-linking that formulation to form a cross-linked composition as disclosed, and delivering the cross-linked composition, e.g., to fractured bone or a space in the body proximate to the fractured bone. In further embodiments, the biologic therapeutic will be a protein which promotes fracture healing.

In some embodiments, methods of treating infection are provided. Such methods will include the steps of mixing a formulation and cross-linking that formulation to form a cross-linked composition as disclosed, and delivering the cross-linked composition, e.g., to an infected area of the body. The infection can be caused by a viral pathogen, a bacterial pathogen, or a fungal pathogen. In further embodiments, the biologic therapeutic will be an antibody to the viral, bacterial or fungal pathogen.

In some embodiments, methods of treating cardiovascular disease, such as coronary artery disease, are provided. Such methods will include the steps of mixing a formulation and cross-linking that formulation to form a cross-linked composition as disclosed, and delivering the cross-linked composition, e.g., to a space within the body. In further embodiments, the biologic therapeutic will be an anti-coagulant, an anti-inflammatory, or an anti-lipidemic protein.

In further embodiments, methods of treating scarring due to surgery, such as post-surgical would adhesions, are provided. The surgery can be invasive, including for example bowel resection, or non-invasive, including for example arthroscopic ligament repair. Such methods will include the steps of mixing a formulation and cross-linking that formulation to form a cross-linked composition as disclosed, and delivering the cross-linked composition, e.g., to the site of the surgery. Delivery can occur before or after closure of any surgical wounds. In further embodiments, the biologic therapeutic will be an anti-fibrotic protein.

In further embodiments, methods of treating diseases of the skin, such as psoriasis, are provided. Such methods will include the steps of mixing a formulation and cross-linking that formulation to form a cross-linked composition as disclosed, and delivering the cross-linked composition, e.g., to the subcutaneous space proximate a psoriasis lesion. In further embodiments, the biologic therapeutic will be an anti-inflammatory or immunomodulatory protein.

In further embodiments, methods of treating endometriosis are provided. Such methods will include the steps of mixing a formulation and cross-linking that formulation to form a cross-linked composition as disclosed, and delivering the cross-linked composition, e.g., to the intra-peritoneal space. In further embodiments, the biologic therapeutic will be an anti-estrogenic protein.

IV. Kits

According to another aspect of the disclosed subject matter, kits are provided which separately comprise in various combinations the plurality of hydrophilic polymer strands, the biologic therapeutic, and, optionally, the activation and suspension buffers, as well as a delivery device for delivery of the cross-linked compositions to a space within the body. A variety of delivery devices are suitable for the formulations and cross-linked compositions of the disclosed subject matter. For purpose of illustration and not limitation, a single-bore syringe, a dual bore syringe, or a multichannel delivery device with mixing head can be used. In some embodiments, the formulation and activation buffer are provided in separate channels of a multichannel delivery device which includes a mixing head. In additional embodiments, the biologic therapeutic and plurality of hydrophilic polymer strands are provided as a cross-linked composition for reconstitution shortly prior to administration.

In some embodiments, a kit can comprise a first solution comprising a suspension buffer and a plurality of hydrophilic polymer strands (as described above) and a second solution comprising a biologic therapeutic and an activation buffer (also described above). In other non-limiting embodiments, a kit separately comprising a first solution comprising a biologic therapeutic and a plurality of hydrophilic polymer strands and an activation buffer is provided. For convenience, these components can be provided in separate channels of a dual-bore syringe or multichannel delivery device.

Various publications are cited herein, the contents of which are hereby incorporated by reference in their entireties.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

5. EXAMPLES

5.1 Example 1

Formulations of 8-arm PEG functionalized with thiol or acrylate in a 1:1 ratio and adalimumab with 5%, 6.3%, 7.5%, 11.5% or 20% weight to volume ratios of PEG solids were mixed with phosphate activation buffer at pH 8.0 or carbonate activation buffer at pH 9.5 as indicated to form cross-linked compositions. Antibody loading relative to PEG solids was 20%, 27%, 32% or 50% as indicated. After 18 days and 26 days of incubation in vitro, size exclusion chromatography was performed on the biologic therapeutic released from the cross-linked compositions to determine the proportion of monomers released relative to the proportion of aggregates and fragments. A high proportion of monomers (e.g. >90%) is indicative of good reversible precipitation and re-solubilization of the biologic therapeutic. As illustrated in FIG. 11A and FIG. 11B, a high proportion of monomers is released from the cross-linked compositions at 18 days and 26 days after polymerization of the formulation. As seen in FIG. 11A, where PEG functionalized with NHS is employed, a higher proportion of aggregates and fragments is produced.

4-arm PEG-acrylate and 4-arm PEG-thiol at five percent by weight PEG solids and twenty percent by weight PEG solids were formulated with lyophilized adalimumab antibody in doses of either 8 mg or 0.8 mg in a solution of sodium phosphate buffer with pH 8. 50 µL of formulation was injected into the intra-articular space of healthy rat hind limbs. Groups A and C received cross-linked compositions formed from 20% PEG solids, Groups B and D received cross-linked compositions formulated with 5% PEG solids, and Groups E and G were administered unformulated mAb. Groups A and B received 8 mg mAb, while the remaining groups received 0.8 mg mAb. Table 7 illustrates the serum exposure of the antibody, as measured by TNF-alpha binding quantification assays, while FIG. 12 illustrates the concentration of mAb over time up to 14 days after delivery. Delivery via cross-linked composition significantly reduced adalimumab serum concentration. FIG. 13A, FIG. 13B and FIG. 13C are photographs of the cross-linked compositions after injection into rat hind limb and after removal from rat hind limb.

5.2 Example 2

4.25 mgs of unformulated adalimumab antibody was administered to the intra-articular space of the hind limb of healthy rats in 50 µl of phosphate buffered saline. Serum concentration and synovial fluid concentration of adalimumab were monitored at intervals over 24 hours after administration. As illustrated in FIGS. 8A and 8B, unformulated antibody is rapidly cleared from the synovial fluid and enters the serum, resulting in relatively low synovial fluid concentration and high systemic exposure after twelve hours. A relatively high concentration of antibody in the joint is seen two hours after administration. Within approximately ten hours of administration, the local concentration of the biologic therapeutic in the synovial fluid has decreased about two orders of magnitude, and serum exposure of the biologic therapeutic is relatively high.

5.3 Example 3

10%, 15% and 20% weight to volume ratio solutions of 8-arm PEG functionalized with thiol or acrylate in a 1:1 ratio and ABT-308 in a 1:25 ratio of biologic therapeutic to PEG solids were prepared. The molecular weight of the polymer strands was 10 kDa. Half of these solutions were mixed with activation buffer to form a cross-linked composition. Half of the solutions were pre-mixed. Pre-mixed solutions consist of PEG solids dissolved in suspension buffer, which are mixed with the biologic therapeutic dissolved in activation buffer to form a cross-linked composition. The cross-linked compositions were observed in vitro and the initial release of biologic therapeutic over the first four hours of incubation was determined. As shown in FIG. 9A, an average of 6.8% of the biologic therapeutic was released from the pre-mixed cross-linked compositions and an average of 7.9% was released from the non-pre-mixed 20% PEG cross-linked compositions. Initial release of biologic therapeutic as low as 3% was observed for the pre-mixed cross-linked compositions. FIG. 9B provides an exemplary triphasic release profile according to one aspect of the disclosed subject matter. FIGS. 14A and 14B illustrate all in vitro release data from the experiment. Increasing PEG solids from 10% to 15% appears to reduce the rate of mAb release.

Figure 3A:
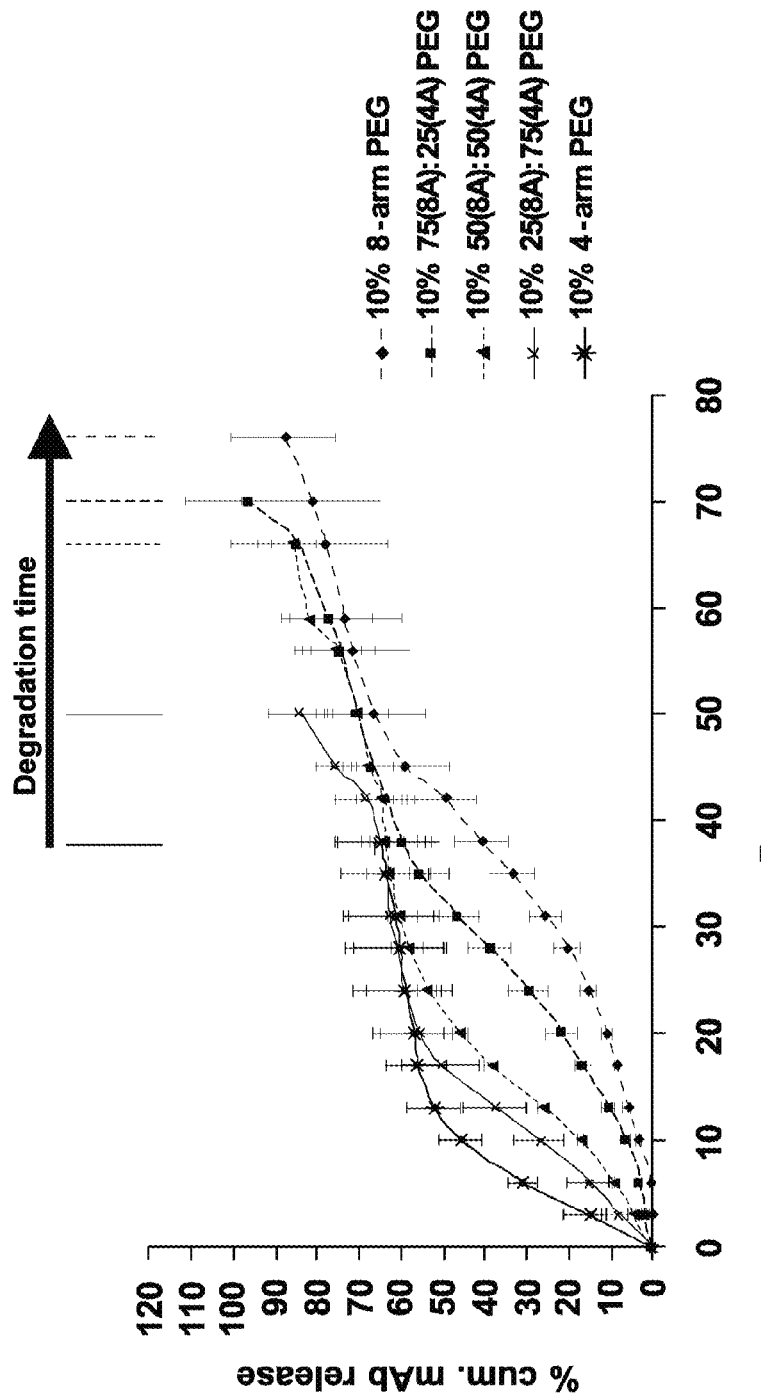
Figure 3B:
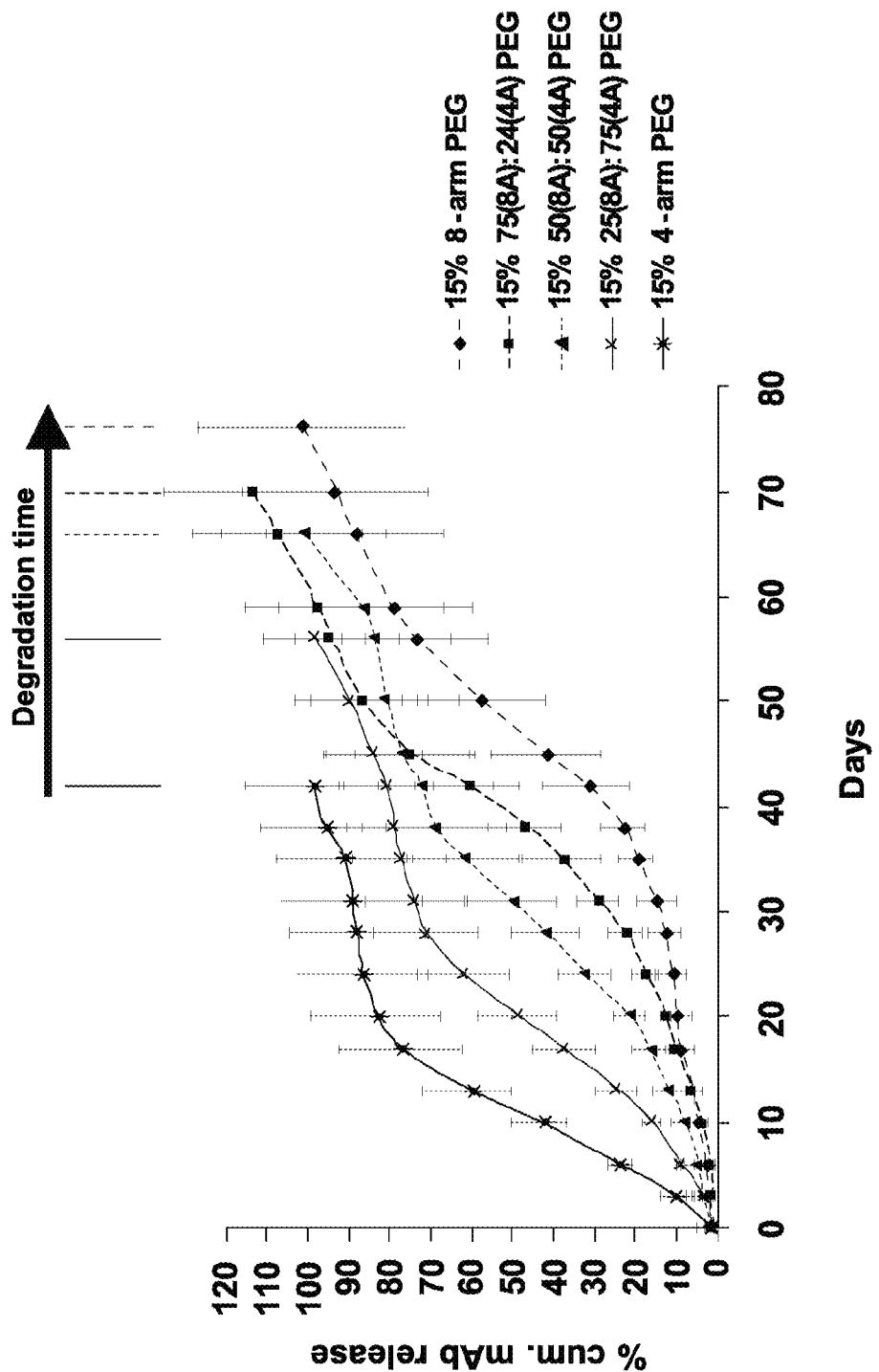

Additional extended release in vitro assays were conducted in which the controlled release profile of pre-mixed 8-arm, 4-arm, and blended 8-arm/4-arm PEG gels were evaluated. The cross-linked compositions were formed by mixing either 8-arm PEG functionalized with thiol or acrylate in a 1:1 ratio and ABT-308 in a 1:25 ratio of biologic therapeutic to PEG solids, 4-arm PEG functionalized with thiol or acrylate in a 1:1 ratio and ABT-308 in a 1:25 ratio of biologic therapeutic to PEG solids, or a mixture of the 8-arm and 4-arm PEG formulations in a ratio of 25:75, 50:50 or 75:25 8-arm PEG to 4-arm PEG. The total weight to volume ratio of the PEGs in solution was 10% or 15%. As shown in FIG. 3A and FIG. 3B, it was observed that all cross-linked compositions, whether formulated with 10% PEG solids or 15% PEG solids, exhibited a triphasic release profile of the biologic therapeutic, with an initial release rate for a duration of 0-30 days, a second release rate for a duration of 0-30 days, and a third release rate of 0-30 days. The second release rate was greater than the first release rate and the third release rate. The total duration of controlled release varied from approximately 40 days to approximately 80 days. Table 1 provides additional embodiments for which a burst effect below 5%, an initial release less than 10%, a release duration greater than 30 days and triphasic release profile have been confirmed in vitro. FIG. 15A-E and FIG. 16A-E show the individual experiments that were averaged to generate the curves in FIG. 3A and FIG. 3B, respectively.

The experiments above were repeated with 20% PEG solids. Extended release in vitro assays were conducted in which the controlled release profile of pre-mixed 8-arm, 4-arm, and blended 8-arm/4-arm PEG gels were evaluated. The cross-linked compositions were formed by mixing either 8-arm PEG functionalized with thiol or acrylate in a 1:1 ratio and ABT-308 in a 1:25 ratio of biologic therapeutic to PEG solids, 4-arm PEG functionalized with thiol or acrylate in a 1:1 ratio and ABT-308 in a 1:12.5 ratio of biologic therapeutic to PEG solids, or a mixture of the 8-arm and 4-arm PEG formulations in a ratio of 25:75, 50:50 or 75:25 8-arm PEG to 4-arm PEG. The total weight to volume ratio of the PEGs in solution was 20%. Both pre-mixed and non-pre-mixed formulations were studied. As shown in FIG. 17A and FIG. 17B, it was observed that all cross-linked compositions exhibited a triphasic release profile of the biologic therapeutic, with an initial release rate for a duration of 0-30 days, a second release rate for a duration of 0-30 days, and a third release rate of 0-30 days. The second release rate was greater than the first release rate and the third release rate. The total duration of controlled release varied from approximately 40 days to approximately 80 days. Additionally, increasing the proportion of 8-arm PEG will increase the delay between complete mAb release and complete gel degradation. It further was observed that non-premixed cross-linked compositions can produce a larger burst effect.

Additionally, and as shown in FIG. 17C, the experiments above were repeated with 8-arm pre-mixed or non-pre-mixed PEG formulations with a total weight to volume ratio of PEGs in solution of either 12 or 20 percent and containing either 8 or 32 µg/µl of antibody. Triphasic release of the biologic therapeutic was observed for up to 85 days. Complete degradation of the cross-linked formulation occurs by day 100. Greater burst release as described was observed with greater total PEG solids in solution.

The swelling ratio, as determined by the increase in mass relative to the initial mass of the cross-linked composition over time of the formulations described above was also plotted. These graphs are provided in FIG. 18A and FIG. 18B. As shown in Table 8, non-premixed cross-linked compositions absorb significantly more water than premixed cross-linked compositions.

5.4 Example 4

8-arm PEG functionalized with thiol or acrylate in a 1:1 ratio dissolved in 0.05M phosphate suspension buffer at pH 3.5 was combined with 0.16 mg ABT-308 (a monoclonal antibody) tagged with fluorophores and was dissolved in 0.2M bicarbonate suspension buffer at pH 9.0. The combined solutions were mixed by aspirating into and ejecting from (plunging) a syringe. Solutions of both 10% total PEG solids and 20% total PEG solids were mixed. After 5, 15 or 30 syringe plunges, during which the cross-linking reaction was initiated, the mixture was aspirated, cross-linking was permitted to proceed to near-completion, and the partially-formed cross-linked compositions was ejected. After cross-linking was complete, the cross-linked composition was observed under phase contrast imaging and fluorescence imaging at 20× magnification. The experiment was repeated for 4-arm PEG solutions of 10% total PEG solids and 20% total PEG solids. Surprisingly, it was observed that the 4-arm PEG solids mixtures resulted in non-uniform precipitate size and inhomogeneous distribution of the precipitates throughout the formulation. Moreover, precipitate size increased with the number of mixing plunges, such that the mixtures formed by plunging 30 times exhibited large, sticky precipitates and incomplete precipitation. The 8-arm PEG solids mixture, in contrast, exhibited relative uniformity of precipitate size when mixed by 5, 15 or 30 plunges. An increase in precipitate size was observed with greater number of plunges. The 20% PEG solids solutions exhibited biologic therapeutic precipitate sizes between about 100 nm and 1 µm in diameter. These results are illustrated in FIG. 6A, FIG. 6B, FIG. 6C and FIG. 6D. FIG. 6A illustrates 10% 4-arm PEG formulations; FIG. 6B illustrates 10% 8-arm PEG formulations; FIG. 6C illustrates 20% 4-arm PEG formulations; FIG. 6D illustrates 20% 8-arm PEG formulations.

5.5 Example 5

Figure 4A:
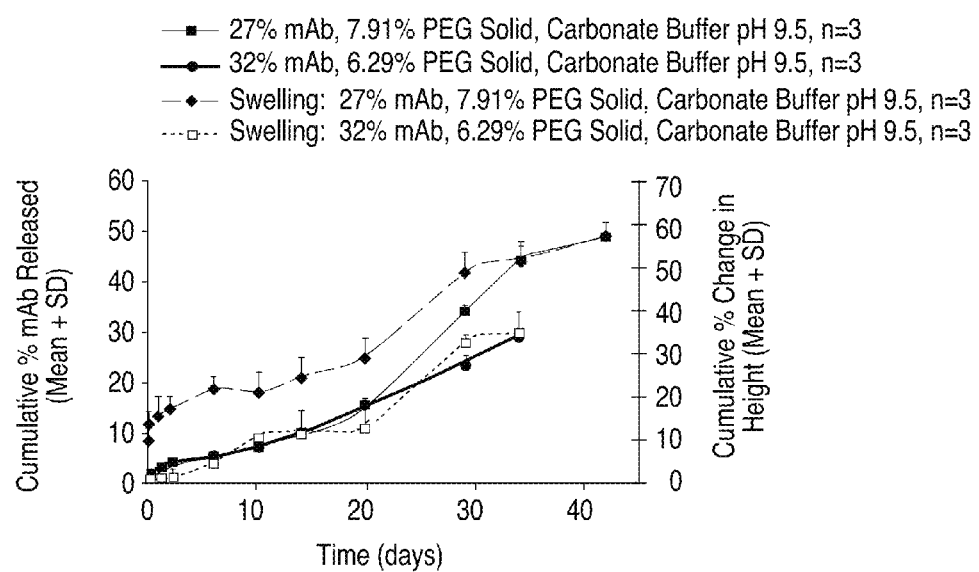
FIG. 4A depicts illustrates the swelling of cross-linked compositions in parallel to release of monoclonal antibody in vitro.

Formulations of 4-arm PEG functionalized with thiol or acrylate in a 1:1 ratio provided in a concentration of either 7.91% by volume with 27% monoclonal antibody (adalimumab) loading by weight or 6.29% by volume with 32% monoclonal antibody (adalimumab) loading by weight. The formulations were mixed with carbonate activation buffer at pH 9.5 to form cross-linked compositions. Swelling, as observed by the percentage of change in height in a plastic tube, was observed in parallel to the percentage of antibody released. As illustrated in FIG. 4A, swelling of the cross-linked compositions corresponds closely with the proportion of antibody released. Swelling of the gels over time is shown in FIG. 19.

Figure 4B:
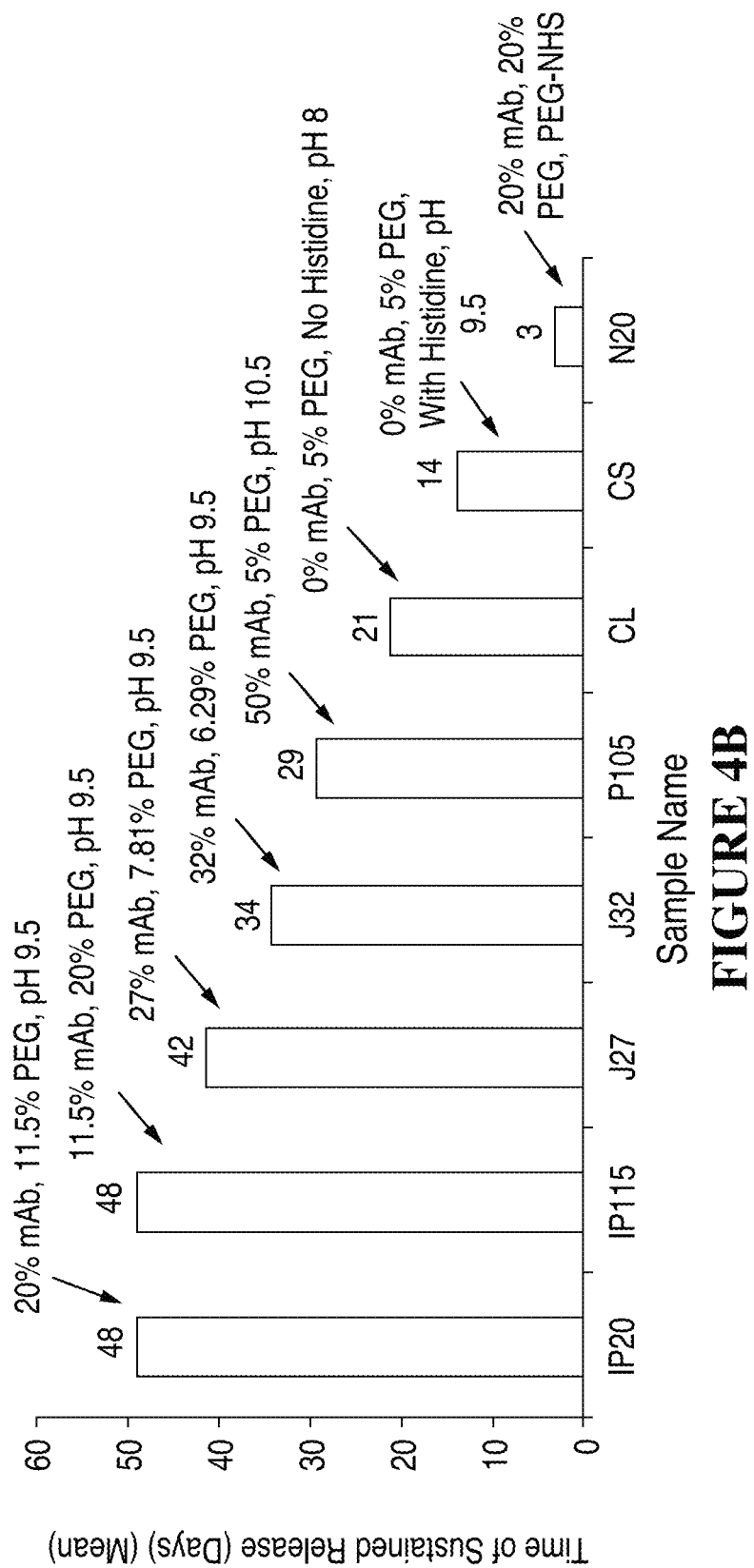
FIG. 4B depicts times to visible dissolution of various cross-linked compositions formulations in vitro.

Additionally, formulations of 4-arm PEG with various proportions of PEG solids concentration, monoclonal antibody loading, solution buffer compositions, and functional groups were cross-linked to form cross-linked compositions. The cross-linked compositions were incubated in vitro and the time to dissolution, as determined by visual inspection, for the various compositions was recorded. The components of the cross-linked compositions and corresponding dissolution times are illustrated in FIG. 4B.

5.6 Example 6

Formulations of 4-arm PEG-Acr/PEG-SH and adalimumab in either 15 mM histidine buffer at pH 5.2 or in lyophilized form re-dissolved in buffer are mixed with either 0.2M phosphate buffer at pH 8 or pH 10 or 0.2M carbonate-bicarbonate buffer at pH 9.5 and pH 10.5. The gels were formed in sterile centrifuge tubes, and gelation times were measured by visible inspection as resistance to gravity flow. Antibody release was also measure over time by adding release medium (PBS with 0.1 wt % TWEEN 80 and 0.05 wt % sodium azide at pH 7.4) one hour after gel formation and taking 600 uL samples at specified time intervals. The sample volumes were immediately replaced. FIG. 20 and FIG. 21 depict the gelation time and antibody release over time, respectively, of the cross-linked compositions as indicated. The results indicate that several variables influence gelation time and mAb release.

5.7 Example 7

5 Groups (groups A-E) of 9 Lewis Rats (subdivided into three groups of three) were administered ABT-308 monoclonal antibody to the intra-articular space of the hind limb. Group A received 0.16 mg of unformulated lyophilized mAb. Group B received 0.16 mg mAb formulated in 8-arm PEG-Acr/SH suspended in 0.05M phosphate buffer at pH 3.5 and mixed with 0.2M phosphate buffer with a pH of 9.0. The PEG was provided in a 20% weight to volume ratio relative to the buffers provided. The molecular weight of the PEG was 10 kDa and the PEG-Acr and PEG-SH were combined in a 1:1 ratio; the suspension and activation buffers were provided in a 1:1 ratio. Group C received 0.16 mg mAB formulated in 20% 8-arm PEG-Acr/SH. The PEG was provided in a 20% weight to volume ratio relative to the buffers provided. The PEG and mAb were mixed in 0.2M phosphate buffer with a pH of 7.5. The molecular weight of the PEG was 10 kDa and the PEG-Acr and PEG-SH were combined in a 1:1 ratio. Group D received 0.16 mg mAb in PEG-Acr/SH provided in a 50:50 ratio of 4-arm and 8-arm PEG. The PEG was provided in a 20% weight to volume ratio relative to the buffers provided. The molecular weight of the PEG was 10 kDa and the PEG-Acr and PEG-SH were combined in a 1:1 ratio. Group E received 0.32 mg mAB formulated in 20% 8-arm PEG-Acr/SH. The PEG was provided in a 20% weight to volume ratio relative to the buffers provided. Group A underwent synovial lavage on day 14, while groups B-E underwent synovial lavage on days 1, 7 and 14. FIG. 10 illustrates the serum and synovial fluid concentrations of the antibody in Group C over 14 days. Relatively high synovial concentrations were maintained, while serum exposure was minimized, over the duration of the experiment. Synovial fluid concentrations, serum concentrations, and ratio of synovial fluid:serum concentrations are provided for each of the treatment groups in Table 5. AUC exposure data for each group is provided in Table 7. The average synovial and serum mAb concentrations by group and time point are illustrated in FIG. 22. FIG. 23A, FIG. 23B, FIG. 23C and FIG. 23D provide serum and synovial fluid concentrations for treatment groups B, C, D and E respectively, while FIG. 24A, FIG. 24B, FIG. 24C, FIG. 24D and FIG. 24E provide the systemic exposure and AUC exposure data for each individual animal in the respective study group.

5.8 Example 8

5 Groups (groups A-E) of 9 Lewis Rats (subdivided into three groups of three) were administered ABT-308 monoclonal antibody to the intra-articular space of the hind limb. Group A received 0.16 mg of unformulated lyophilized mAb. Group B received 0.16 mg mAb formulated in 4-arm PEG-Acr/SH. The PEG was provided in a 20% weight to volume ratio relative to the buffers provided. The molecular weight of the PEG was 10 kDa and the PEG-Acr and PEG-SH were combined in a 1:1 ratio; the suspension and activation buffers were provided in a 1:1 ratio. Group C received 0.16 mg mAB formulated in 4-arm PEG-Acr/SH. The PEG was provided in a 20% weight to volume ratio relative to the buffers provided. The PEG and mAb were mixed in 0.2M phosphate buffer with a pH of 7.5. The molecular weight of the PEG was 2 kDa and the PEG-Acr and PEG-SH were combined in a 1:1 ratio. Group D received 0.16 mg mAb in PEG-Acr/SH provided in 4-arm PEG-Acr/SH. The PEG was provided in a 10% weight to volume ratio relative to the buffers provided. The molecular weight of the PEG was 10 kDa and the PEG-Acr and PEG-SH were combined in a 1:1 ratio. Group E received 0.16 mg mAB formulated in 8-arm PEG-Acr/SH. The PEG was provided in a 20% weight to volume ratio relative to the buffers provided. Group A underwent synovial lavage on day 14, while groups B-E underwent synovial lavage on days 1, 7 and 14. The average synovial and serum mAb concentrations by group are illustrated in FIG. 25 and Table 9 provides serum AUC totals for all groups.

This study was repeated with three groups. Group A received 0.16 mg unformulated lyophilized mAb, group D received 0.16 mg mAB in 10% 8-arm PEG-AC/SH (suspended in 0.05M citrate-phosphate buffer at pH 3.5 and crosslinked with 0.2M bicarbonate buffer at pH 9, and group E received 0.16 mg mAB in 20% 8-arm PEG-AC/SH (suspended in 0.05M citrate-phosphate buffer at pH 3.5 and crosslinked with 0.2M bicarbonate buffer at pH 9. Group A had synovial lavage samples extracted at day 14, while groups D and E had synovial lavage samples extracted at day 1, day 7 and day 14. Serum exposures and AUC calculations are illustrated in FIG. 23. Synovial fluid exposures are provided in Table 6. Results for the respective treatment groups are illustrated in FIG. 26A and FIG. 26B. Results for individual animals of each group are illustrated in FIG. 27A-C. Further experimental data illustrating that a ratio of systemic to local concentration of below approximately 0.1 is maintained for at least six weeks is provided in FIG. 28. Corresponding AUC data is provided in Table 10.

5.9 Example 9

Gelation times and uniformity of precipitation were evaluated for 100 µl 20% 8-arm cross-linked compositions with loadings of 8, 16, 24 and 32 µg of ABT-308 per µL composition. Premixed formulations were mixed in 0.2M pH 7.5 phosphate buffer, while non-premixed formulations were suspended in 0 0.05M pH 3.5 citrate-phosphate buffer and mixed with 0.2M pH 9.0 bicarbonate buffer. Average gelation times and uniformity of precipitation are provided in Table 11.

5.10 Example 10

Gelation times were evaluated for 100 µl 20% 8-arm cross-linked compositions with loadings of 8 µg of lyophilized ABT-308 or frozen anti-MMP13 per µL composition. Premixed formulations were mixed in 0.2M pH 7.5 phosphate buffer, while non-premixed formulations were suspended in 0 0.05M pH 3.5 citrate-phosphate buffer and mixed with 0.2M pH 9.0 bicarbonate buffer. For pre-mixed solutions, the mAb was either premixed in buffer and combined with PEG solids upon cross-linking or pre-mixed in PEG solids prior to cross-linking Average gelation times are provided in Table 12.

5.11 Example 11

Table 4A and Table 4B provide experimental systemic and synovial fluid concentration data after intra-articular administration of formulated mAb or intravenous administration of unformulated mAb following MMT surgery in rats. MMT surgery was performed on three groups (A-C) of Lewis rats on day 0 as a model of osteoarthritis pathology. On day 5, the rats were either injected with formulated anti-MMP13 or ABT-308 mAb to the intra-articular space of the hind limb on which surgery was performed or administered 700 mg/kg body weight anti-MMP13 intravenously. Formulations were either premixed or non-premixed. On day 7, serum and synovial lavage samples were collected. Antibody concentrations were analyzed with anti-IL-13 MSD assays to determine ABT-308 concentrations or anti-MMP13 MSD assays to determine anti-MMP13 concentrations. Experimental results are provided in Table 12A (for non-premixed formulations) and Table 12B (for premixed formulations).

5.12 Example 12

Formulations of 10000 MW 4-arm PEG with a 1:1 ratio of PEG-Acr:PEG-SH, 4.84% total PEG solids and 50% mAb loading were formed in sterile centrifuge tubes to study in vitro mAb (adalimumab) release. Antibody integrity after release was measured over time by adding release medium (PBS with 0.1 wt % TWEEN 80 and 0.05 wt % sodium azide at pH 7.4) one hour after gel formation and taking 600 uL samples at specified time intervals. Gels formed in less than ten seconds at 37 degrees Celsius by visual inspection. FIG. 29 and Table 13 illustrate the results of size exclusion chromatography performed upon the released monoclonal antibody. Antibody released from the cross-linked composition exhibits a high proportion of monomers relative to fragments and aggregates, indicating structural preservation upon re-solubilization. The concentration of released mAb was determined by absorbance at 280 nm on a SpectraMax 96-well plate reader using a 96-well quartz plate. The absorbance for each sample was compared to a standard mAb curve for each time point and adjusted for blank release medium absorbance. FIG. 30 illustrates average concentration of mAb released over time, while FIG. 31 illustrates the average percentage of initial mAb administered that was released over time.

Formulations of 20% 8-arm PEG-SH/Acr with an anti-MMP13 antibody:polymer loading ratio of 1:25 were cross-linked and % of cumulative mAb release in vitro was monitored. Released monoclonal antibody was collected and its integrity examined by size exclusion chromatography. FIG. 32 illustrates cumulative release of mAb over time. FIG. 33 depicts size exclusion chromatography results showing a high proportion of monomers relative to aggregates and fragments.

5.13 Example 13

Figure 5:
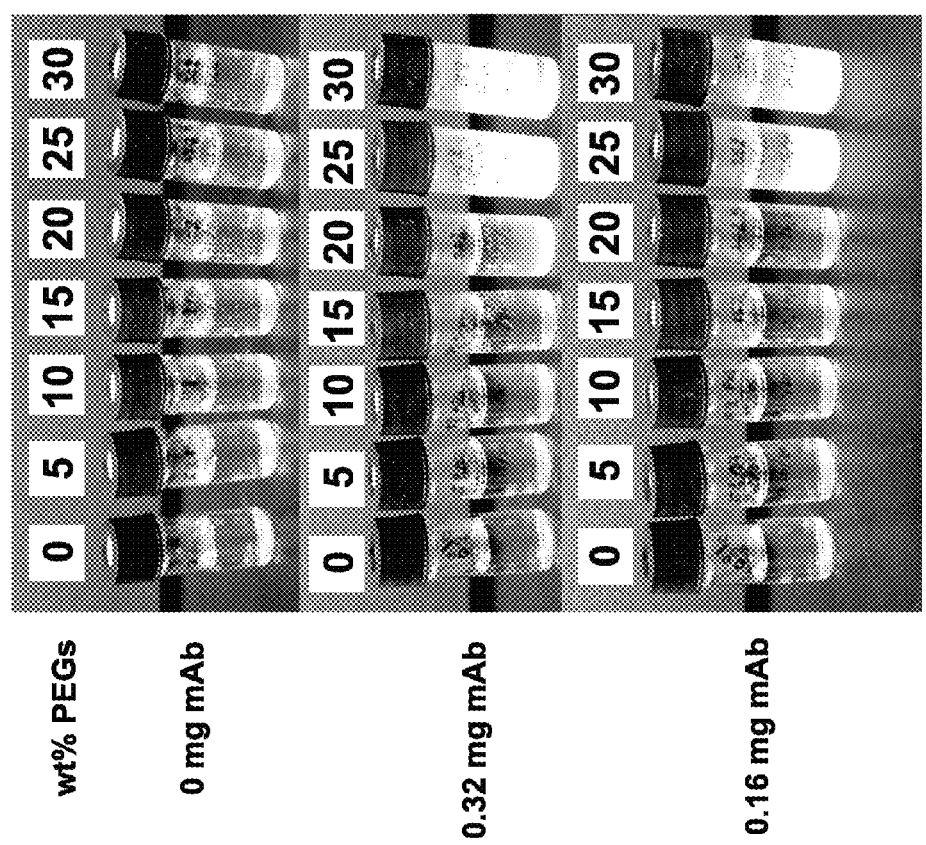
FIG. 5 illustrates visible precipitate formation and precipitate sedimentation as a function of PEG solids concentration and biologic therapeutic concentration in some formulations according to the disclosed subject matter.

Formulations of 8-arm PEG-SH/Acr consisting of either 0, 5, 10, 15, 20, 25 or 30 percent PEG solids by weight and 0 mg, 0.16 mg or 0.32 mg of mAb (ABT-308). The total volume of the formulation is 20 μl. The cross-linked formations are formed in clear vials for visual inspection. All formulations without mAb were clear. In the formulations containing 0.16 mg total mAb, the 20% PEG and lower formulations are clear, while the 25% and 30% formulations showed sedimented precipitates by visual inspection. In the formulations containing 0.32 mg mAb, the 20% PEG formulation exhibited suspended precipitates, the formulations containing less than 20% PEG were clear, and the formulations containing 25% PEG or 30% PEG by weight exhibited floating and sedimented precipitates. These experiments are illustrated in FIG. 5.

5.14 Example 14

Formulations of 10000 MW 8-arm with a 1:1 ratio of PEG-Acr:PEG-SH were prepared for intra-ocular injection. Formulations of 12% weight PEG by volume and 20% weight PEG by volume were prepared having the compositions shown in Table 14. No biologic was included in either formulation.

Each formulation was pre-mixed by manual plunging back and forth between two preloaded 1-ml syringes fitted with a female-to-female luer lock adapted, where one syringe contains a solution of 8-arm PEG-SH and the other contains a solution of 8-arm PEG-Acr for 5-10 seconds before aspiration into a 1-ml Becton Dickinson syringe having a 30 Gauge opthalmic needle and an improvised needle stop at a depth of 5 mm to ensure a uniform injection volume of 50 ul. After pre-mixing and aspiration, 50 ul of either the 12% weight PEG by volume formulation or the 20% weight PEG by volume formulation was injected into the intravitreal space of each of six New Zealand White Rabbit eyes. Each injection was timed to have a duration of approximately 5 seconds. The eyes were observed during and after gelation, and subsequently dissected to observe the lens and retina and extract the formed hydrogels.

Each formulation was injectable through a 30 Gauge opthalmic needle. No significant bulging of the eye was observed after injection, and each formulation cross-linked in situ in the intra-vitreal space to form a gel. The gels remained optically clear, and were sufficiently rigid to be gripped and manipulated by a forceps. It was observed that the 20% PEG by weight formulation gels were more rigid than the 12% PEG by weight formulation gels. No ocular tissue adherence was observed on extraction of the gels, and no lens puncture or retina damage was observed on examination of the dissected eyes. The gelation time of the hydrogel formulations was evaluated experimentally in vitro by visually observing and timing the duration until a formulation mixed as described above no longer flows inside a test microtube. The 12% formulation gelated in approximately 45 seconds, while the 20% formulation gelated in approximately 23 seconds.

TABLE 1

| | % PEG | P/NP | # arms (%) | [ug API/ul gel] | API | D:P ratio | Buffer | In vitro study# | In vivo PK confirmation |
|---|---|---|---|---|---|---|---|---|---|
| 1) | 20 | P | 8(100) | 16 | ABT-308 | 01:12.5 | A + B | 7, 12 | NA |
| 2) | 20 | NP | 8(100) | 16 | ABT-308 | 01:12.5 | C | 7 | NA |
| 3) | 10 | P | 8(100) | 8 | ABT-308 | 01:12.5 | A + B | 8 | NA |
| 4) | 10 | P | 8(75):4(25) | 8 | ABT-308 | 01:12.5 | A + B | 8 | NA |
| 5) | 15 | P | 8(100) | 8 | ABT-308 | 01:18.7 | A + B | 8, 13 | NA |
| 6) | 15 | P | 8(75):4(25) | 8 | ABT-308 | 01:18.7 | A + B | 8 | NA |
| 7) | 15 | P | 8(50):4(50) | 8 | ABT-308 | 01:18.7 | A + B | 8 | NA |
| 8) | 20 | NP | 8(50):4(50) | 16 | ABT-308 | 01:12.5 | C | 12 | NA |
| 9) | 20 | NP | 8(25):4(75) | 16 | ABT-308 | 01:12.5 | C | 12 | NA |

TABLE 1-continued

| | % PEG | P/NP | # arms (%) | [ug API/ul gel] | API | D:P ratio | Buffer | In vitro study# | In vivo PK confirmation |
|---|---|---|---|---|---|---|---|---|---|
| 10) | 20 | P | 8(100) | 8 | ABT-308, anti-MMP13 | 1:25 | A + B | 13, 14, 15 | ✓ |
| 11) | 15 | NP | 8(100) | 8 | ABT-308 | 01:18.7 | C | 13 | NA |
| 12) | 20 | NP | 8(100) | 8 | ABT-308 | 1:25 | C | 15 | ✓ |

TABLE 2

| | Preclinical POC | Human |
|---|---|---|
| Biocompatibility | Non-inflammatory/biodegradable | |
| Duration of Action | 7-30 days | 90 days |
| Dose | 0.1 mg | 5 mg |
| Release Rate | 2% per day | 1-2% per day |
| Initial Burst | <15% of loaded dose | |
| Volume | 0.02 ml | 2 ml |
| Needle Size | 25 G | 22 G |
| Route | Intra-articular injections into large joints | |
| Desired Synovial Levels | >EC90 for 7-30 days | >EC90 for 90 days |
| Desired Plasma Levels | <1% of synovial levels | |
| Product Stability | — | >18 months at 2-8° C. |

TABLE 3

| | Animal | Time (hour) | Synovial Fluid Concentration (ug/mL) | Serum Concentration (ug/mL) | Serum:Synovial Fluid Ratio |
|---|---|---|---|---|---|
| Unformulated Antibody | A1 | 336 | 0.6 | 4.38 | 7.356 |
| | A2 | 336 | 0.42 | 2.61 | 6.275 |
| | A3 | 336 | 0.43 | 1.36 | 3.136 |
| | Average | | 0.48 | 2.78 | 5.589 |
| 20% 8-arm PEG-AC/SH (10 kDa, 0.16 mg mAb) | B1 | | 48.73 | 0.22 | 0.005 |
| | B2 | | 192.09 | 3.19 | 0.017 |
| | B3 | | 102.29 | 0.92 | 0.009 |
| | Average | | 114.37 | 1.44 | 0.01 |
| | B4 | | 133.57 | 0.85 | 0.006 |
| | B5 | | 123.4 | 0.28 | 0.002 |
| | B6 | | 31.9 | 2.87 | 0.09 |
| | Average | | 96.29 | 1.33 | 0.033 |
| | B7 | | 80.48 | 1.5 | 0.019 |
| | B8 | | 23.04 | 0.69 | 0.03 |
| | B9 | | 53.17 | 2.4 | 0.045 |
| | Average | | 52.22 | 1.53 | 0.031 |

TABLE 4A

| Group/Dose | Animal | Time post injection (hour) | Synovial Fluid Concentration (ug/mL)* | Serum Concentration (ug/mL) | Serum:Synovial Fluid Ratio |
|---|---|---|---|---|---|
| Group A 20 ul IA Non-premixed 20% 8Arm-PEG-AC/-SH (10 kDa, 1:1) 0.16 mg anti-MMP13 mAb | A1 | 48 | 11.55 | 0.91 | 0.08 |
| | A2 | 48 | 12.15 | 0.46 | 0.04 |
| | A3 | 48 | 1.42 | 1.07 | 0.75 |
| | A4 | 48 | 11.48 | 0.62 | 0.05 |
| | A5 | 48 | 38.74 | 0.63 | 0.02 |
| | A6 | 48 | 6.32 | 0.46 | 0.07 |
| | A7 | 48 | no sample | 1.06 | n/a |
| | A8 | 48 | 19.53 | 0.54 | 0.03 |
| | A9 | 48 | 3.42 | 0.84 | 0.25 |
| | Average | | 13.08 | 0.73 | 0.16 |
| | St dev | | 11.84 | 0.24 | 0.25 |
| Group B 20 ul IA Non-premixed 20% 8arm-PEG-AC/-SH (10 kDa, 1:1) 0.16 mg ABT-308 mAb | B1 | 48 | no sample | 4.81 | n/a |
| | B2 | 48 | 42.31 | 0.85 | 0.02 |
| | B3 | 48 | 152.65 | 3.77 | 0.02 |
| | B4 | 48 | 167.39 | 3.14 | 0.02 |
| | B5 | 48 | no sample | 3.14 | n/a |
| | B6 | 48 | no sample | 2.57 | n/a |
| | B7 | 48 | no sample | 2.37 | n/a |
| | B8 | 48 | no sample | 1.89 | n/a |
| | B9 | 48 | 37.71 | 6.29 | 0.17 |
| | Average | | 100.02 | 3.20 | 0.06 |
| | St dev | | 69.57 | 1.61 | 0.07 |
| Group C 100 ul IV 70 mg/kg anti-MMP13 mAb | C1 | 48 | 119.08 | 668.94 | 5.62 |
| | C2 | 48 | 153.27 | 751.57 | 4.90 |
| | C3 | 48 | 113.12 | 553.06 | 4.89 |
| | C4 | 48 | 104.41 | 498.45 | 4.77 |
| | C5 | 48 | 121.52 | 435.85 | 3.59 |
| | C6 | 48 | 111.75 | 500.47 | 4.48 |
| | C7 | 48 | 71.09 | 525.29 | 7.39 |
| | C8 | 48 | 100.87 | 391.25 | 3.88 |
| | C9 | 48 | 104.70 | 607.36 | 5.80 |

TABLE 4A-continued

| Group/Dose | Animal | Time post injection (hour) | Synovial Fluid Concentration (ug/mL)* | Serum Concentration (ug/mL) | Serum:Synovial Fluid Ratio |
|---|---|---|---|---|---|
| | Average | | 111.09 | 548.03 | 5.04 |
| | St dev | | 21.64 | 112.91 | 1.14 |

*Synovial lavage concentrations multiplied by a factor of 5 to account for approximate lavage dilution
ABT-308 Serum LLOQ: Below Quantitation Limit (0.075 ug/mL)
ABT-308 Synovial Fluid LLOQ: Below Quantitation Limit (0.375 ug/mL)
anti-MMP13 Serum LLOQ: Below Quantitation Limit (0.15 ug/mL)
anti-MMP13 Synovial Fluid LLOQ: Below Quantitation Limit (0.05 ug/mL)

TABLE 4B

| Group/Dose | Animal | Time post injection (hour) | Synovial Fluid Concentration (ug/mL)* | Serum Concentration (ug/mL) | Serum:Synovial Fluid Ratio |
|---|---|---|---|---|---|
| Group A | A1 | 48 | no sample | 0.86 | n/a |
| 20 ul IA | A2 | 48 | no sample | 0.61 | n/a |
| Remixed 20% 8Arm- | A3 | 48 | 100.03 | 0.94 | 0.01 |
| PEG-AC/-SH | A4 | 48 | 12.37 | 0.91 | 0.07 |
| (10 kDa, 1:1) | A5 | 48 | no sample | 0.97 | n/a |
| 0.16 mg anti-MMP13 | A6 | 48 | 3.08 | 1.33 | 0.43 |
| mAb | A7 | 48 | no sample | 0.86 | n/a |
| | A8 | 48 | no sample | 1.15 | n/a |
| | A9 | 48 | 15.71 | 1.03 | 0.07 |
| | Average | | 32.80 | 0.96 | 0.14 |
| | St dev | | 45.14 | 0.20 | 0.19 |
| Group B | B1 | 48 | 14.46 | 5.68 | 0.39 |
| 20 ul IA | B2 | 48 | no sample | 8.04 | n/a |
| Premixed 20% 8Arm- | B3 | 48 | 22.12 | 7.67 | 0.35 |
| PEG-AC/-SH | B4 | 48 | no sample | 5.00 | n/a |
| (10 kDa, 1:1) | B5 | 48 | no sample | 2.15 | n/a |
| 0.16 mg ABT-308 | B6 | 48 | no sample | 3.77 | n/a |
| mAb | B7 | 48 | no sample | 2.13 | n/a |
| | B8 | 48 | 59.22 | 1.64 | 0.03 |
| | B9 | 48 | 8.19 | 4.57 | 0.56 |
| | Average | | 26.00 | 4.52 | 0.33 |
| | St dev | | 22.87 | 2.35 | 0.22 |
| Group C | C1 | 48 | 234.47 | 633.14 | 2.70 |
| 100 ul IV | C2 | 48 | 77.01 | 606.87 | 7.88 |
| 70 mg/kg anti- | C3 | 48 | 58.79 | 476.14 | 8.10 |
| MMP13 | C4 | 48 | 61.68 | 512.51 | 8.31 |
| mAb | C5 | 48 | 62.89 | 480.08 | 7.63 |
| | C6 | 48 | 85.87 | 511.80 | 5.96 |
| | C7 | 48 | 75.64 | 527.05 | 6.97 |
| | C8 | 48 | 75.38 | 587.56 | 7.79 |
| | C9 | 48 | 73.61 | 674.90 | 9.17 |
| | Average | | 89.48 | 556.67 | 7.17 |
| | St dev | | 55.06 | 71.14 | 1.90 |

*Synovial lavage concentrations multiplied by a factor of 5 to account for approximate lavage dilution
ABT-308 Serum LLOQ: Below Quantitation Limit (0.075 ug/mL)
ABT-308 Synovial Fluid LLOQ: Below Quantitation Limit (0.375 ug/mL)
anti-MMP13 Serum LLOQ: Below Quantitation Limit (0.15 ug/mL)
anti-MMP13 Synovial Fluid LLOQ: Below Quantitation Limit (0.05 ug/mL)

TABLE 5

| Group/Dose | Animal | Time (hour) | Synovial Fluid Concentration (ug/mL)* | Serum Concentration (ug/mL) | Serum:Synovial Fluid Ratio |
|---|---|---|---|---|---|
| Group A | A1 | 336 | 0.60 | 4.38 | 7.356 |
| Unformulated | A2 | 336 | 0.42 | 2.61 | 6.275 |
| lyo mAb | A3 | 336 | 0.43 | 1.36 | 3.136 |
| 0.16 mg mAb | Average | | 0.48 | 2.78 | 5.589 |
| Group B | B1 | 24 | 18.32 | 1.74 | 0.095 |
| 20% 8Arm- | B2 | 24 | 22.46 | 1.58 | 0.070 |
| PEG-AC/-SH | B3 | 24 | 5.23 | 2.47 | 0.472 |

TABLE 5-continued

| Group/Dose | Animal | Time (hour) | Synovial Fluid Concentration (ug/mL)* | Serum Concentration (ug/mL) | Serum:Synovial Fluid Ratio |
|---|---|---|---|---|---|
| (10 kDa, 1:1) | | Average | 15.34 | 1.93 | 0.212 |
| 0.16 mg mAb | B4 | 168 | BQL | 3.25 | N/A |
| | B5 | 168 | 1.78 | 2.23 | 1.251 |
| | B6 | 168 | 11.20 | 1.09 | 0.097 |
| | | Average | 6.49 | 2.19 | 0.674 |
| | B7 | 336 | 6.94 | 0.14 | 0.020 |
| | B8 | 336 | 0.57 | 1.32 | 2.327 |
| | B9 | 336 | 4.13 | 0.69 | 0.168 |
| | | Average | 3.88 | 0.72 | 0.838 |
| Group C | C1 | 24 | 48.73 | 0.22 | 0.005 |
| 20% 8Arm- | C2 | 24 | 192.09 | 3.19 | 0.017 |
| PEG-AC/-SH | C3 | 24 | 102.29 | 0.92 | 0.009 |
| (10 kDa, 1:1) | | Average | 114.37 | 1.44 | 0.010 |
| 0.16 mg mAb | C4 | 168 | 133.57 | 0.85 | 0.006 |
| | C5 | 168 | 123.40 | 0.28 | 0.002 |
| | C6 | 168 | 31.90 | 2.87 | 0.090 |
| | | Average | 96.29 | 1.33 | 0.033 |
| | C7 | 336 | 80.46 | 1.50 | 0.019 |
| | C8 | 336 | 23.04 | 0.69 | 0.030 |
| | C9 | 336 | 53.17 | 2.40 | 0.045 |
| | | Average | 52.22 | 1.53 | 0.031 |
| Group D | D1 | 24 | 23.69 | 2.36 | 0.10 |
| 50:50 4Arm:8Arm- | D2 | 24 | 9.43 | 1.89 | 0.20 |
| PEG-AC/-SH | D3 | 24 | 20.68 | 2.25 | 0.11 |
| (10 kDa, 1:1) | | Average | 17.93 | 2.17 | 0.14 |
| 0.16 mg mAb | D4 | 168 | 9.54 | 0.78 | 0.08 |
| | D5 | 168 | 0.54 | 2.45 | 4.51 |
| | D6 | 168 | 2.93 | BQL | N/A |
| | | Average | 4.34 | 1.62 | 2.29 |
| | D7 | 336 | 0.55 | 0.28 | 0.50 |
| | D8 | 336 | 1.21 | BQL | N/A |
| | D9 | 336 | BQL | BQL | N/A |
| | | Average | 0.88 | 0.28 | 0.50 |
| Group E | E1 | 24 | 209.40 | 8.85 | 0.04 |
| 20% 4Arm- | E2 | 24 | 305.94 | 14.53 | 0.05 |
| PEG-AC/-SH | E3 | 24 | 56.53 | 7.92 | 0.14 |
| (10 kDa, 1:1) | | Average | 190.62 | 10.43 | 0.08 |
| 0.32 mg mAb | E4 | 168 | 29.97 | 9.74 | 0.32 |
| | E5 | 168 | 0.52 | 7.35 | 14.26 |
| | E6 | 168 | 4.13 | 13.89 | 3.37 |
| | | Average | 11.54 | 10.33 | 5.98 |
| | E7 | 336 | 1.21 | 7.32 | 6.05 |
| | E8 | 336 | 2.39 | 6.59 | 2.75 |
| | E9 | 336 | 0.35 | 1.13 | 3.24 |
| | | Average | 1.32 | 5.01 | 4.01 |

*Synovial lavage concentrations multiplied by a factor of 5 to account for approximate lavage dilution
LLOQ: Below Quantitation Limit (0.375 ug/mL)

TABLE 6

| Group/Dose | Animal | Time (hour) | Synovial Fluid Concentration (ug/mL)* | Serum Concentration (ug/mL) | Serum:Synovial Fluid Ratio |
|---|---|---|---|---|---|
| Group A | A1 | 336 | BQL | 2.79 | n/a |
| Unformulated | A2 | 336 | 0.44 | 3.30 | 7.42 |
| lyo mAb | A3 | 336 | BQL | 3.38 | n/a |
| 0.16 mg mAb | | Average | 0.44 | 3.16 | 7.42 |
| Group D | D1 | 24 | 16.60 | 3.19 | 0.19 |
| 10% 8Arm- | D2 | 24 | 0.99 | 5.55 | 5.61 |
| PEG-AC/-SH | D3 | 24 | 10.14 | 3.54 | 0.35 |
| (10 kDa, 1:1) | | Average | 9.24 | 4.09 | 2.05 |
| 0.16 mg mAb | D4 | 168 | 17.01 | 2.66 | 0.16 |
| | D5 | 168 | 8.37 | 1.71 | 0.20 |
| | D6 | 168 | 9.22 | 3.22 | 0.35 |
| | | Average | 11.53 | 2.53 | 0.24 |
| | D7 | 336 | 4.01 | 1.96 | 0.49 |
| | D8 | 336 | 0.48 | 2.20 | 4.61 |
| | D9 | 336 | BQL | 1.20 | n/a |
| | | Average | 2.24 | 1.79 | 2.55 |
| Group E | E1 | 24 | 22.20 | 2.89 | 0.13 |
| 20% 8Arm- | E2 | 24 | 13.19 | 2.57 | 0.19 |

TABLE 6-continued

| Group/Dose | Animal | Time (hour) | Synovial Fluid Concentration (ug/mL)* | Serum Concentration (ug/mL) | Serum:Synovial Fluid Ratio |
|---|---|---|---|---|---|
| PEG-AC/-SH | E3 | 24 | 208.20 | 0.82 | 0.00 |
| (10 kDa, 1:1) | Average | | 81.20 | 2.09 | 0.11 |
| 0.16 mg mAb | E4 | 168 | 26.82 | 1.69 | 0.06 |
| | E5 | 168 | 6.88 | 1.85 | 0.27 |
| | E6 | 168 | 5.92 | 1.97 | 0.33 |
| | Average | | 13.21 | 1.84 | 0.22 |
| | E7 | 336 | 1.00 | BQL | n/a |
| | E8 | 336 | 25.86 | 1.68 | 0.07 |
| | E9 | 336 | 23.85 | 1.61 | 0.07 |
| | Average | | 16.90 | 1.65 | 0.07 |

*Synovial lavage concentrations multiplied by a factor of 5 to account for approximate lavage dilution
LLOQ: Below Quantitation Limit (0.375 ug/mL)

TABLE 7

| Group | $AUC_{0-336\ hr}$ (mg · hr/mL) | $AUC_{0-336\ hr}$/Dose (mg · hr/mL/mg/kg) | $C_{max}$ (μg/mL) | $C_{max}$/Dose (μg/mL/mg/kg) | Mean Synovial Fluid Conc. (μg/mL) |
|---|---|---|---|---|---|
| A (8 mg) | 29.5 | 1.0 | 148.7 | 5.1 | 1.01 |
| B (8 mg) | 40.4 | 1.4 | 167.4 | 5.8 | 1.41 |
| C (0.8 mg) | 1.7 | 0.6 | 7.7 | 2.6 | 0.32 |
| D (0.8 mg) | 5.2 | 1.8 | 24.2 | 8.3 | 0.17 |
| E (0.8 mg) | 2.9 | 1.0 | 11.9 | 4.1 | 0.10 |
| G (0.8 mg) | 11.5 | 4.0 | 50.9 | 17.5 | 0.31 |

*Assumed rat weight of 275 g to calculate dose

TABLE 8

| Formulation Blend | % greater swelling [(NP − P)/P] | Days |
|---|---|---|
| 4(0):8(100) | 73.8 | 59 |
| 4(25):8(75) | 24.5 | 59 |
| 4(50):8(50) | 9.7 | 59 |
| 4(75):8(25) | 8.3 | 42 |
| 4(100):8(0) | 19.4 | 35 |

TABLE 9

| Group | $AUC_{0-336\ hr}$ (mg· hr/mL) | $AUC_{0-336\ hr}$/Dose (mg· hr/mL/mg/kg) | $C_{max}$ (μg/mL) | $C_{max}$/Dose (μg/mL/mg/kg) | $T_{max}$ (day) |
|---|---|---|---|---|---|
| A | 1.5 | 2.6 | 7.3 | 12.5 | 1.0 |
| B | 0.6 | 1.1 | 3.1 | 5.4 | 1.6 |
| C | 0.6 | 1.1 | 1.9 | 3.2 | 10.3 |
| D | 0.7 | 1.2 | 2.6 | 4.4 | 1.0 |
| E | 3.2 | 2.7 | 11.5 | 9.9 | 3.0 |

TABLE 10

| Group | AUC 0-336 hours (mg/hr/mL) | AUG 0-336 hours/Dose (mg/hr/mL/mg/kg) | Cmax (ug/mL) | Cmax/Dose (ug/mL/mg/kg) | Tmax (day) |
|---|---|---|---|---|---|
| A | 1.3 | 2.2 | 5.3 | 9.1 | 1 |
| B | 1.3 | 2.2 | 4.4 | 7.6 | 0.2 |
| C | 0.1 | 0.3 | 0.7 | 1.3 | 2.7 |
| D | 0.7 | 1.1 | 3.3 | 5.7 | 2 |
| E | 0.3 | 0.5 | 1.7 | 2.9 | 8 |

TABLE 11

| API | P/NP | API loading (ug/ul gel) | D:P | Avg gel time (min:s) | Uniform/Non-uniform Precipitation |
|---|---|---|---|---|---|
| ABT-308 | NP | 8 | 1:25 | 0:29 | Uniform |
| ABT-308 | NP | 16 | 1:12.5 | 0:30 | Uniform |
| ABT-308 | NP | 24 | 1:8.25 | 0:34 | Non-uniform |
| ABT-308 | NP | 32 | 1:6.33 | 0:32 | Non-uniform |
| ABT-308 | P | 8 | 1:25 | 1:14 | Uniform |
| ABT-308 | P | 16 | 1:12.5 | 1:30 | Uniform |
| ABT-308 | P | 24 | 1:8.25 | 1:55 | Uniform |
| ABT-308 | P | 32 | 1:6.33 | 2:05 | Non-uniform |

TABLE 12

| API | Mixing | % 8-arm PEG | Avg gel time |
|---|---|---|---|
| Anti-MMP13 | Premixed in PEG | 20 | 0:42 |
| ABT-308 | Premixed in PEG | 20 | 1:17 |
| Anti-MMP13 | Non-premixed | 20 | 0:23 |
| ABT-308 | Non-premixed | 20 | 0:30 |
| Anti-MMP13 | Premixed in buffer | 20 | 1:20 |
| ABT-308 | Premixed in buffer | 20 | 1:02 |

TABLE 13

Table 1. SEC results demonstrating stability of up to 14 d release mAb from PEG-PEG gels.

| Formulation | Release Timepoint | % aggregates | % monomer | % fragment |
|---|---|---|---|---|
| 50% mAb, 5% PEG solids, phosphate buffer pH = 10.5 | 2 h | 1.97 | 97.49 | 9.54 |
| | 2 d | 2.92 | 96.53 | 0.55 |
| | 10 d | 1.08 | 96.12 | 2.79 |
| 50% mAb, 5% PEG solids, mixed phosphate-carbonate buffer pH = 10.5, 2 hrs | 2 h | 1.56 | 97.93 | 0.51 |
| | 2 d | 1.50 | 98.15 | 0.35 |
| | 10 d | 1.56 | 96.46 | 1.94 |
| | 14 d | 1.34 | 96.77 | 1.88 |
| IP202 | 7 d | 5.50 | 85.18 | 9.30 |

TABLE 14

| Gel % (w/v) | 8-arm PEG-SH (g) | PEG-SH Buffer Vol (ml) | 8-arm PEG-AC (g) | PEG-AC Buffer Vol (ml) | Buffer Type | Gel Time (s) |
|---|---|---|---|---|---|---|
| 12 | 0.15 | 0.625 | 0.1 | 0.835 | 0.2M pH 7.5 phosphate | 48 |
| 20 | 0.3 | 0.75 | 0.1 | 0.5 | 0.2M pH 7.5 phosphate | 23 |

What is claimed is:

1. A formulation comprising:

(a) a biologic therapeutic; and (b) a plurality of hydrophilic polymer strands comprising a functional group capable of inter-polymer cross-linking;

wherein the plurality of hydrophilic polymer strands comprises PEG-acrylate and PEG-thiol;

wherein the weight ratio of the biologic therapeutic to the plurality of hydrophilic polymer strands is between 1:1 and 1:125;

wherein said formulation, when cross-linked, forms a hydrogel that exhibits reversible precipitation of the biologic therapeutic into precipitates having a size of about 50 nm to about 10 μm in diameter, and exhibits a triphasic release profile of the biologic therapeutic.

2. The formulation of claim 1, wherein the biologic therapeutic is a protein.

3. The formulation of claim 2, wherein the protein is an antibody.

4. The formulation of claim 2, wherein the protein is a dual variable domain antibody.

5. The formulation of claim 2, wherein the protein is selected from the group consisting of: trastuzumab, bevacizumab, adalimumab, ranibizumab, aflibercept, etanercept, rituximab, pegfilgrastim, interferon beta-1a, and infliximab.

6. The formulation of claim 5, wherein the protein is adalimumab.

7. The formulation of claim 1, wherein each hydrophilic polymer strand of said plurality of hydrophilic polymer strands has a structure selected from the group consisting of linear, branched, star, and comb.

8. The formulation of claim 7, wherein the hydrophilic polymer strand structure is branched, star, or comb and has 2 to 16 arms.

9. The formulation of claim 8, wherein the molecular weight of each of the hydrophilic polymer strands is between about 2 and 30 kDa.

10. The formulation of claim 1, wherein PEG-acrylate has 4 or 8 or 16 arms and PEG-thiol has 4 or 8 or 16 arms.

11. The formulation of claim 1, wherein each arm of the hydrophilic polymer strands comprises a functional group.

12. The formulation of claim 10, wherein the ratio of PEG-acrylate and PEG-thiol is between 9:10 to about 10:9.

13. The formulation of claim 1, wherein PEG-acrylate has 8 arms and PEG-thiol has 8 arms.

14. The formulation of claim 1, wherein PEG-acrylate has 16 arms and PEG-thiol has 16 arms.

15. The formulation of claim 1, wherein the formulation is provided in lyophilized form.

16. The formulation of claim 15, further comprising a buffer solution.

17. The formulation of claim 16, wherein said buffer solution has a pH of about 3.5 to about 6.

18. The formulation of claim 17, wherein the weight to volume ratio of PEG-acrylate and PEG-thiol to buffer is between about 5% and about 30%.

19. The formulation of claim 1, wherein the weight ratio of biologic therapeutic to the plurality of hydrophilic polymer strands is between about 1:3.75 and 1:25.

20. A kit comprising:

(a) a formulation comprising a biologic therapeutic and a plurality of hydrophilic polymer strands;

wherein the plurality of hydrophilic polymer strands comprises PEG-acrylate and PEG-thiol;

wherein the weight ratio of the biologic therapeutic to the plurality of hydrophilic polymer strands is between 1:1 and 1:125;

and (b) an activation buffer to induce cross-linking;

wherein said formulation, when cross-linked, forms a hydrogel that exhibits:

(i) a burst effect of <5% of cumulative biologic therapeutic release at 24 hours post administration to a space within the body of a patient;

(ii) an initial release of <10% of cumulative biologic therapeutic release at 7 days post administration to the space within the body of the patient;

(iii) a triphasic release profile where the rate of release post administration to a space within the body of the patient is approximately constant for a first phase of about 0-30 days, for a second phase of about 0-30 days, and for a third phase of about 0-30 days; and (iv) a release duration of 1-3 months post administration to the space within the body of the patient for complete release of the biologic therapeutic.

21. The kit of claim 20, further comprising a delivery device for delivery of the formulation mixed with the activation buffer, wherein the delivery device is selected from a single-bore syringe, a dual-bore syringe or a multi-channel delivery device comprising a mixing head.

22. A kit comprising:

(a) a formulation comprising a biologic therapeutic and a plurality of hydrophilic polymer strands;

wherein the plurality of hydrophilic polymer strands comprises PEG-acrylate and PEG-thiol;

wherein the weight ratio of the biologic therapeutic to the plurality of hydrophilic polymer strands is between 1:1 and 1:125; and (b) an activation buffer to induce cross-linking;

wherein said formulation, when cross-linked, forms a hydrogel that exhibits reversible precipitation of the biologic therapeutic into precipitates having a size of about 50 nm to about 10 μm in diameter, and exhibits a triphasic release profile of the biologic therapeutic.

23. The kit of claim 22, further comprising a delivery device for delivery of the formulation mixed with the activation buffer, wherein the delivery device is selected from a single-bore syringe, a dual-bore syringe or a multi-channel delivery device comprising a mixing head.

24. The formulation of claim 1, wherein the biologic therapeutic is released for 30 to 90 days.

25. The formulation of claim 1, wherein the triphasic release profile comprises a first rate of release for a first period of between about 0 to 30 days, a second rate of release for a second period of about 0 to 30 days, and a third rate of release for a third period of about 0 to 30 days.

* * * * *